(12) United States Patent
Imaizumi et al.

(10) Patent No.: US 11,389,126 B2
(45) Date of Patent: Jul. 19, 2022

(54) GANTRY HOUSING, AND MEDICAL APPARATUS

(71) Applicant: General Electric Company, Schenectady, NY (US)

(72) Inventors: Masayuki Imaizumi, Tokyo (JP); Mitsuru Kobayashi, Tokyo (JP); Kiyomi Abeshima, Tokyo (JP)

(73) Assignee: General Electric Company, Schenectady, NY (US)

( * ) Notice: Subject to any disclaimer, the term of this patent is extended or adjusted under 35 U.S.C. 154(b) by 200 days.

(21) Appl. No.: 16/666,578

(22) Filed: Oct. 29, 2019

(65) Prior Publication Data

US 2020/0137861 A1    Apr. 30, 2020

(30) Foreign Application Priority Data

Oct. 31, 2018 (JP) .............................. JP2018-205583
Aug. 27, 2019 (JP) .............................. JP2019-154944

(51) Int. Cl.
| | | |
|---|---|---|
| *A61B 6/00* | (2006.01) | |
| *H05G 1/04* | (2006.01) | |
| *A61B 6/03* | (2006.01) | |

(52) U.S. Cl.
CPC ............ *A61B 6/4411* (2013.01); *A61B 6/035* (2013.01); *A61B 6/44* (2013.01); *H05G 1/04* (2013.01)

(58) Field of Classification Search
CPC .. H05G 1/04; A61B 6/035; A61B 6/44; A61B 6/4411; H01J 35/18; H01J 2235/18; G21K 1/02
See application file for complete search history.

(56) References Cited

U.S. PATENT DOCUMENTS

| | | | | |
|---|---|---|---|---|
| 4,799,245 A | * | 1/1989 | Bernardi ............... | A61B 6/4447 378/15 |
| 5,493,599 A | * | 2/1996 | Mattson ................... | H05G 1/32 378/150 |
| 5,761,269 A | * | 6/1998 | Sugihara ............... | A61B 6/4488 378/4 |
| 6,314,157 B1 | * | 11/2001 | Tachizaki ............. | A61B 6/4488 378/197 |
| 6,337,894 B1 | * | 1/2002 | Tybinkowski ........ | F16C 19/183 378/4 |
| 7,403,596 B1 | * | 7/2008 | Chaves .................... | H05G 1/04 378/140 |
| 8,681,930 B2 | * | 3/2014 | Sharpless ............... | A61B 6/035 378/197 |
| 9,044,152 B2 | * | 6/2015 | Abenaim ............. | G01N 23/046 |

(Continued)

FOREIGN PATENT DOCUMENTS

JP    2016530912 A    10/2016

*Primary Examiner* — Dani Fox
*Assistant Examiner* — Soorena Kefayati

(57) ABSTRACT

A gantry housing 20 comprises a front cover 30, a main cover 40, a rear cover 50, and a scan window 60. The scan window 60 has a PolyCarbonate (PC) sheet 61, and elastic members 62 and 63. The front cover 30 has a receiving portion 32 in which the elastic member 62 is disposed, and a reinforcing portion 33 for reducing deformation of the PC sheet 61; the rear cover 50 has a receiving portion 52 in which the elastic member 63 is disposed, and a reinforcing portion 53 for reducing deformation of the PC sheet 61.

12 Claims, 48 Drawing Sheets

(56) References Cited

U.S. PATENT DOCUMENTS

| | | | | |
|---|---|---|---|---|
| 2004/0234023 | A1* | 11/2004 | Kollegal | H01J 35/147 |
| | | | | 378/10 |
| 2005/0201512 | A1* | 9/2005 | Muller | A61B 6/4291 |
| | | | | 378/19 |
| 2012/0189094 | A1* | 7/2012 | Neushul | A61B 6/035 |
| | | | | 378/19 |
| 2012/0243657 | A1* | 9/2012 | O'Loughlin | A61B 6/4042 |
| | | | | 378/16 |
| 2013/0343507 | A1* | 12/2013 | Gregerson | A61B 6/03 |
| | | | | 378/189 |
| 2014/0064440 | A1* | 3/2014 | Hara | A61B 6/508 |
| | | | | 378/4 |
| 2014/0119503 | A1* | 5/2014 | Matsuzawa | A61B 6/035 |
| | | | | 378/197 |
| 2014/0169531 | A1* | 6/2014 | Kodaira | F24F 13/24 |
| | | | | 378/196 |
| 2014/0169532 | A1* | 6/2014 | Kodaira | A61B 6/44 |
| | | | | 378/197 |
| 2014/0254746 | A1* | 9/2014 | Kodaira | A61B 6/44 |
| | | | | 378/4 |
| 2015/0092909 | A1* | 4/2015 | Hamilton | H05G 1/04 |
| | | | | 378/4 |
| 2015/0216492 | A1* | 8/2015 | Smith | A61B 6/44 |
| | | | | 378/208 |
| 2015/0265229 | A1* | 9/2015 | Maki | A61B 6/032 |
| | | | | 378/197 |
| 2015/0265232 | A1* | 9/2015 | Kodaira | A61B 6/035 |
| | | | | 378/15 |
| 2016/0374632 | A1* | 12/2016 | David | A61B 6/032 |
| | | | | 378/161 |
| 2017/0105692 | A1* | 4/2017 | Sawanobori | A61B 6/4488 |

* cited by examiner

FIG.33
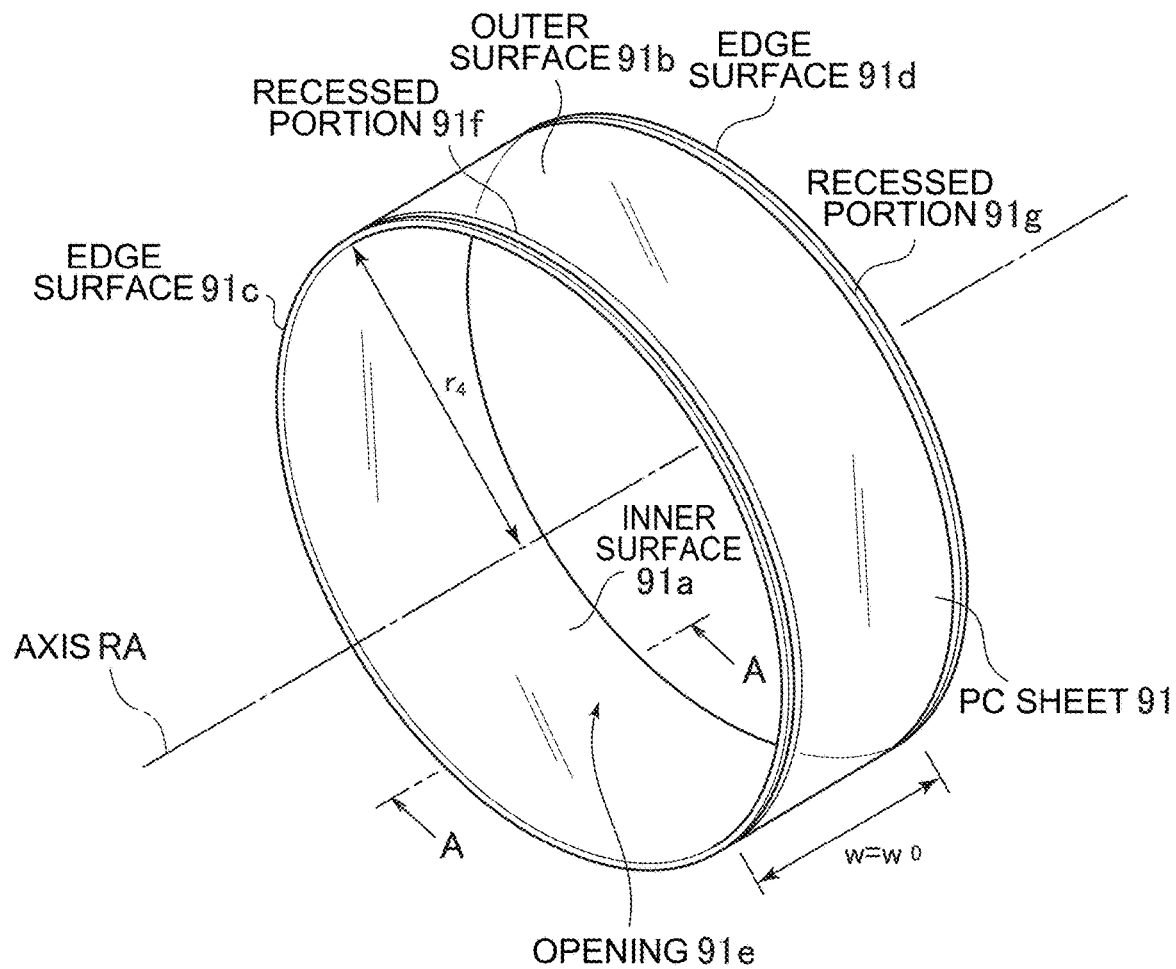
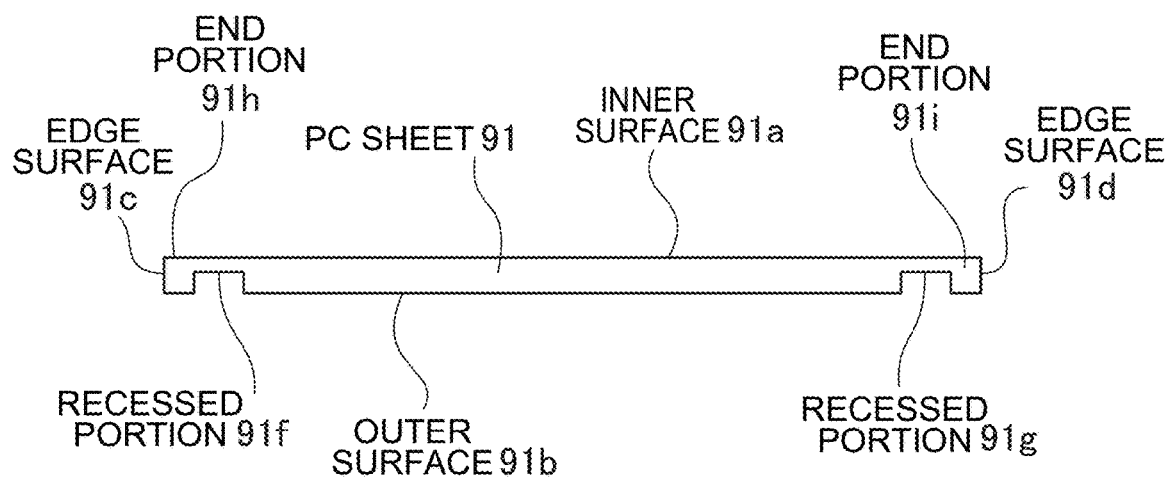
A-A CROSS SECTION

FIG.36
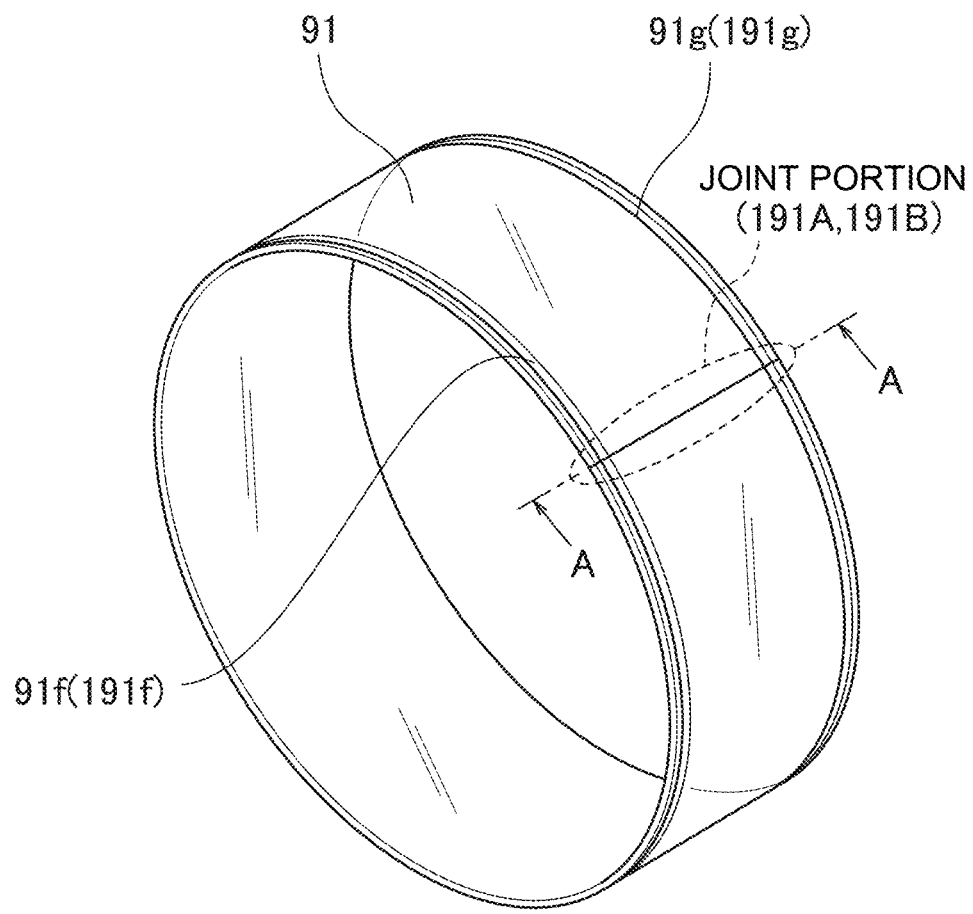
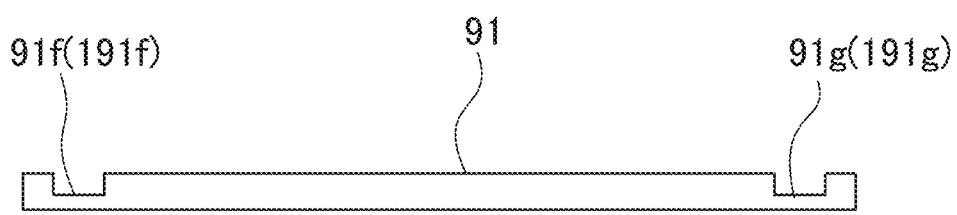
A-A CROSS SECTION

FIG.37
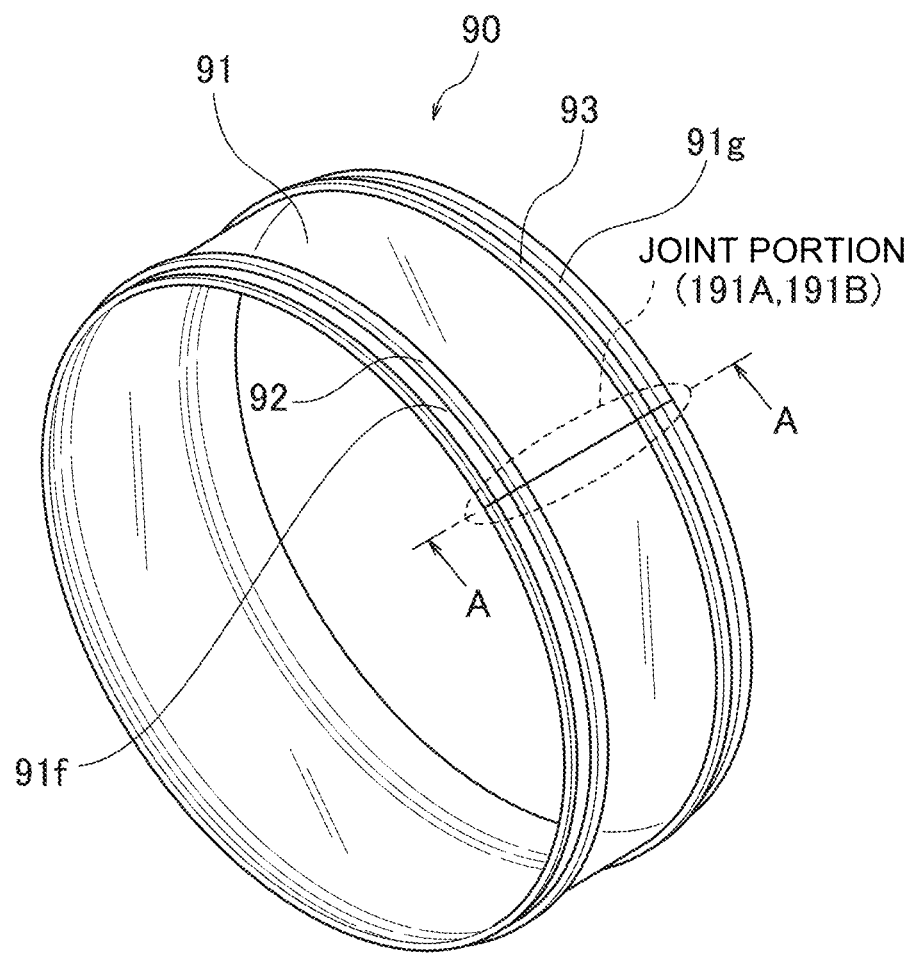
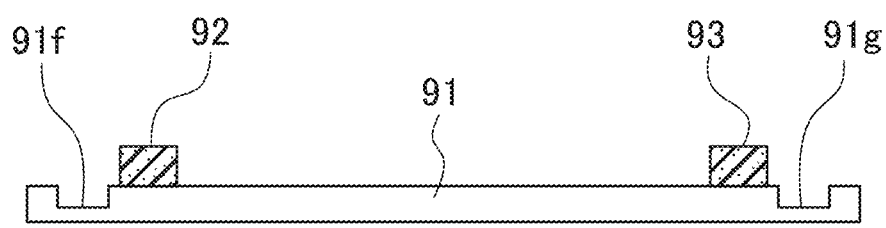
A-A CROSS SECTION

FIG.38
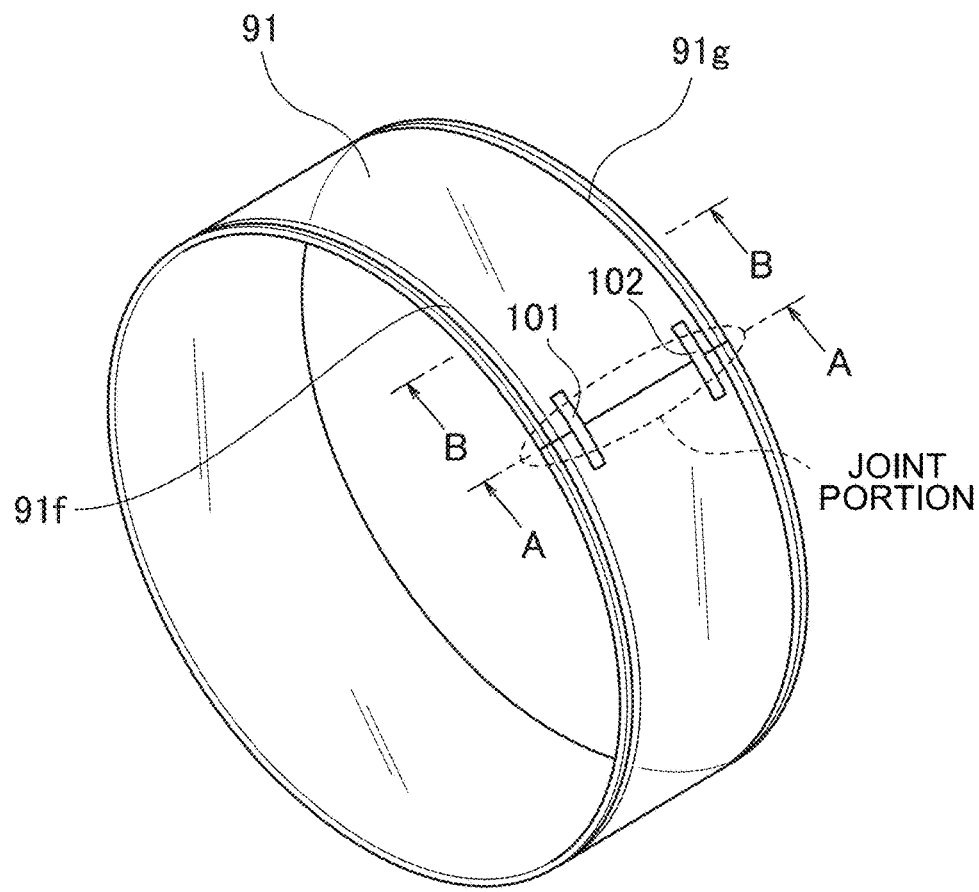
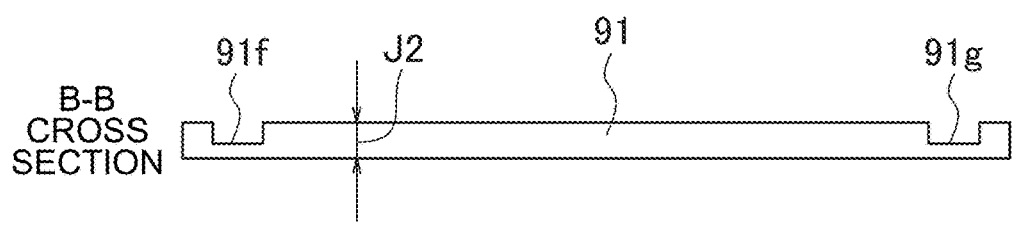
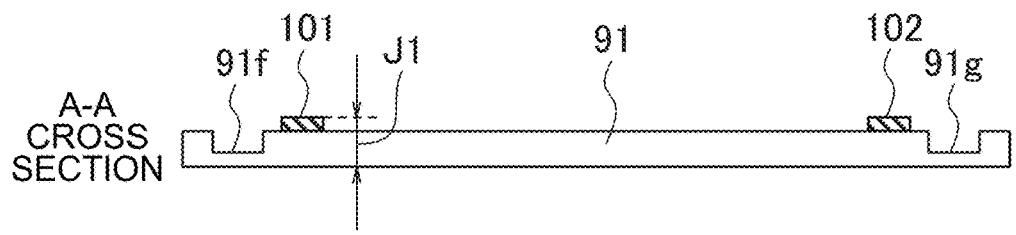

FIG.40
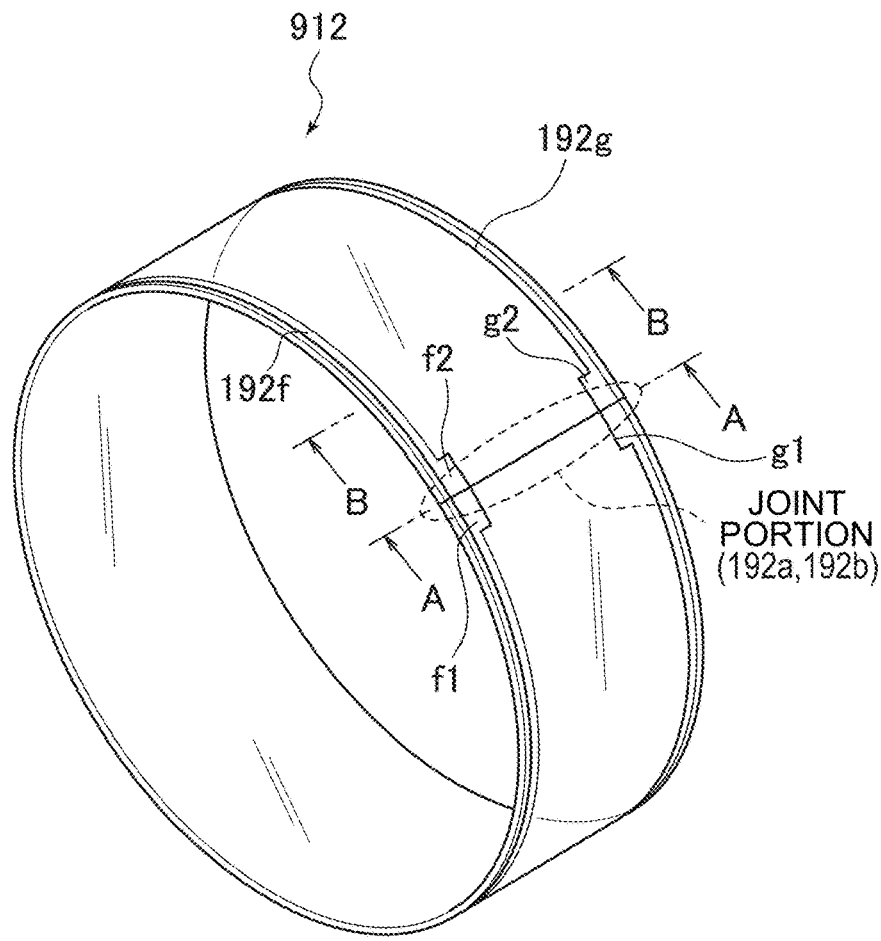
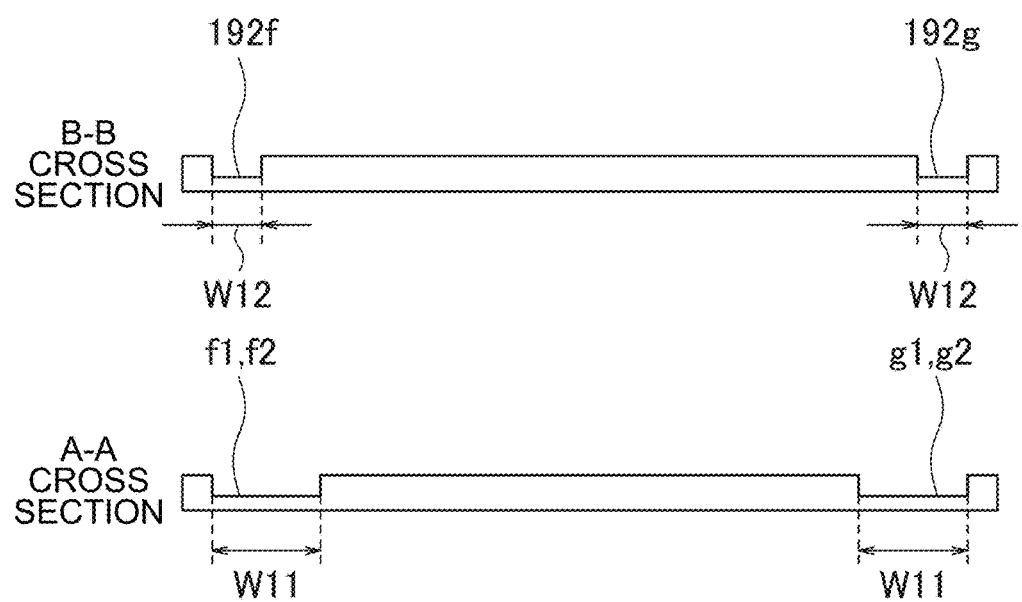

FIG.41
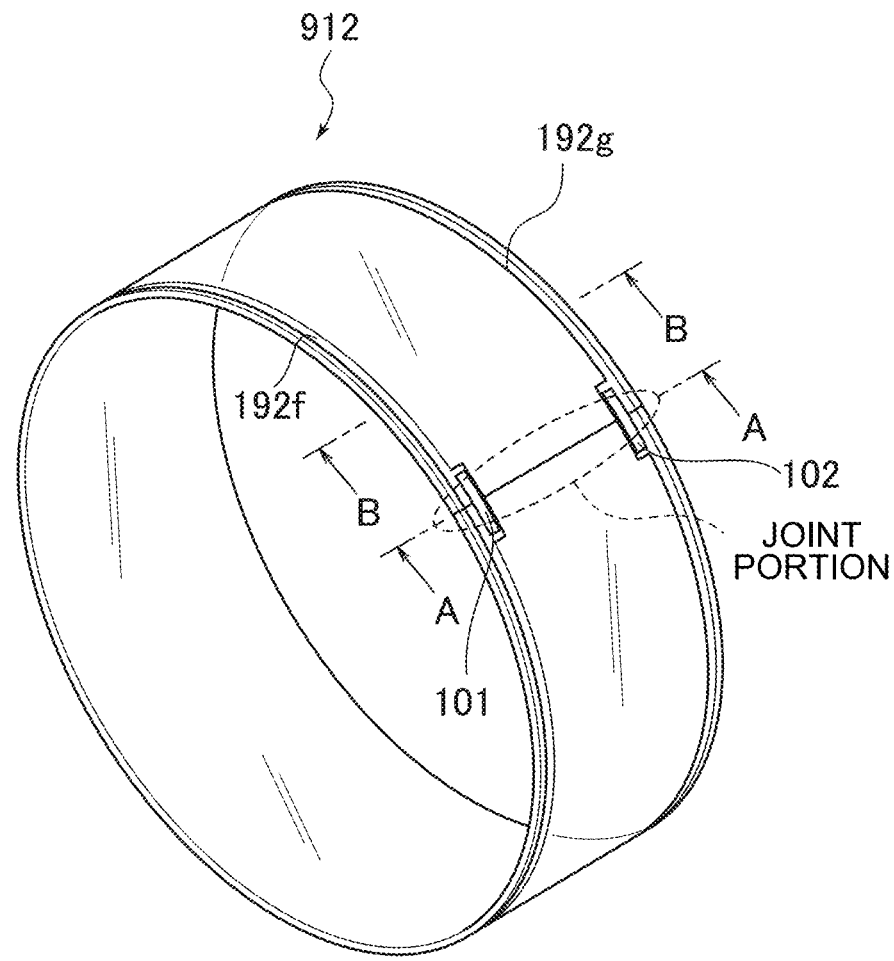
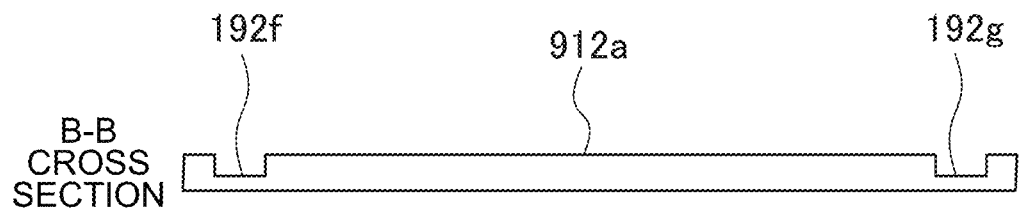
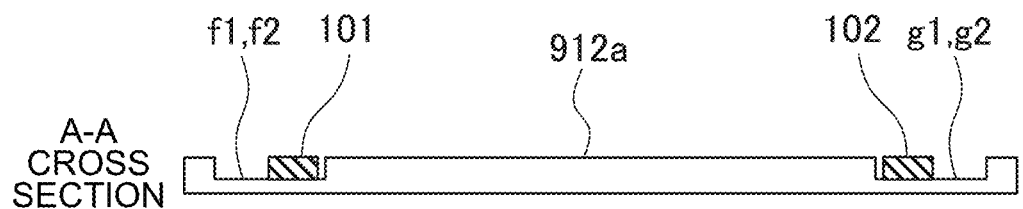

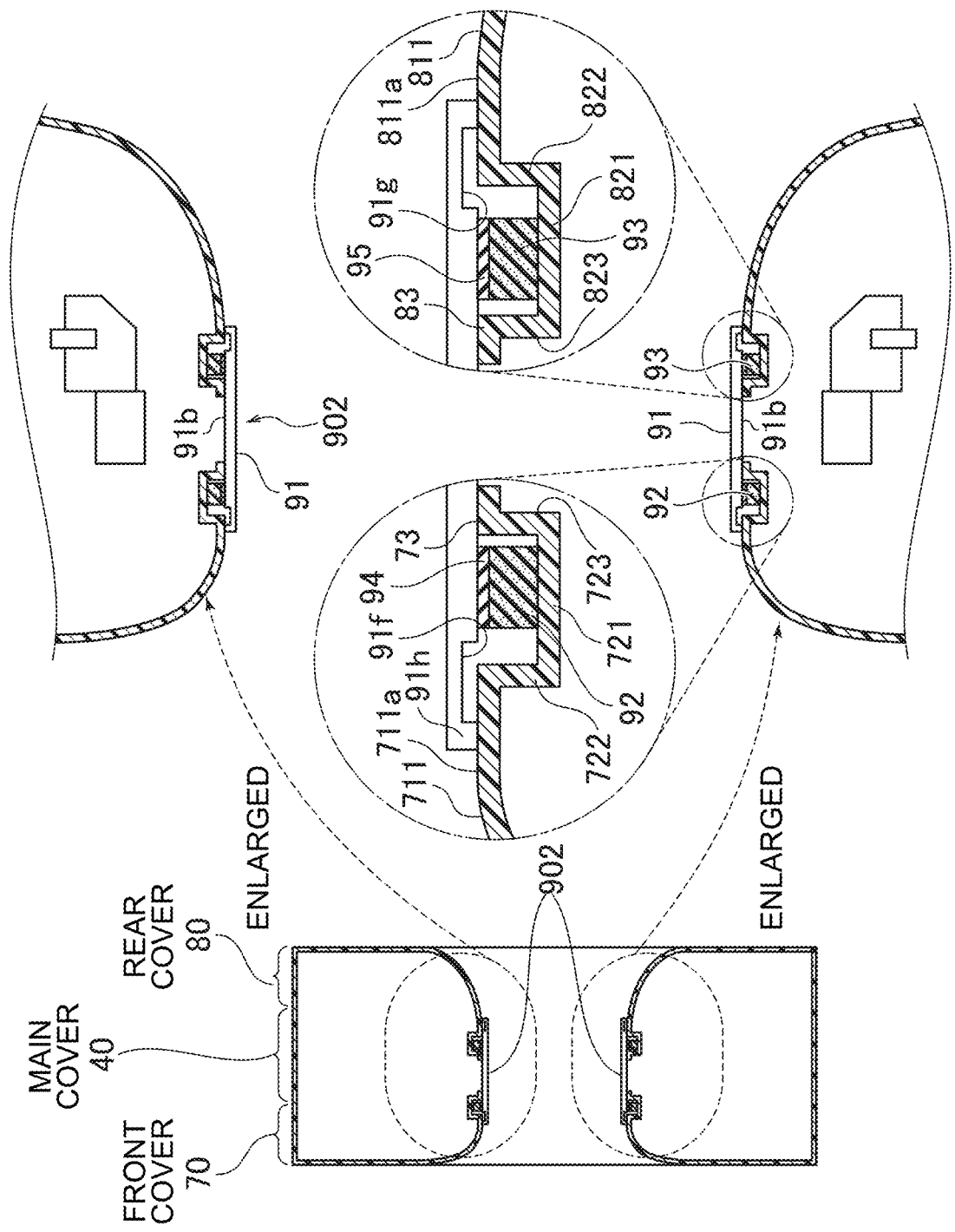

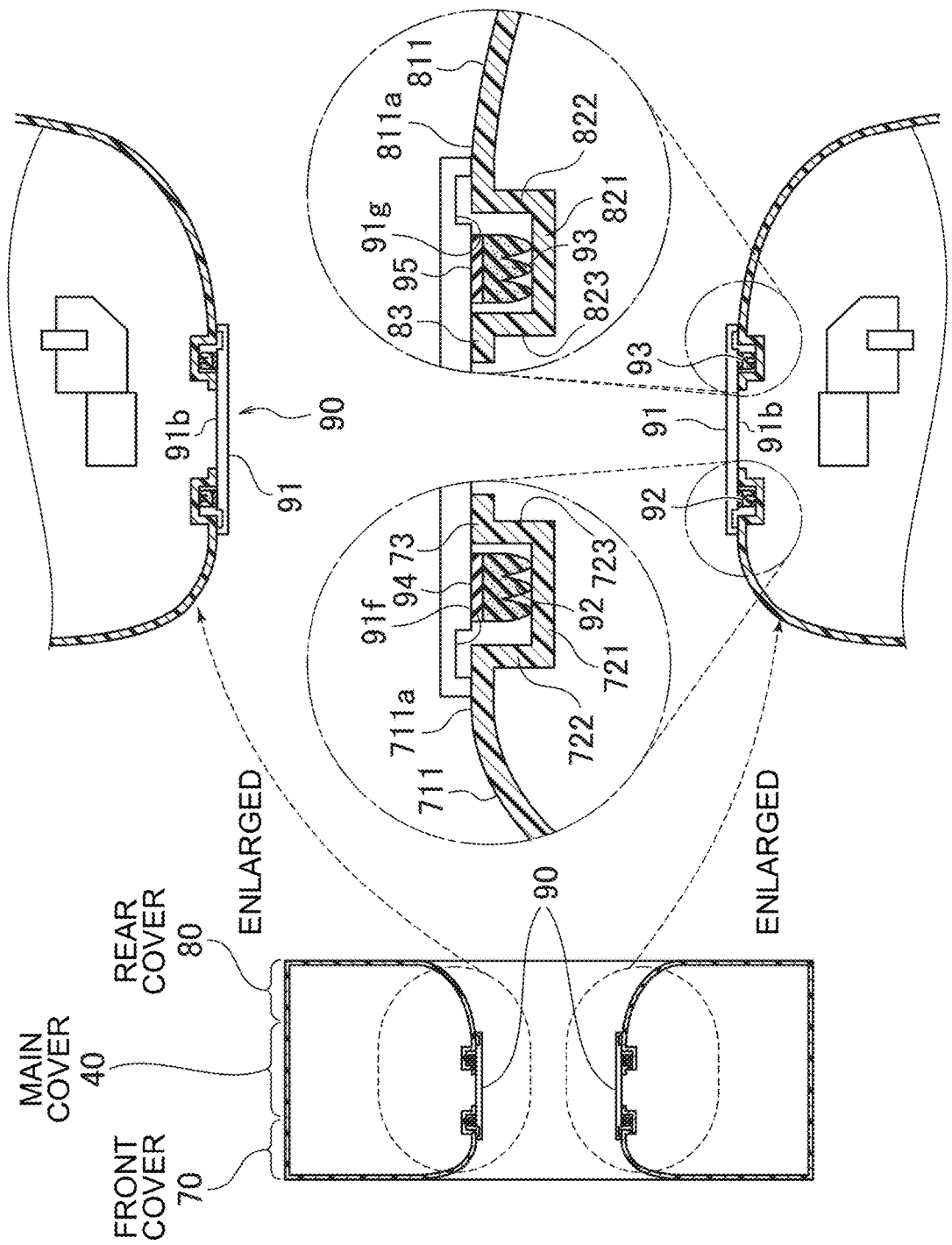

ND MEDICAL
GANTRY HOUSING, AND MEDICAL APPARATUS

FIELD OF THE INVENTION

The present invention relates to a gantry housing, and a medical apparatus comprising the gantry housing.

BACKGROUND

X-ray CT apparatuses are known as medical apparatuses for non-invasively capturing an image of the inside of a subject to be examined. X-ray CT apparatuses are widely used in medical institutions such as hospitals because of their capability of imaging body parts to be imaged in a short period of time.

An X-ray CT apparatus comprises a gantry having a bore through which a medical patient is carried. The gantry incorporates therein an X-ray tube so that X-rays are detected while rotating the X-ray tube, and an image of a patient can be reconstructed based on data of the detected X-rays.

The X-ray CT apparatus is also provided in an interior wall of its gantry with a scan window formed of an X-ray transparent material in order that X-rays emitted from the X-ray tube can pass through the interior wall of the gantry for detection by a detector. The scan window is constructed to be removably fitted in a cover of the gantry to allow quick maintenance of the inside of the gantry. An example of the scan window is disclosed in Patent Document 1.

PRIOR-ART REFERENCE

Patent Document

[Patent Document 1] Japanese Patent TOKUHYO 2016-530921

SUMMARY OF THE INVENTION

Problems to be Solved by the Invention

In recent years, it is desired in X-ray CT apparatuses to increase the inner diameter of the bore for accommodating imaging of patients with a large body size, and also for reserving a wide work area around a patient. To increase the inner diameter of the bore, however, it is generally necessary to bring the interior wall of a gantry cover (housing) closer to rotating elements (such as the X-ray tube, detector, etc.) incorporated in the gantry, and therefore, the distance between the gantry cover (housing) and rotating elements (such as the X-ray tube, detector, etc.) is decreased. Accordingly, a larger inner diameter of the bore may disadvantageously lead to an accident that the gantry housing comes into contact with the rotating elements in the case that the housing is deformed by an external force (e.g., a force generated by rotation of the rotating elements).

Moreover, when fitting the scan window in the cover of the bore, it is necessary to prevent any liquid (e.g., a contrast medium and/or patient's blood) from penetrating to the inside of the gantry through a gap between the cover of the bore and the scan window. Therefore, to prevent liquid penetration to the inside of the gantry, a commonly known scan window comprises an elastic member tightly attached to a wall surface of the cover. Since the elastic member is capable of filling the gap between the cover of the bore and the scan window, liquid penetration to the inside of the gantry can be prevented. However, when an external force is applied to the scan window, the elastic member is compressed by the external force. With the elastic member being compressed, the thickness of the elastic member is reduced, so that the reduction of the thickness of the elastic member directly causes the scan window to come closer to the rotating elements. Accordingly, compression of the elastic member may be a cause that brings the gantry housing into contact with the rotating elements (such as the X-ray tube, detector, etc.).

Accordingly, it is demanded to reduce deformation of a gantry housing while reducing the risk of liquid penetration to the inside of the gantry.

Means for Solving the Problems

The present invention, in its first aspect, is a gantry housing in which an X-ray tube rotating around a specific axis is housed, said housing comprising:

a first cover constituting a portion of a front surface of said housing, said first cover having a first wall surface for defining a first opening forming space in which a subject to be examined can be moved;

a second cover constituting a portion of a back surface of said housing, said second cover having a second wall surface for defining a second opening forming the space in which said subject can be moved; and a scan window constructed to be X-ray transparent, said scan window being attached to said first cover and second cover along a path of rotation of said X-ray tube, wherein said scan window has:

a window member having an inner surface for defining a third opening between said first opening and said second opening, for forming the space in which said subject can be moved, and an outer surface for defining space for movement through which said X-ray tube can be moved along said path of rotation, said window member including an X-ray transparent portion;

a first elastic member provided on a side of an outer surface of said window member, for preventing liquid penetration to an inside of said gantry; and a second elastic member provided on the side of the outer surface of said window member, for preventing liquid penetration to the inside of said gantry, said first cover has:

a first receiving portion in which said first elastic member is disposed, said first receiving portion having a first surface with which said first elastic member is in contact; and a first reinforcing portion for reducing deformation of said window member, said first reinforcing portion supporting said window member from the side of the outer surface of said window member, and said second cover has:

a second receiving portion in which said second elastic member is disposed, said second receiving portion having a second surface with which said second elastic member is in contact; and a second reinforcing portion for reducing deformation of said window member, said second reinforcing portion supporting said window member from the side of the outer surface of said window member.

The present invention, in its second aspect, is a medical apparatus comprising the gantry housing in the first aspect.

Effects of the Invention

The gantry housing has first and second receiving portions in which first and second elastic members of the scan window are disposed. Since the first and second receiving portions have respective surfaces with which the first and second elastic members are in contact, the risk of liquid penetrating to the inside of the gantry from the outside of the gantry can be reduced.

Moreover, the gantry housing has first and second reinforcing portions for preventing deformation of a window member of the scan window. The first and second reinforcing portions support the window member from the side of the outer surface of the window member. Therefore, when a force that may cause deformation of the window member is applied to the window member, the first and second reinforcing portions support the window member, so that deformation of the window member can be substantially reduced.

BRIEF DESCRIPTION OF THE DRAWINGS

FIG. 33 A perspective view and an A-A cross-sectional view of the PC sheet 91.
FIG. 36 A perspective view of the PC sheet.
FIG. 37 A view showing a state in which the PC sheet 91 is joined with elastic members 92 and 93.
FIG. 38 A perspective view showing the PC sheet joined with a lining member 101.
FIG. 40 A perspective view of the PC sheet.
FIG. 41 A perspective view showing the PC sheet joined with the lining member 101.
FIG. 47 An explanatory view of a scan window 902 in an eighth embodiment.
FIG. 48 A view showing elastic members used in a ninth embodiment.

EMBODIMENTS FOR CARRYING OUT THE INVENTION

Now embodiments for carrying out the invention will be described; however, the present invention is not limited to these embodiments.

Figure 1:
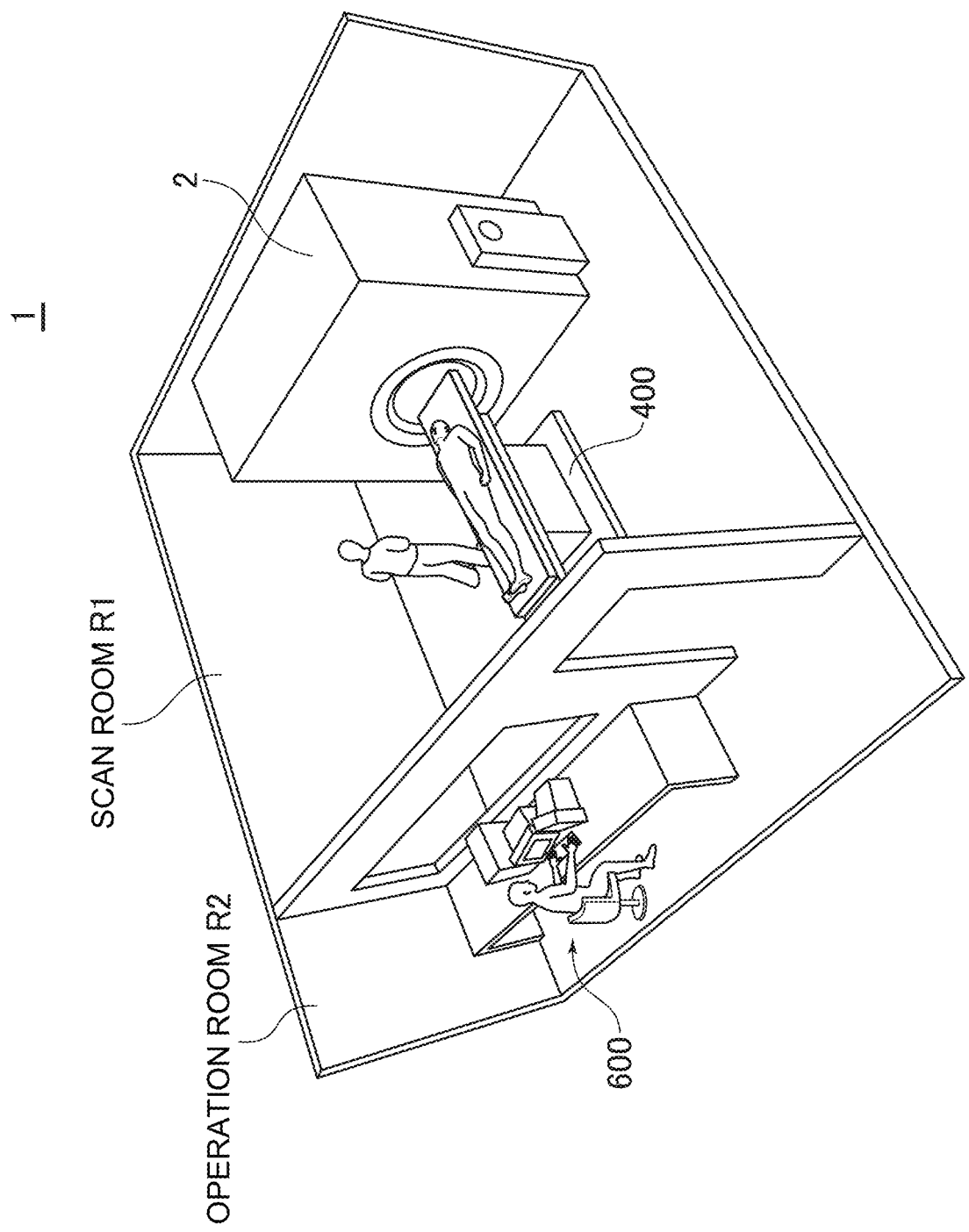
FIG. 1 An external view of an X-ray CT apparatus in a first embodiment.

FIG. 1 is an external view of an X-ray CT apparatus in a first embodiment.

As shown in FIG. 1, an X-ray CT apparatus 1 comprises a gantry 2, a table 400, and an operation console 600.

The gantry 2 and table 400 are installed in a scan room R1, while the operation console 6 is installed in an operation room R2.

Now the gantry 2 will be described.

Figure 2:
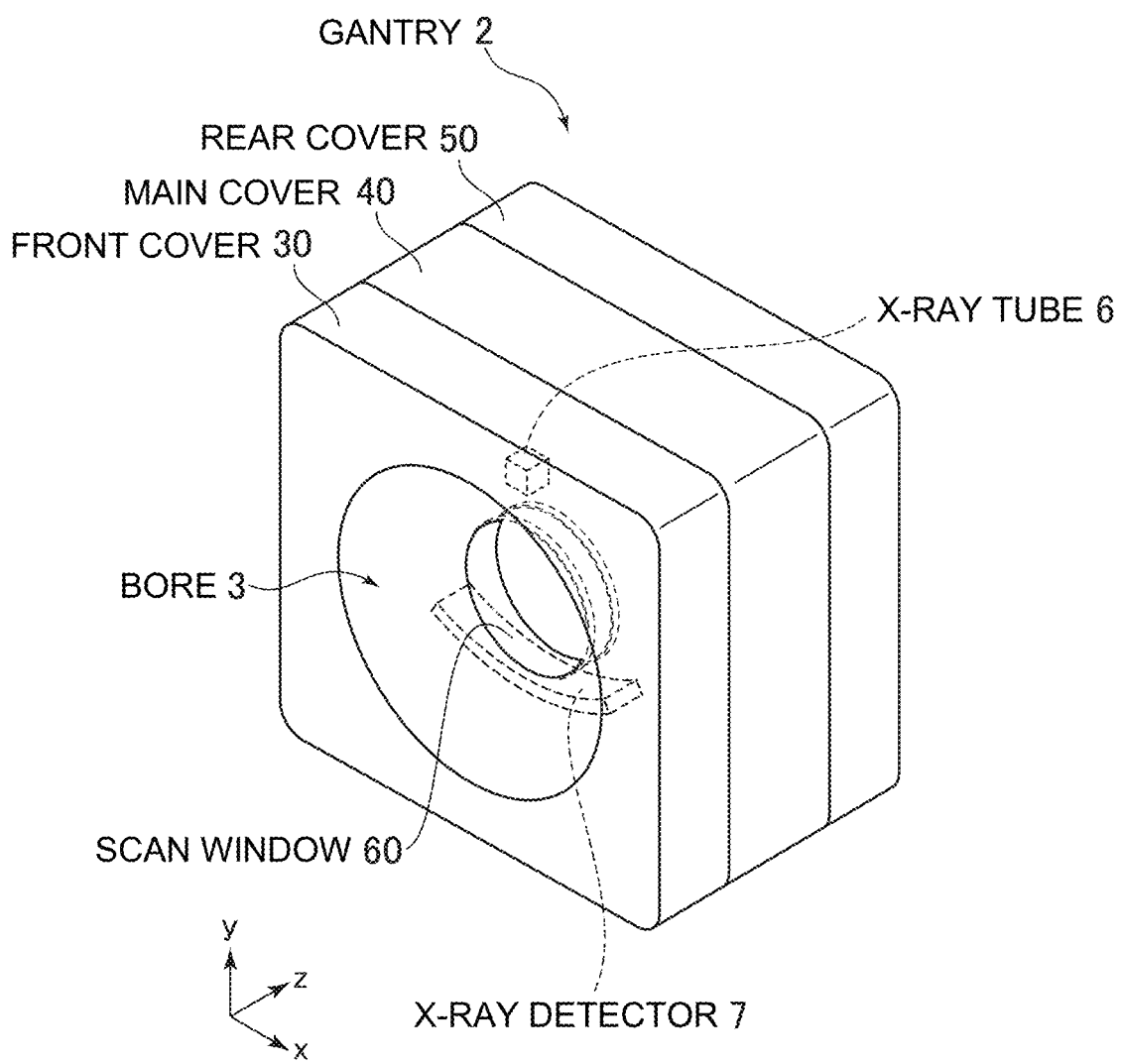
FIG. 2 A perspective view of a gantry 2.
Figure 3:
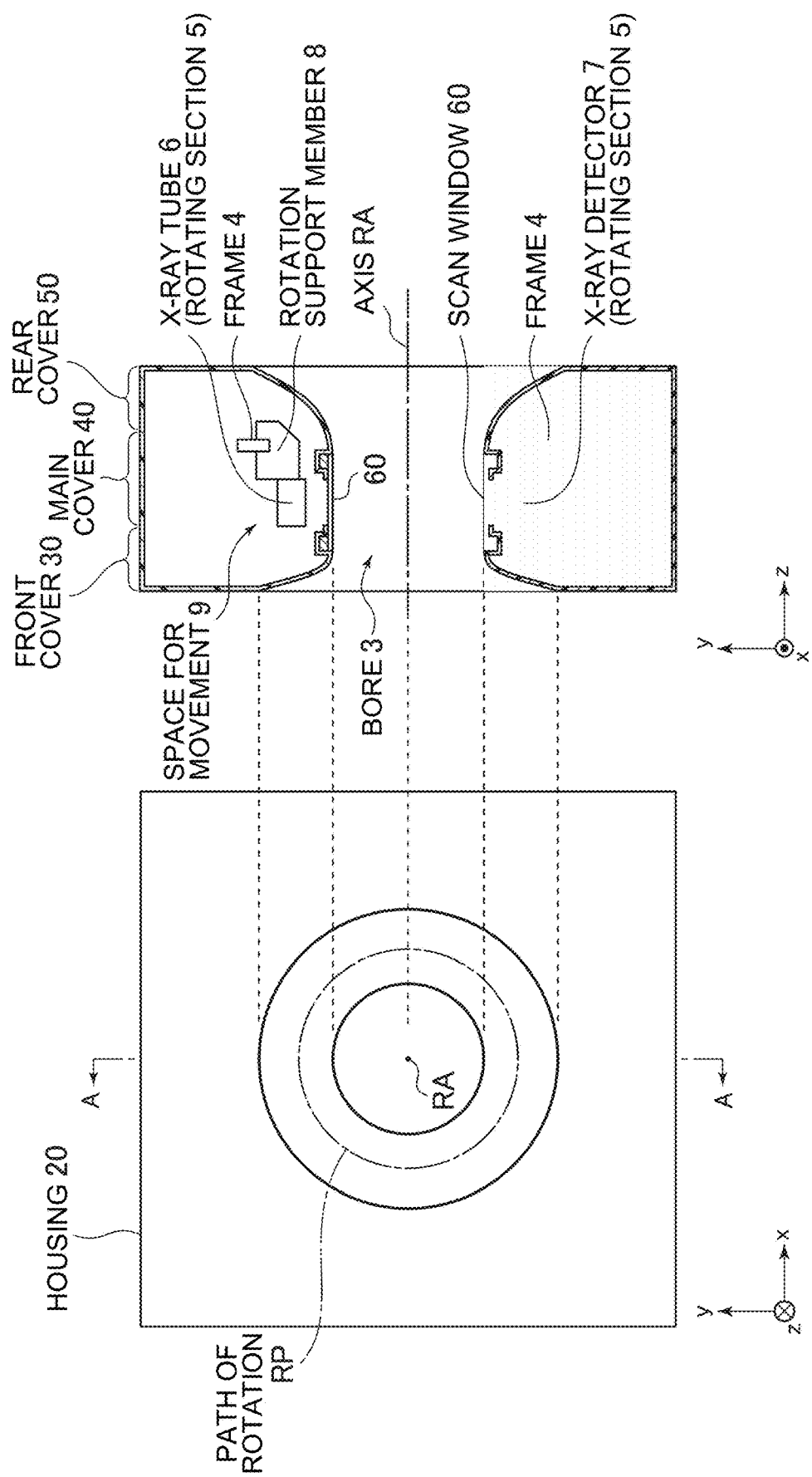
FIG. 3 A front elevational view and an A-A cross-sectional view of the gantry 2.

FIG. 2 is a perspective view of the gantry 2, and FIG. 3 illustrates a front elevational view and an A-A cross-sectional view of the gantry 2.

The gantry 2 has a bore 3 representing space through which a subject to be examined is carried.

The gantry 2 is provided therein with a frame 4, as shown in FIG. 3. It should be noted that the frame 4 is not wholly depicted and only part thereof is shown. The gantry 2 is also provided therein with a rotating section 5 that rotates around an axis RA, which lies in a z-direction. The rotating section 5 has rotating elements including an X-ray tube 6 and an X-ray detector 7. It should be noted that the z-direction corresponds to a body-axis direction, a y-direction corresponds to a vertical direction, and an x-direction corresponds to a direction orthogonal to the z- and y-directions.

The frame 4 is attached with a rotation support member 8 for supporting the rotating section 5. The X-ray tube 6 and X-ray detector 7 are rotatably mounted to the rotation support member 8. The rotating section 5 rotates along a path of rotation RP around the axis RA.

A housing 20 is constructed to cover the members disposed in the inside of the gantry 2. Moreover, the housing 20 forms space 9 for movement in which the rotating section 5 is capable of moving along the path of rotation RP in the space surrounded by the housing 20.

In imaging, the subject is carried into the bore 3, whereupon X-rays are emitted from the X-ray tube 6, and the X-ray detector 7 detects the X-rays. The detected X-rays are processed by a DAS (Data Acquisition System), and are collected as X-ray data. Based on the X-ray data, an image is then produced.

Figure 4:
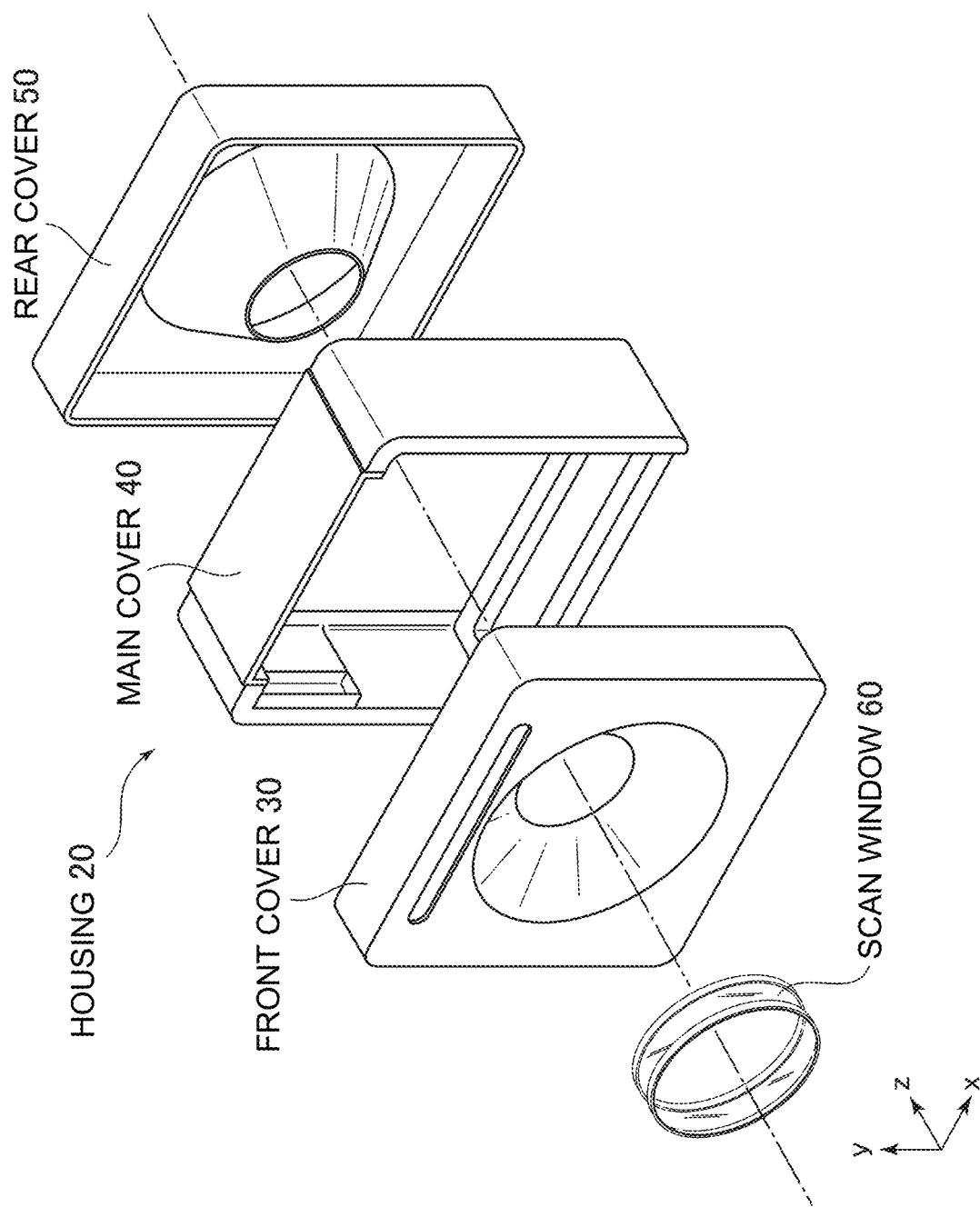
FIG. 4 An exploded perspective view of a housing 20 of the gantry 2.

FIG. 4 is an exploded perspective view of the housing 20 of the gantry 2.

The housing 20 has a front cover 30, a main cover 40, a rear cover 50, and a scan window 60.

The main cover 40 is a cover provided between the front cover 30 and rear cover 50. The front cover 30 is fixed on the side of a front surface of the main cover 40, while the rear cover 50 is fixed on the side of a back surface of the main cover 40.

Next, a structure of the front cover 30 and rear cover 50 will be described referring to FIGS. 5 to 8.

Figure 5:
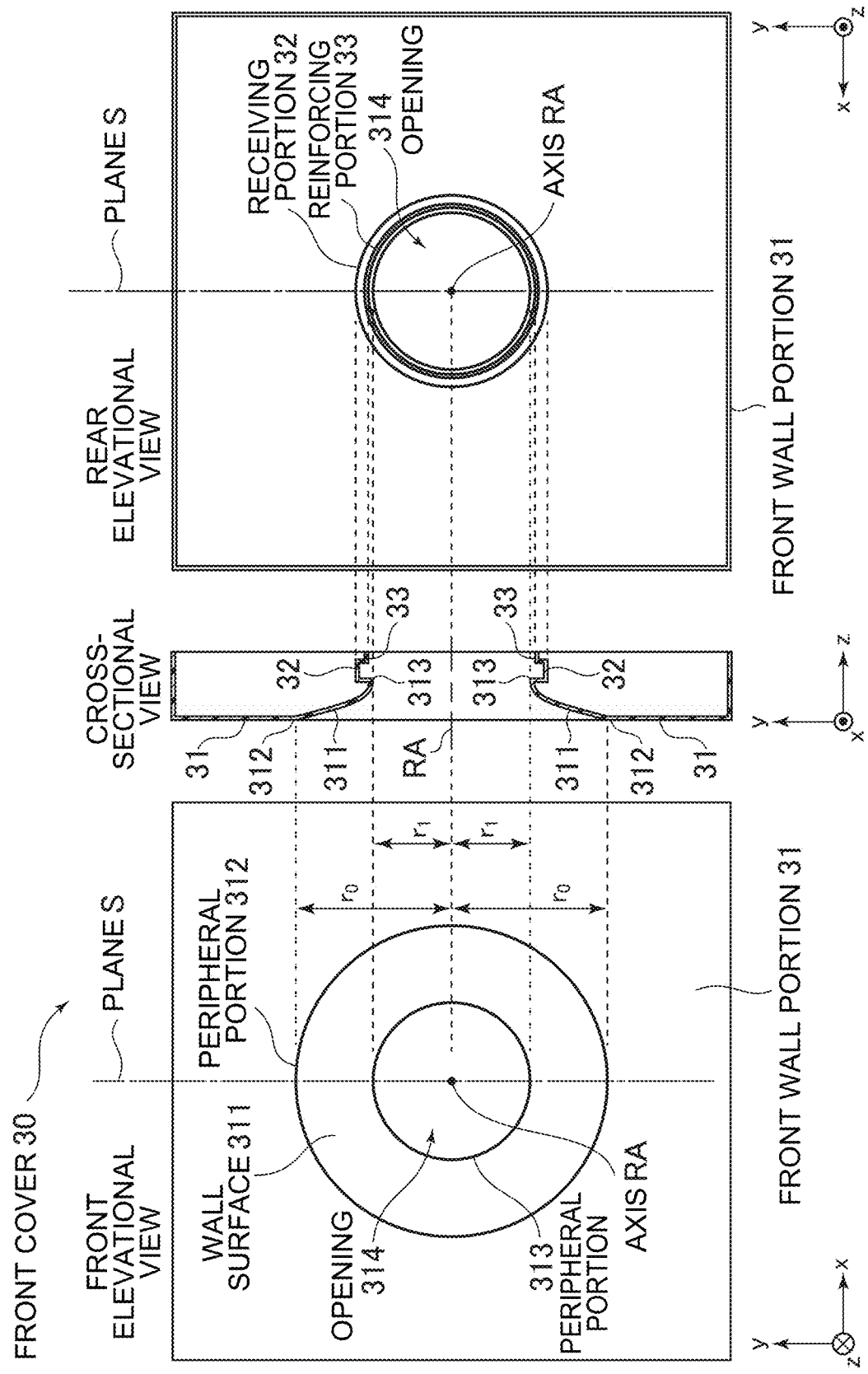
FIG. 5 An explanatory view of a front cover 30.

FIG. 5 is an explanatory view of the front cover 30.

In FIG. 5 are shown a front elevational view, a cross-sectional view, and a rear elevational view of the front cover 30. It should be noted that the cross-sectional view of the front cover 30 represents a cross-sectional view in a plane S containing the axis RA and lying in parallel with a yz-plane.

The front cover 30 is a cover constituting a portion of a front surface of the housing 20. The front cover 30 has a front wall portion 31, a receiving portion 32, and a reinforcing portion 33. The front wall portion 31, receiving portion 32, and reinforcing portion 33 are formed integrally with one another.

The front wall portion 31 has a wall surface 311. The wall surface 311 has in an xy-plane (see the front elevational view in FIG. 5) a peripheral portion 312 lying along the circumference of a circle of radius r0 around the axis RA, and a peripheral portion 313 lying along the circumference of a circle of radius r1 around the axis RA. The wall surface 311 defines an opening 314 for forming space in which the subject can be moved. The opening 314 is formed to allow the subject to be moved thereinto.

Next, the receiving portion 32 and reinforcing portion 33 will be described (see FIG. 6).

Figure 6:
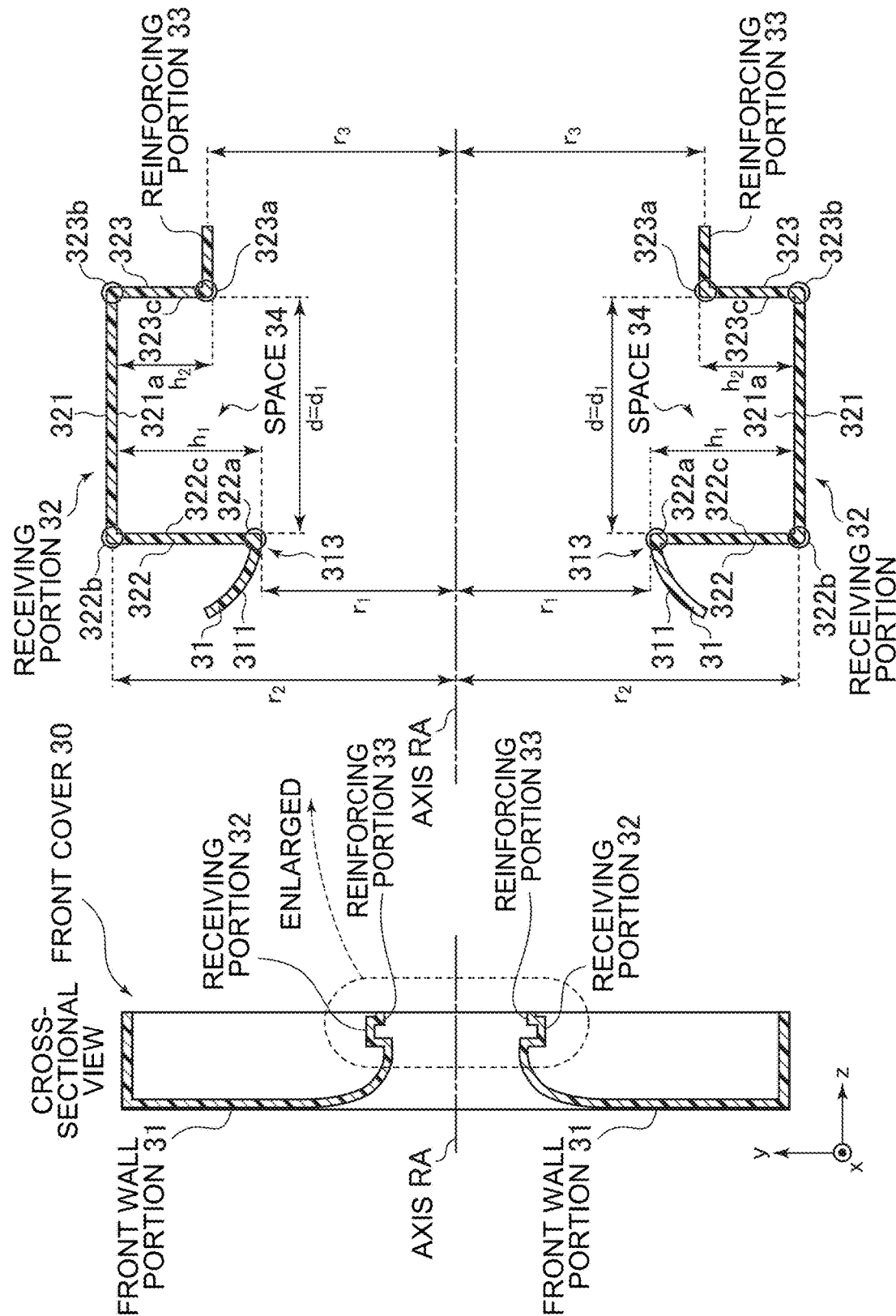
FIG. 6 An explanatory view of a receiving portion 32 and a reinforcing portion 33.

FIG. 6 is an explanatory view of the receiving portion 32 and reinforcing portion 33.

In FIG. 6 are shown the cross-sectional view in FIG. 5, and an enlarged view of the receiving portion 32 and reinforcing portion 33. It should be noted that in FIG. 6, the size of the receiving portion 32 and reinforcing portion 33 is exaggerated relative to the lengths of the radii r1, r2, and r3 in order that the structure of the receiving portion 32 and reinforcing portion 33 is visually comprehensible.

The receiving portion 32 is a member for receiving an elastic member 62 described later (see FIG. 11). The way how the receiving portion 32 receives the elastic member 62 will be described later. The receiving portion 32 is formed integrally with the peripheral portion 313 of the front wall portion 31. The receiving portion 32 has a base portion 321, a first side portion 322, and a second side portion 323.

The base portion 321 has a ring shape extending along the circumference of a circle of radius r2 around the axis RA.

The first side portion 322 has a ring shape extending along the peripheral portion 313 of the front wall portion 31. The first side portion 322 has an inner edge portion 322a extending along the circumference of a circle of radius r1 around the axis RA, and an outer edge portion 322b extending along the circumference of a circle of radius r2 around the axis RA. The inner edge portion 322a is formed integrally with the peripheral portion 313 of the front wall portion 31, while the outer edge portion 322b is formed integrally with the base portion 321.

The second side portion 323 is formed to face the first side portion 322 in the z-direction. The second side portion 323 has an inner edge portion 323a extending along the circumference of a circle of radius r3 around the axis RA, and an outer edge portion 323b extending along the circumference of a circle of radius r2 around the axis RA. The outer edge portion 323b is formed integrally with the base portion 321.

The base portion 321 has an interior wall surface 321a, the first side portion 322 has an interior wall surface 322c, and the second side portion 323 has an interior wall surface 323c. A height h of the interior wall surface 322c is set as h=h1, a height h of the interior wall surface 323c is set as h=h2, and a distance d between the interior wall surfaces 322c and 323c is set as d=d1.

Space 34 surrounded by these interior wall surfaces 321a, 322c, and 323c is used as space in which the elastic member 62 of the scan window 60 described later (see FIG. 11) is to be disposed.

Next, the reinforcing portion 33 will be described.

The reinforcing portion 33 is formed to extend along the circumference of a circle of radius r3 around the axis RA. The reinforcing portion 33 is formed to protrude in a direction away from the first side portion 322 with respect to the second side portion 323. The reinforcing portion 33 is formed integrally with the inner edge portion 323a of the second side portion 323. The reinforcing portion 33 is for reinforcing a PC sheet 61 of the scan window 60 described later (see FIG. 11), so that deformation of the PC sheet 61 is reduced. The way how the reinforcing portion 33 reinforces the PC sheet 61 will be described later.

The front cover 30 has the thus-constructed receiving portion 32 and reinforcing portion 33. The front cover 30 may be molded using a die, for example.

Next, the rear cover 50 will be described.

Figure 7:
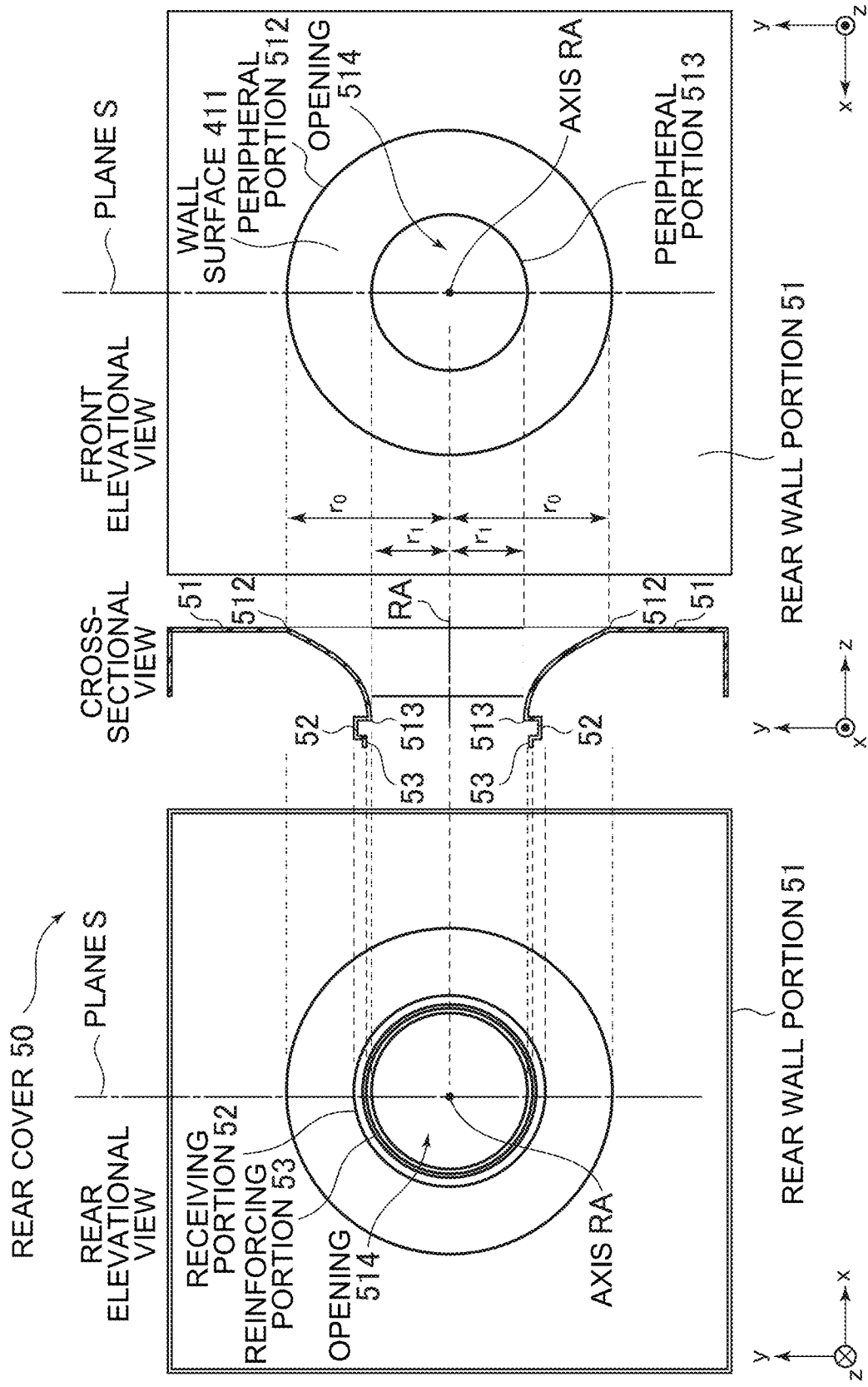
FIG. 7 An explanatory view of a rear cover 50.

FIG. 7 is an explanatory view of the rear cover 50.

In FIG. 7 are shown a front elevational view, a cross-sectional view, and a rear elevational view of the rear cover 50. It should be noted that the cross-sectional view of the rear cover 50 represents a cross-sectional view in the plane S containing the axis RA and lying in parallel with the yz-plane.

The rear cover 50 is a cover constituting a portion of a back surface of the housing 20. The rear cover 50 has a rear wall portion 51, a receiving portion 52, and a reinforcing portion 53. The rear wall portion 51, receiving portion 52, and reinforcing portion 53 are formed integrally with one another.

The rear wall portion 51 has a wall surface 511. The wall surface 511 has in the xy-plane (see the front elevational view in FIG. 7) a peripheral portion 512 lying along the circumference of a circle of radius r0 around the axis RA, and a peripheral portion 513 lying along the circumference of a circle of radius r1 around the axis RA. The wall surface 511 defines an opening 514 for forming space in which the subject can be moved. The opening 514 is formed to allow the subject to be moved thereinto.

Next, the receiving portion 52 and reinforcing portion 53 will be described (see FIG. 8).

Figure 8:
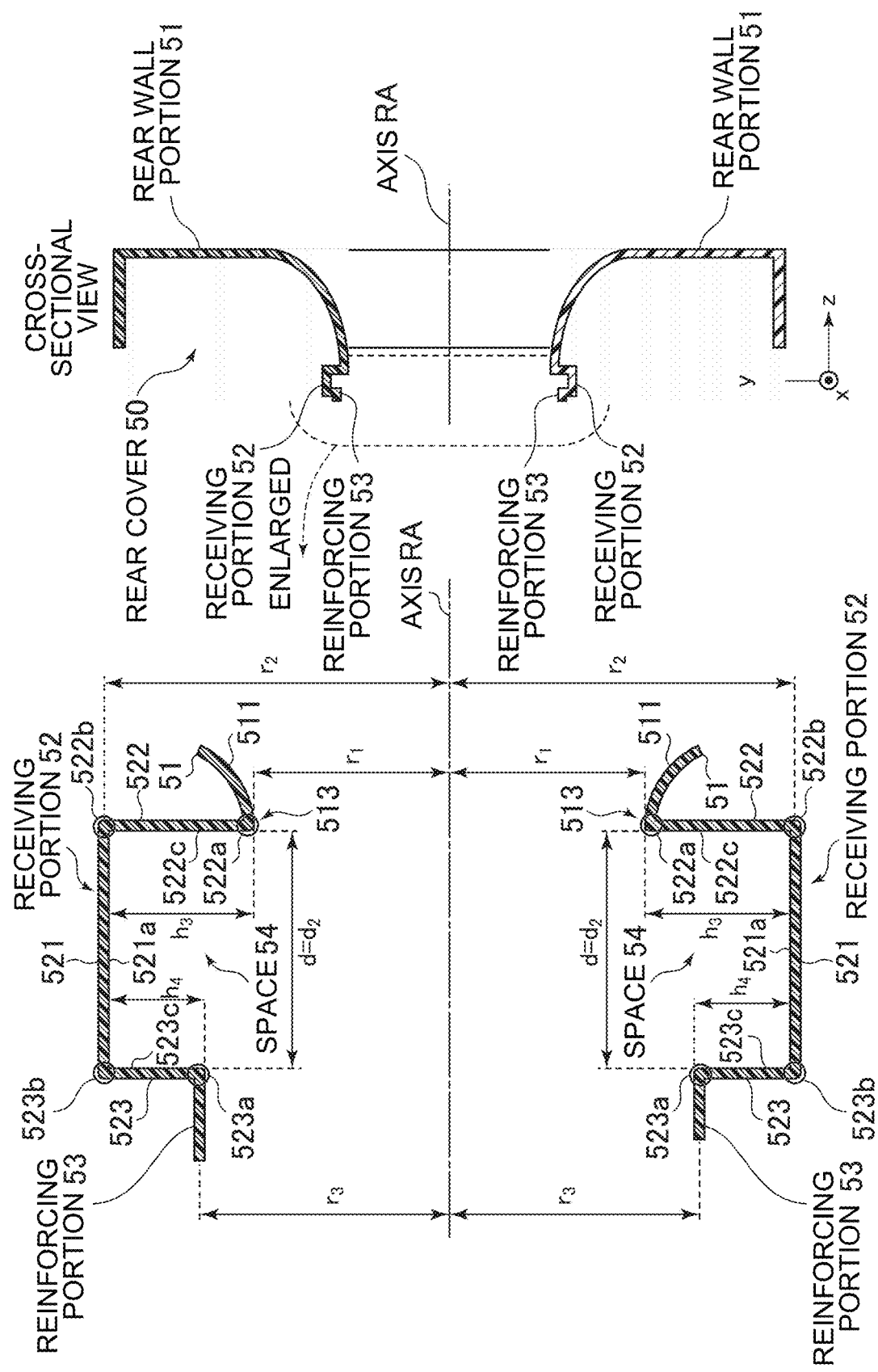
FIG. 8 An explanatory view of a receiving portion 52 and a reinforcing portion 53.

FIG. 8 is an explanatory view of the receiving portion 52 and reinforcing portion 53.

In FIG. 8 are shown the cross-sectional view in FIG. 7, and an enlarged view of the receiving portion 52 and reinforcing portion 53. It should be noted that in FIG. 8, the size of the receiving portion 52 and reinforcing portion 53 is exaggerated relative to the lengths of the radii r1, r2, and r3 in order that the structure of the receiving portion 52 and reinforcing portion 53 is visually comprehensible.

The receiving portion 52 is a member for receiving an elastic member 63 described later (see FIG. 11). The way how the receiving portion 52 receives the elastic member 63 will be described later. The receiving portion 52 is formed integrally with the peripheral portion 513 of the rear wall portion 51. The receiving portion 52 has a base portion 521, a third side portion 522, and a fourth side portion 523.

The base portion 521 has a ring shape extending along the circumference of a circle of radius r2 around the axis RA.

The third side portion 522 has a ring shape extending along the peripheral portion 513 of the rear wall portion 51. The third side portion 522 has an inner edge portion 522a extending along the circumference of a circle of radius r1 around the axis RA, and an outer edge portion 522b extending along the circumference of a circle of radius r2 around the axis RA. The inner edge portion 522a is formed integrally with the peripheral portion 513 of the rear wall portion 51, while the outer edge portion 522b is formed integrally with the base portion 521.

The fourth side portion 523 is formed to face the third side portion 522 in the z-direction. The fourth side portion 523 has an inner edge portion 523a extending along the circumference of a circle of radius r3 around the axis RA, and an outer edge portion 523b extending along the circumference of a circle of radius r2 around the axis RA. The outer edge portion 523b is formed integrally with the base portion 521.

The base portion 521 has an interior wall surface 521a, the third side portion 522 has an interior wall surface 522c, and the fourth side portion 523 has an interior wall surface 523c. A height h of the interior wall surface 522c is set as h=h3, a height h of the interior wall surface 523c is set as h=h4, and a distance d between the interior wall surfaces 522c and 523c is set as d=d2.

Space 54 surrounded by these interior wall surfaces 521a, 522c, and 523c is used as space in which the elastic member 63 of the scan window 60 described later (see FIG. 11) is to be disposed.

Next, the reinforcing portion 53 will be described.

The reinforcing portion 53 is formed to extend along the circumference of a circle of radius r3 around the axis RA. The reinforcing portion 53 is formed to protrude in a direction away from the third side portion 522 with respect to the fourth side portion 523. The reinforcing portion 53 is formed integrally with the inner edge portion 523a of the fourth side portion 523. The reinforcing portion 53 is for reinforcing the PC sheet 61 of the scan window described later (see FIG. 11), so that deformation of the PC sheet 61 is reduced. The way how the reinforcing portion 53 reinforces the PC sheet 61 will be described later.

The rear cover 50 has the thus-constructed receiving portion 52 and reinforcing portion 53. The rear cover 50 may be molded using a die, for example.

Figure 9:
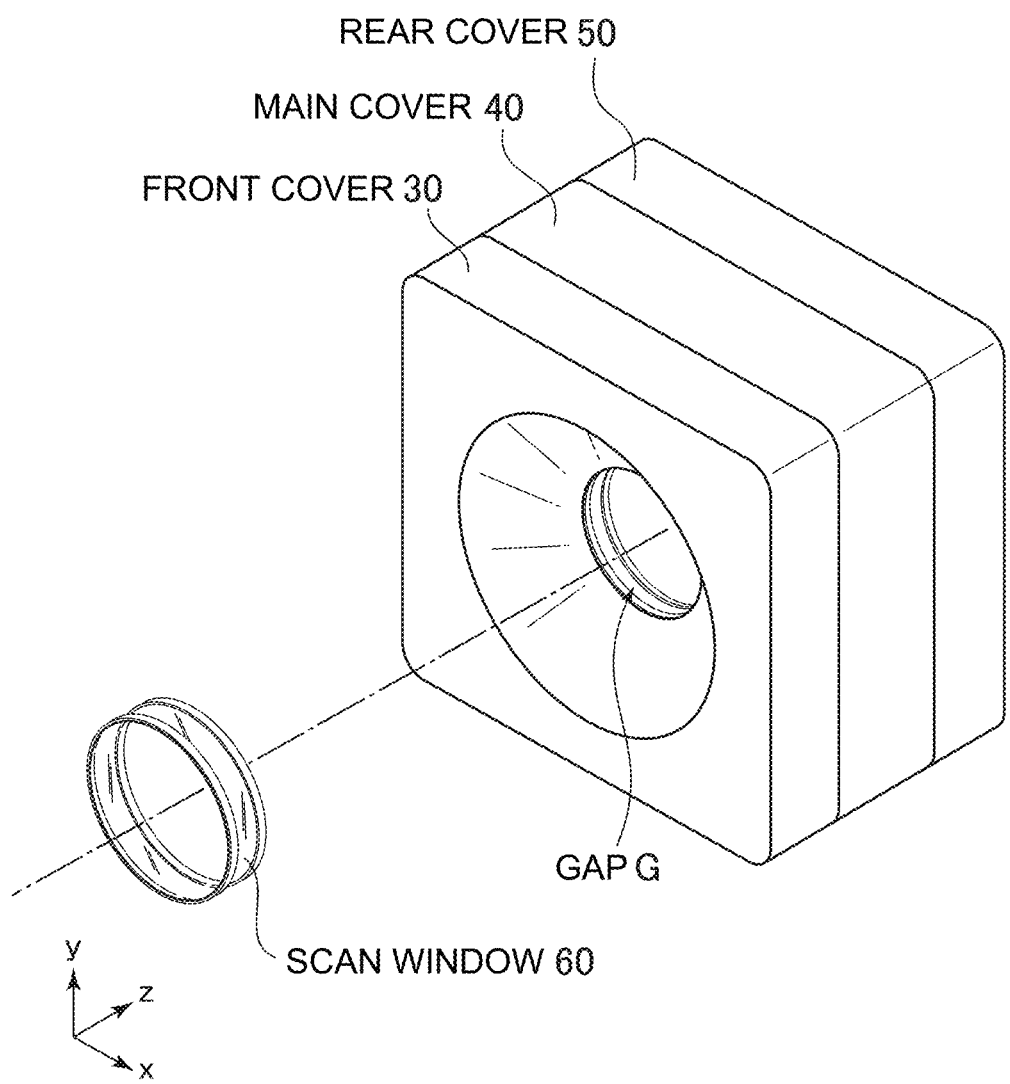
FIG. 9 A perspective view of the front cover 30 and rear cover 50 fixed to a main cover 40.
Figure 10:
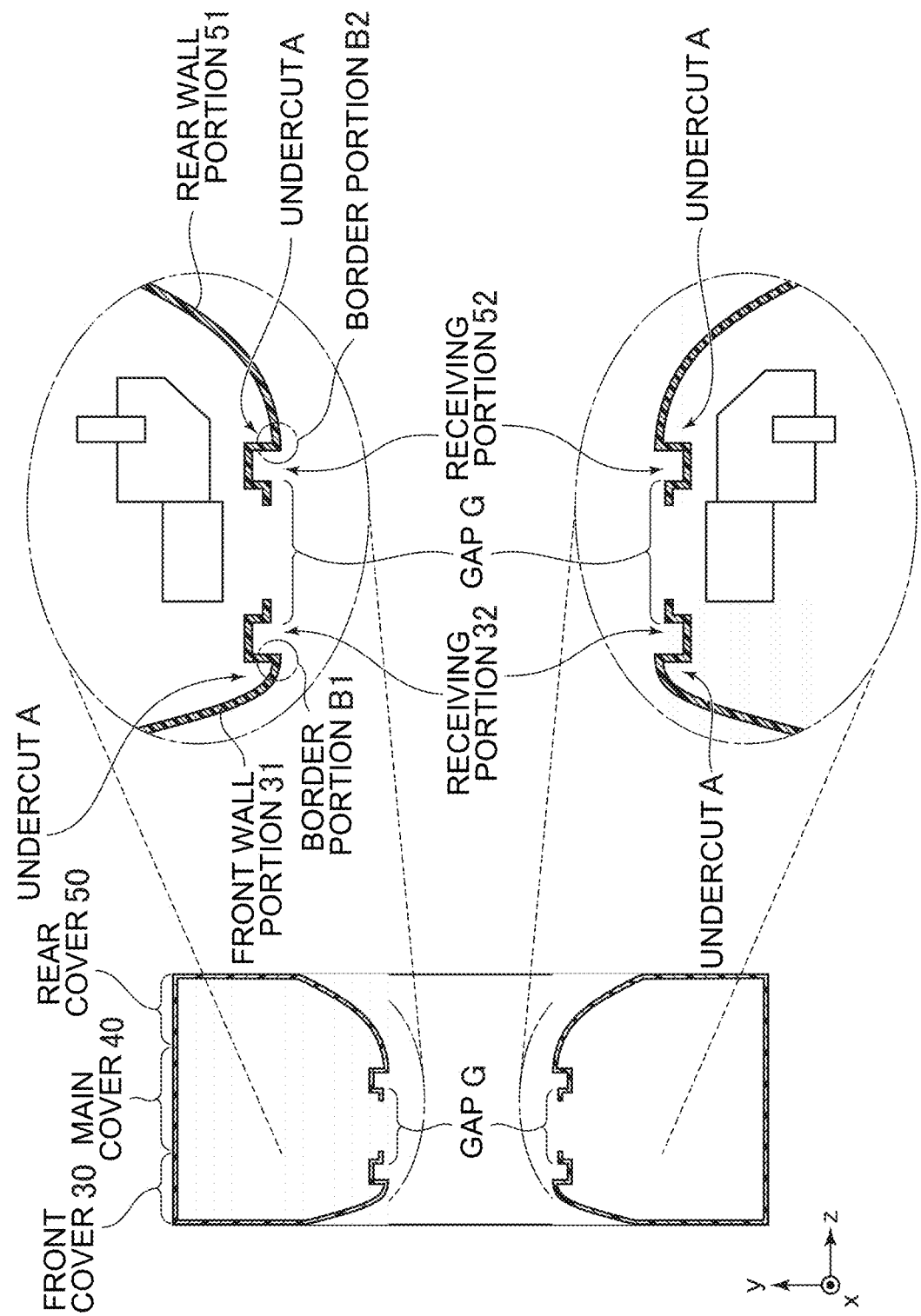
FIG. 10 A cross-sectional view of the front cover 30, main cover 40, and rear cover 50 shown in FIG. 9.

The thus-constructed front cover 30 and rear cover 50 are fixed to the main cover 40 (see FIGS. 9 and 10).

FIGS. 9 and 10 are views showing the front cover 30 fixed on the side of the front surface of the main cover 40, and the rear cover 50 fixed on the side of the back surface of the main cover 40.

FIG. 9 is a perspective view of the front cover 30 and rear cover 50 fixed to a main cover 40, and FIG. 10 is a cross-sectional view of the front cover 30, main cover 40, and rear cover 50 shown in FIG. 9. It should be noted that FIG. 10 represents a cross-sectional view in the plane containing the axis RA and lying in parallel with the yz-plane.

By the front cover 30 and rear cover 50 being fixed to the main cover 40, a gap G is formed between the opening of the front cover 30 and that of the rear cover 50, as shown in FIG. 9.

The scan window 60 is constructed so that it can be fitted in the front cover 30 and rear cover 50 to fill the gap G.

A worker, such as an employee in a manufacturing factory of X-ray CT apparatuses or a field engineer, can manually fit the scan window 60 in the front cover 30 and rear cover 50. The worker can fit the scan window 60 in the front cover 30 and rear cover 50 so as to fill the gap G (see FIGS. 9 and 10), as shown in FIG. 2. Moreover, the worker can manually remove the scan window 60 from the front cover 30 and rear cover 50, as needed.

Next, a structure of the scan window 60 will be described.

Figure 11:
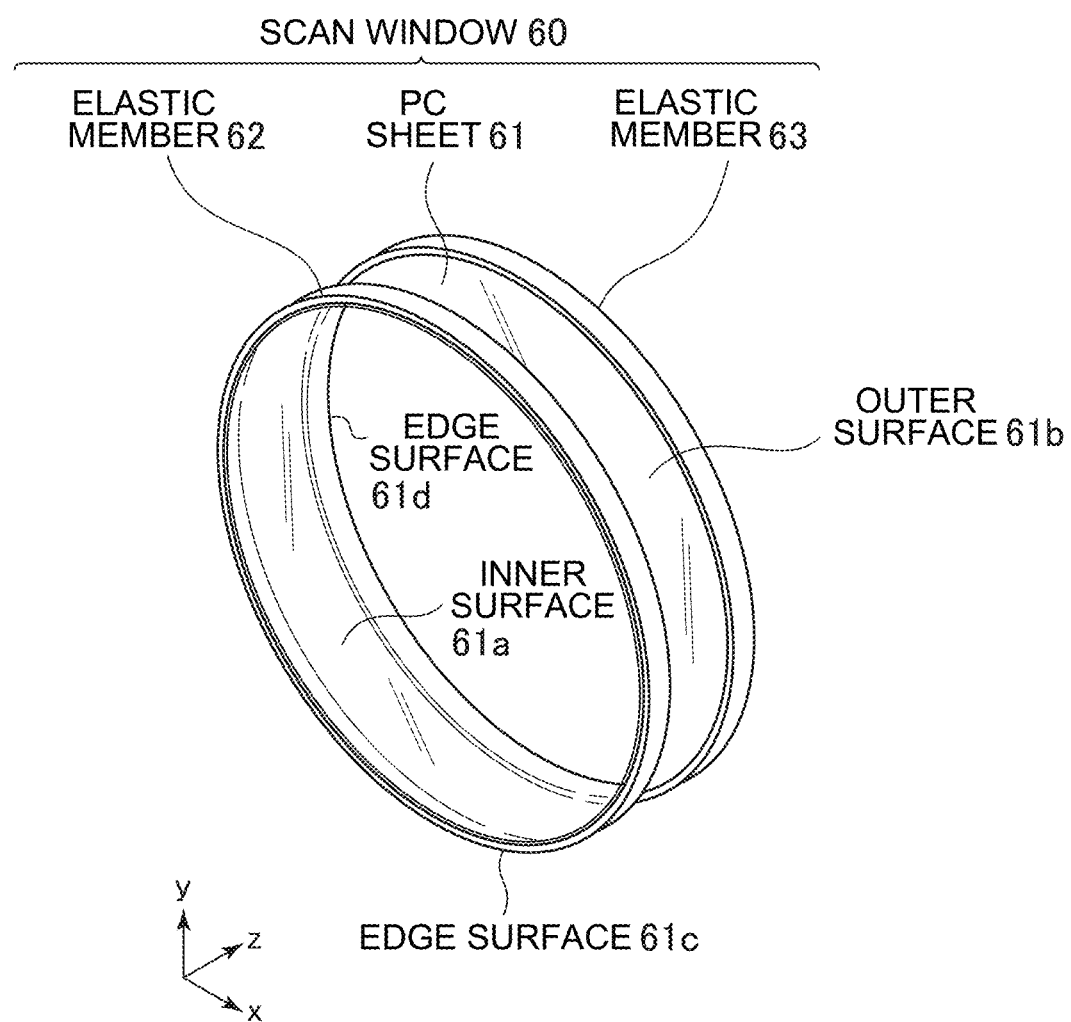
FIG. 11 A perspective view of a scan window 60.
Figure 12:
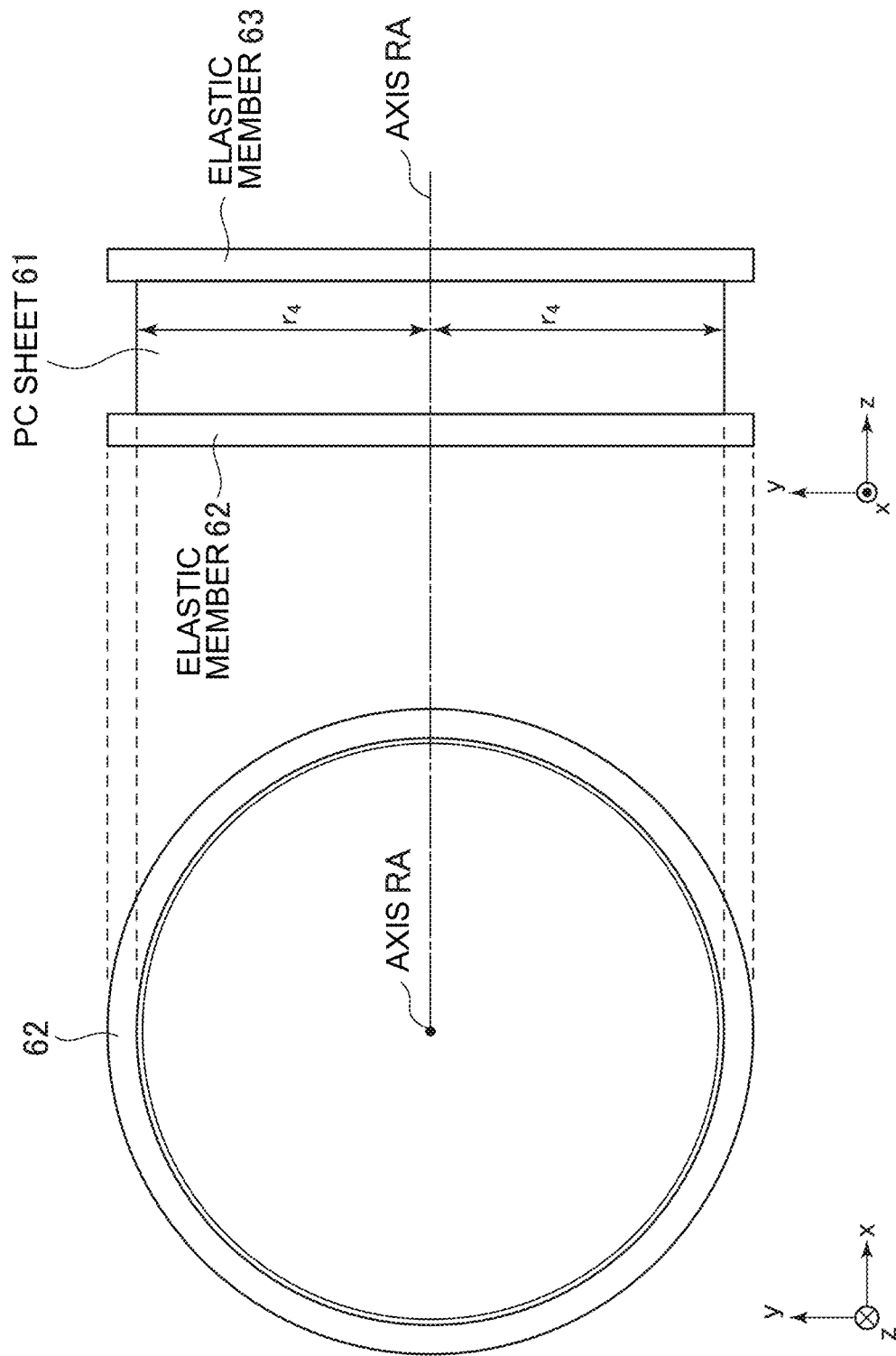
FIG. 12 A front elevational view and a side view of the scan window 60.
Figure 13:
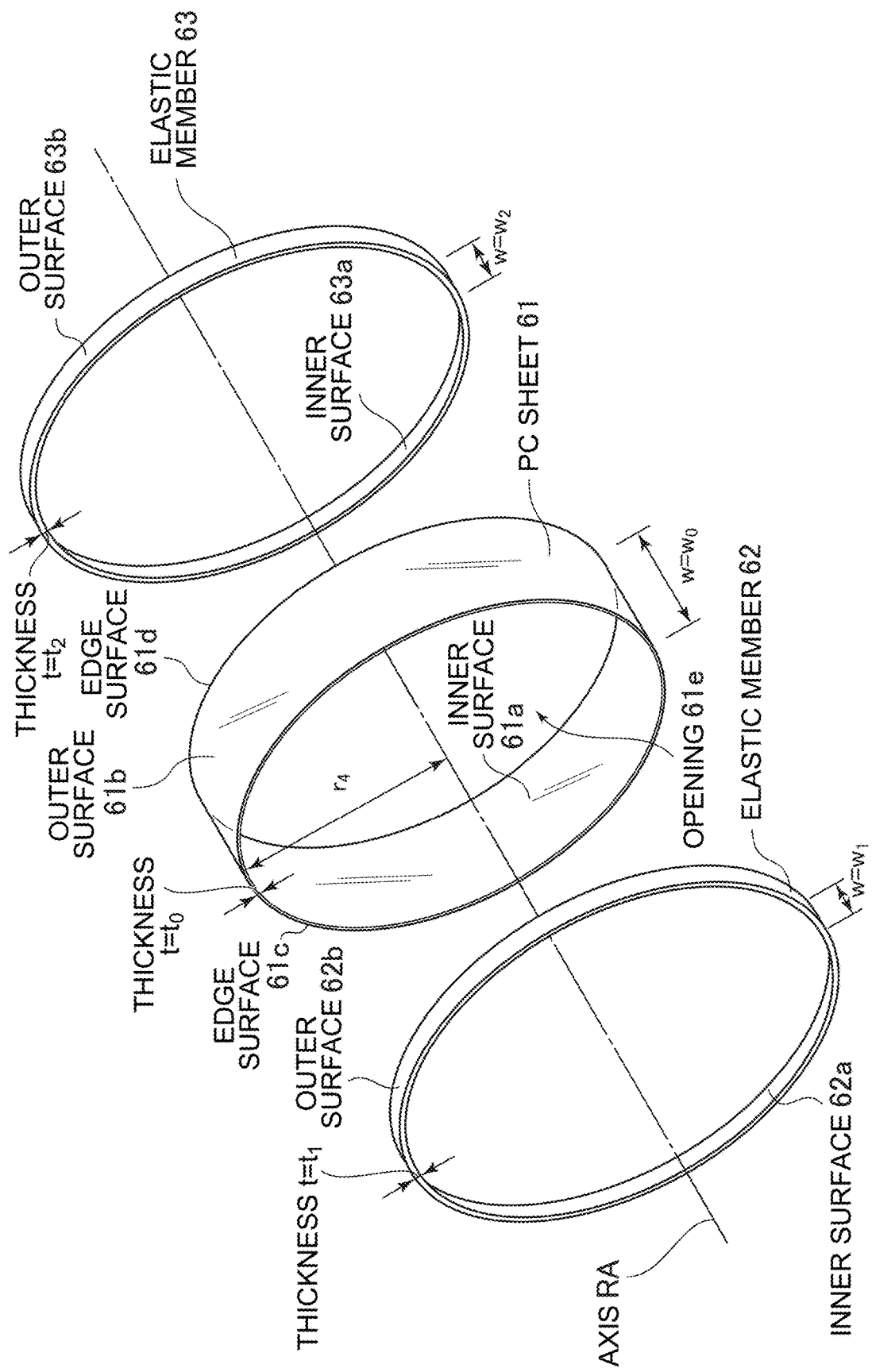
FIG. 13 An exploded perspective view of the scan window 60.

FIGS. 11 to 13 are explanatory views of the scan window 60.

FIG. 11 is a perspective view of the scan window 60, and FIG. 12 illustrates a front elevational view and a side view of the scan window 60.

The scan window 60 has a generally cylindrical shape. Now several components constituting the scan window 60 will be described.

FIG. 13 is an exploded perspective view of the scan window 60.

The scan window 60 has the PC (PolyCarbonate) sheet 61, and elastic members 62 and 63.

The PC sheet 61 is a sheet formed of polycarbonate, which is X-ray transparent and is deformable. The PC sheet 61 is for use as a window member having an X-ray transparent window, and has a ring shape along the circumference of a circle of radius r4 around the axis RA. The radius r4 may be set to a value within a range of 30 to 40 cm, for example. While polycarbonate is used to form an X-ray transparent and deformable sheet in the first embodiment, the X-ray transparent and deformable sheet may be formed of a material different from polycarbonate.

Moreover, the PC sheet 61 is formed to have a thickness t set as t=t0 and a width w in a direction of the axis RA set as w=w0. The thickness t0 may be set to a value within a range of 0.1 to several millimeters, for example, and w0 may be set to a value within a range of 10 to 30 cm, for example.

The PC sheet 61 has an inner surface 61a and an outer surface 61b. The inner surface 61a of the PC sheet 61 defines an opening 61e for forming space in which the subject can be moved. The opening 61e is formed to allow the subject to be moved thereinto. On the other hand, the outer surface 61b of the PC sheet 61 is a surface for defining the space 9 for movement of the rotating section 5 (see FIG. 3). It should be noted that it is also possible to form part of the PC sheet 61 of a material that prevents X-ray transmission in order to limit a z-extent of the X-rays emitted from the X-ray tube 6.

Moreover, the PC sheet 61 has two edge surfaces 61c and 61d facing mutually opposite sides.

Next, the elastic members 62 and 63 will be described.

The elastic member 62 has a ring shape along the edge surface 61c of the PC sheet 61. The elastic member 62 also has an inner surface 62a and an outer surface 62b. The inner surface 62a of the elastic member 62 is used as a joint surface joined to the outer surface 61b of the PC sheet 61. The elastic member 62 is formed to have a thickness t set as t=t1, and a width w set as w=w1. The thickness t1 may be set to a value of several millimeters, for example, and w1 may be set to a value of several to several tens of millimeters, for example. The elastic member 62 is constructed so that it can be fitted into the receiving portion 32 of the front cover 30 (see FIG. 6). The thickness t1 of the elastic member 62 is set to a value slightly larger than the height h2 of the interior wall surface 323c of the receiving portion 32 (see FIG. 6). The width w1 of the elastic member 62 is set to a value slightly smaller than the distance d1 of the receiving portion 32 (see FIG. 6).

Next, the elastic member 63 will be described.

The elastic member 63 has a ring shape along the edge surface 61d of the PC sheet 61. The elastic member 63 also has an inner surface 63a and an outer surface 63b. The inner surface 63a of the elastic member 63 is used as a joint surface joined to the outer surface 61b of the PC sheet 61. The elastic member 63 is formed to have a thickness t set as t=t2, and a width w set as w=w2. The thickness t2 may be set to a value of several millimeters, for example, and w2 may be set to a value of several to several tens of millimeters, for example. The elastic member 63 is constructed so that it can be fitted into the receiving portion 52 of the rear cover 50 (see FIG. 8). The thickness t2 of the elastic member 63 is set to a value slightly larger than the height h4 of the interior wall surface 523c of the receiving portion 52 (see FIG. 8). The width w2 of the elastic member 63 is set to a value slightly smaller than the distance d2 of the receiving portion 52 (see FIG. 8).

The thickness t1 of the elastic member 62 and the thickness t2 of the elastic member 63 may be t1=t2 or t1< >t2.

The elastic members 62 and 63 are provided to the PC sheet 61 on the side of the outer surface 61b of the PC sheet 61. In the first embodiment, the elastic members 62 and 63 are provided to the PC sheet 61 on the side of the outer surface 61b of the PC sheet 61 by joining the elastic members 62 and 63 to the outer surface 61b of the PC sheet 61. By joining the elastic members 62 and 63 to the outer surface 61b of the PC sheet 61, the scan window 60 is constructed as shown in FIG. 11. The elastic member 62 is joined to the outer surface 61b of the PC sheet 61 alongside of the edge surface 61c of the PC sheet 61, while the elastic member 63 is joined to the outer surface 61b of the PC sheet 61 alongside of the edge surface 61d of the PC sheet 61. The elastic members 62 and 63 may be joined to the PC sheet 61 by a double-sided tape or an adhesive, for example. It should be noted that one or more members may be provided between the PC sheet 61 and elastic member 62 or 63, as needed. In this case, the PC sheet 61, the one or more member, and elastic member 62 or 63 may be joined by a double-sided tape, an adhesive or the like so that the one or more members are disposed between the PC sheet 61 and elastic member 62 or 63.

The elastic members 62 and 63 are members for preventing liquid from penetrating to the inside of the gantry 2 from the outside of the gantry 2. While the elastic members 62 and 63 may be formed using a foam material, for example, the material is not limited to the foam material, and they may be formed using any material different from the foam material insofar as it is capable of preventing liquid penetration. The way how the elastic members 62 and 63 prevent liquid penetration will be described later.

Figure 14:
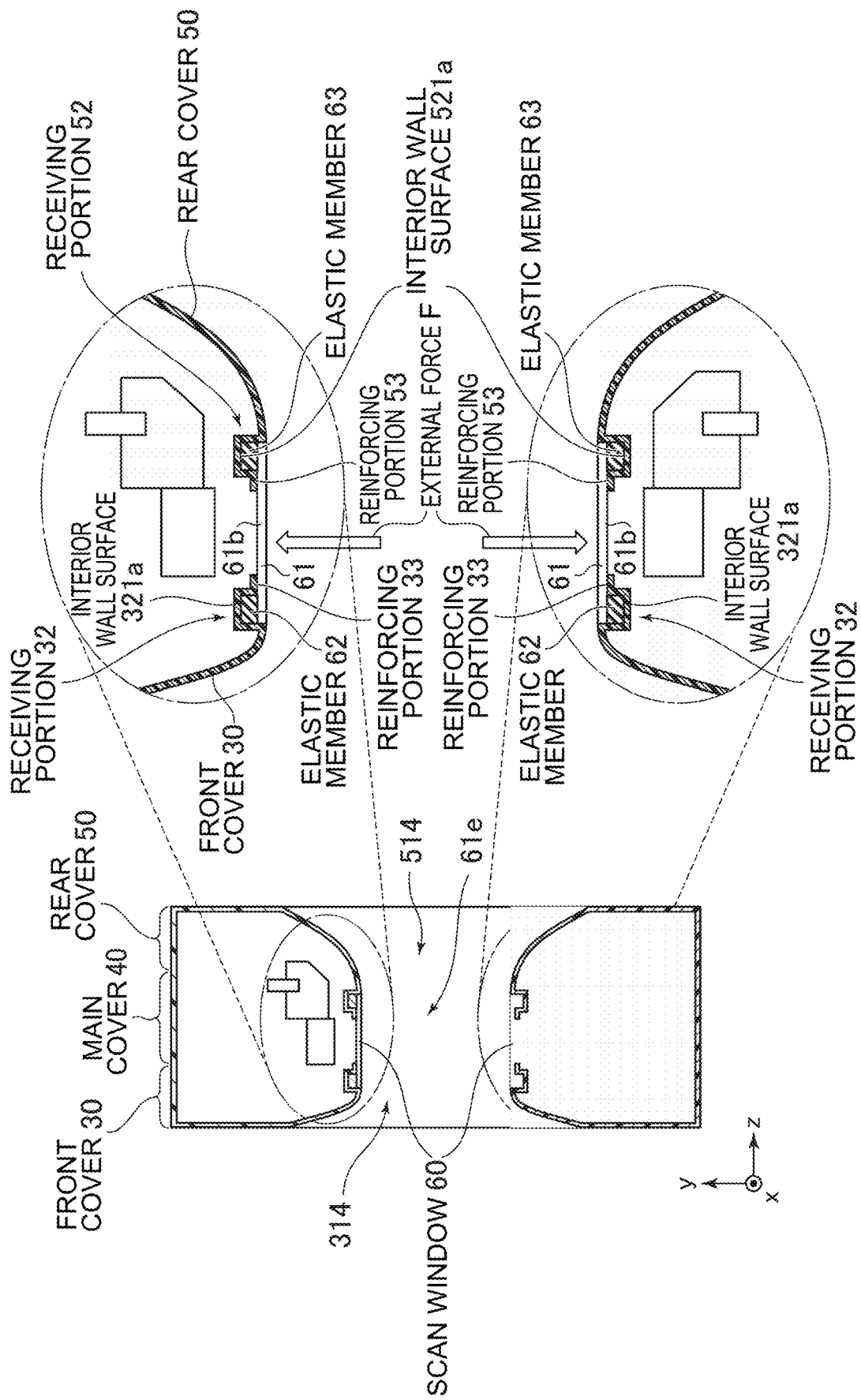
FIG. 14 An enlarged view of the scan window 60 and surrounding members.

The thus-constructed scan window 60 is fitted in the front cover 30 and rear cover 50, as shown in FIGS. 2 and 3. FIG. 14 shows the cross-sectional view shown in FIG. 3, and an enlarged view of the scan window 60 and surrounding members shown in the cross-sectional view.

A worker pushes the elastic members 62 and 63 of the scan window 60 into the receiving portions 32 and 52 (see FIG. 10), respectively, so that the elastic members 62 and 63 are fitted into the receiving portions 32 and 52, respectively. The receiving portions 32 and 52 thus receive the elastic members 62 and 63, respectively. Therefore, the scan window 60 can be fitted in the front cover 30 and rear cover 50. The scan window 60 is attached to the front cover 30 and rear cover 50 along the path of rotation RP of the X-ray tube 6 (see FIG. 3). The opening 61e of the scan window 60 is positioned between the opening 314 of the front cover 30 and the opening 514 of the rear cover 50.

The front cover 30 and rear cover 50 are important members in the present embodiment, and are constructed to achieve, in synergy with the scan window 60, effects that the risk of liquid penetration to the inside of the gantry 2 is reduced and deformation of the scan window 60 is reduced. Now a reason why these effects are achieved will be described. In the description of the effects of the present embodiment, for a better understanding of them, other front cover and rear cover of a structure different from that in the present embodiment and drawbacks thereof will be described before describing the front cover 30 and rear cover 50 used in the present embodiment. Then, after describing the other front cover and rear cover, the front cover 30 and rear cover 50 in the present embodiment constructed to eliminate the drawbacks will be described.

Figure 15:
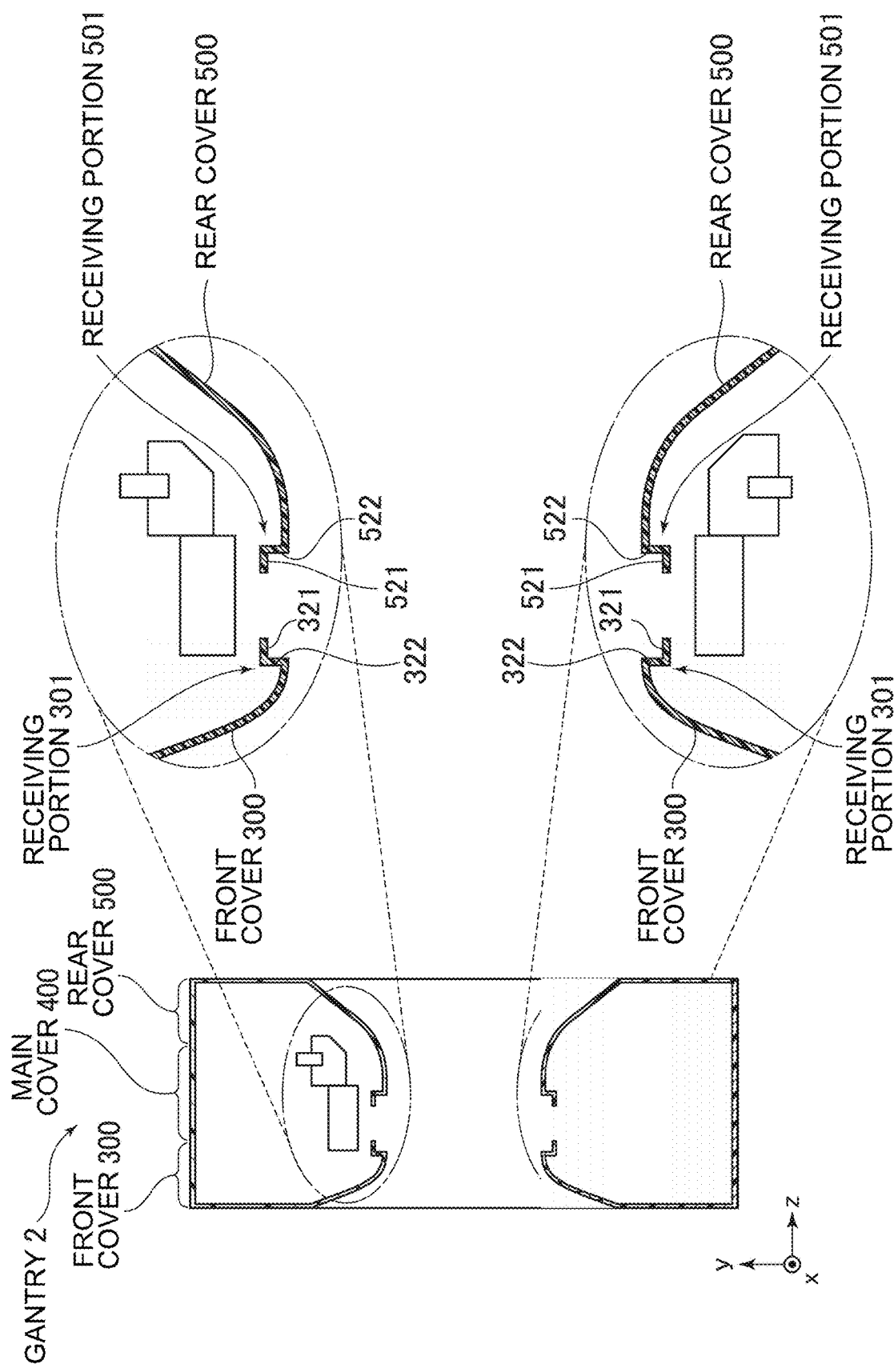
FIG. 15 An explanatory view of the gantry 2 comprising a front cover 300 and a rear cover 500 of a structure different from that in the present embodiment.

FIG. 15 is an explanatory view of the gantry 2 comprising other front cover 300 and rear cover 500 of a structure different from that of the front cover 30 and rear cover 50 in the present embodiment.

FIG. 15 shows a state before the scan window 60 is attached to the front cover 300 and rear cover 500.

Since a main cover 400 has the same structure as that of the main cover 40 (e.g., see FIG. 3) described earlier, description of the main cover 400 will be omitted, and the front cover 300 and rear cover 500 will be described.

In the description of the front cover 300 and rear cover 500, differences thereof from the front cover 30 and rear cover 50 in the present embodiment will be mainly addressed.

Compared with the front cover 30 in the present embodiment, the front cover 300 has the following differences 1 and 2:

(1) The front cover 300 has a receiving portion 301 of a structure different from that of the receiving portion 32 of the front cover 30 (see FIG. 6) in the present embodiment. The receiving portion 301 of the front cover 300 has the base portion 321 and the first side portion 322, as with the receiving portion 32 of the front cover 30 in the present embodiment. The receiving portion 301 of the front cover 300, however, is not provided with the second side portion 323 (see FIG. 6) unlike the receiving portion 32 of the front cover 30 in the present embodiment. The receiving portion 301 of the front cover 300 therefore has the shape of a cross-section in a zy-plane bent at about 90 deg.; and (2) The front cover 30 in the present embodiment has the reinforcing portion 33 (see FIG. 6), while the front cover 300 is not provided with the reinforcing portion 33.

Next, the rear cover 500 will be described.

Compared with the rear cover 50 in the present embodiment, the rear cover 500 has the following differences 3 and 4:

(3) The rear cover 500 has a receiving portion 501 of a structure different from that of the receiving portion 52 of the rear cover 50 (see FIG. 8) in the present embodiment. The receiving portion 501 of the rear cover 500 has the base portion 521 and the third side portion 522, as with the receiving portion 52 of the rear cover 50 in the present embodiment. The receiving portion 501 of the rear cover 500, however, is not provided with the fourth side portion 523 (see FIG. 8), unlike the receiving portion 52 of the rear cover 50 in the present embodiment. The receiving portion 501 of the rear cover 500 therefore has the shape of a cross-section in the zy-plane bent at about 90 deg.; and (4) The rear cover 50 in the present embodiment has the reinforcing portion 53 (see FIG. 8), while the rear cover 500 is not provided with the reinforcing portion 53.

Figure 16:
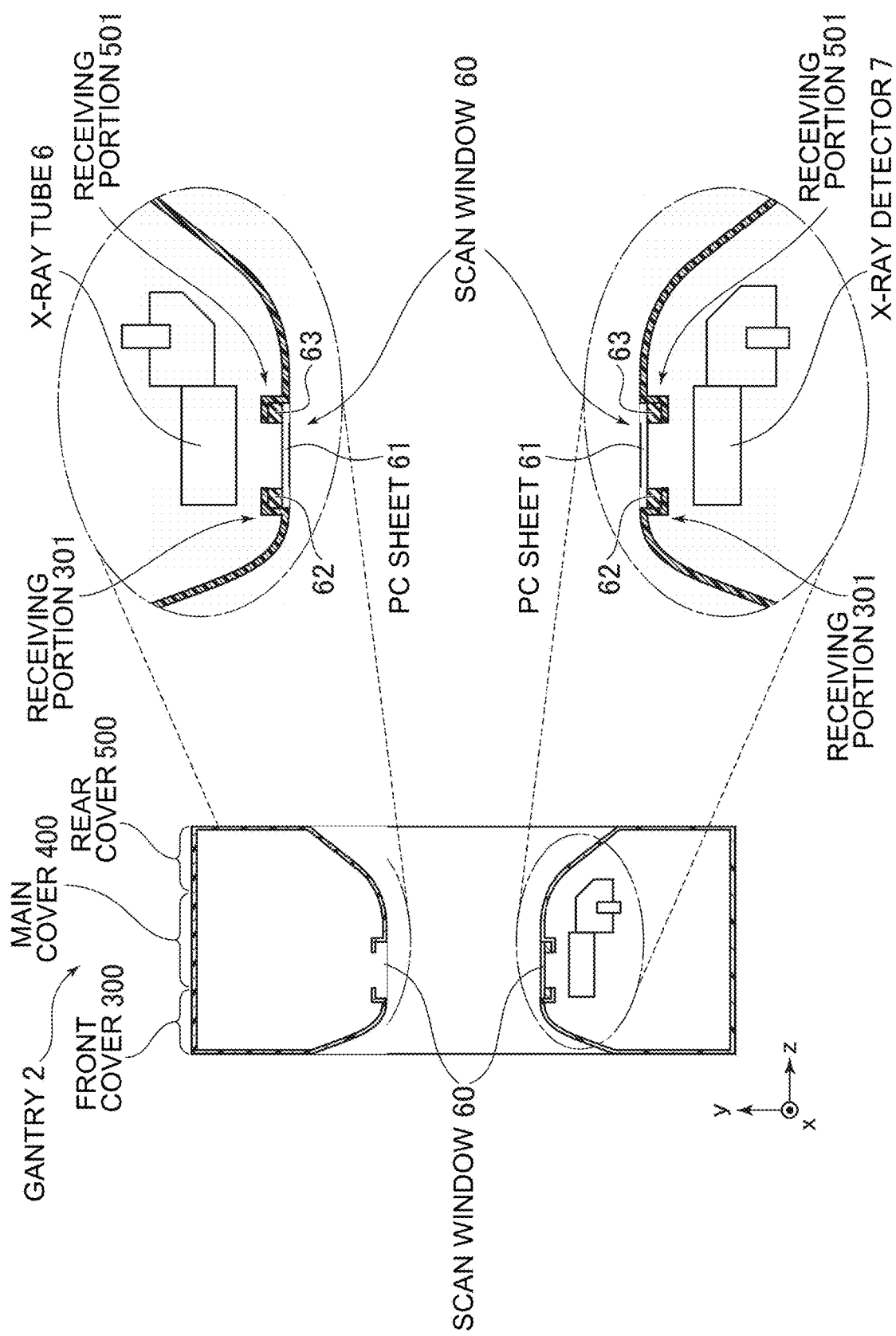
FIG. 16 A view showing a state after the front cover 300 and rear cover 500 are fitted with the scan window 60.

The scan window 60 is fitted in the thus-constructed front cover 300 and rear cover 500 (see FIG. 16).

FIG. 16 shows a state after the front cover 300 and rear cover 500 are fitted with the scan window 60.

A worker pushes the elastic members 62 and 63 of the scan window 60 into the receiving portions 301 and 501, respectively. Therefore, the scan window 60 can be fitted in the front cover 300 and rear cover 500.

By fitting the scan window 60 in the front cover 300 and rear cover 500, the inside of the gantry 2 can be shielded from an external environment. Moreover, the scan window 60 has the elastic members 62 and 63. When the worker has pushed the elastic members 62 and 63 against the receiving portions 301 and 501, the elastic member 62 is deformed into intimate contact with an interior wall surface of the receiving portion 301, and moreover, the elastic member 63 is deformed into intimate contact with an interior wall surface of the receiving portion 501. This can substantially reduce the risk of liquid penetrating to the inside of the gantry 2 from the outside of the gantry 2.

Figure 17:
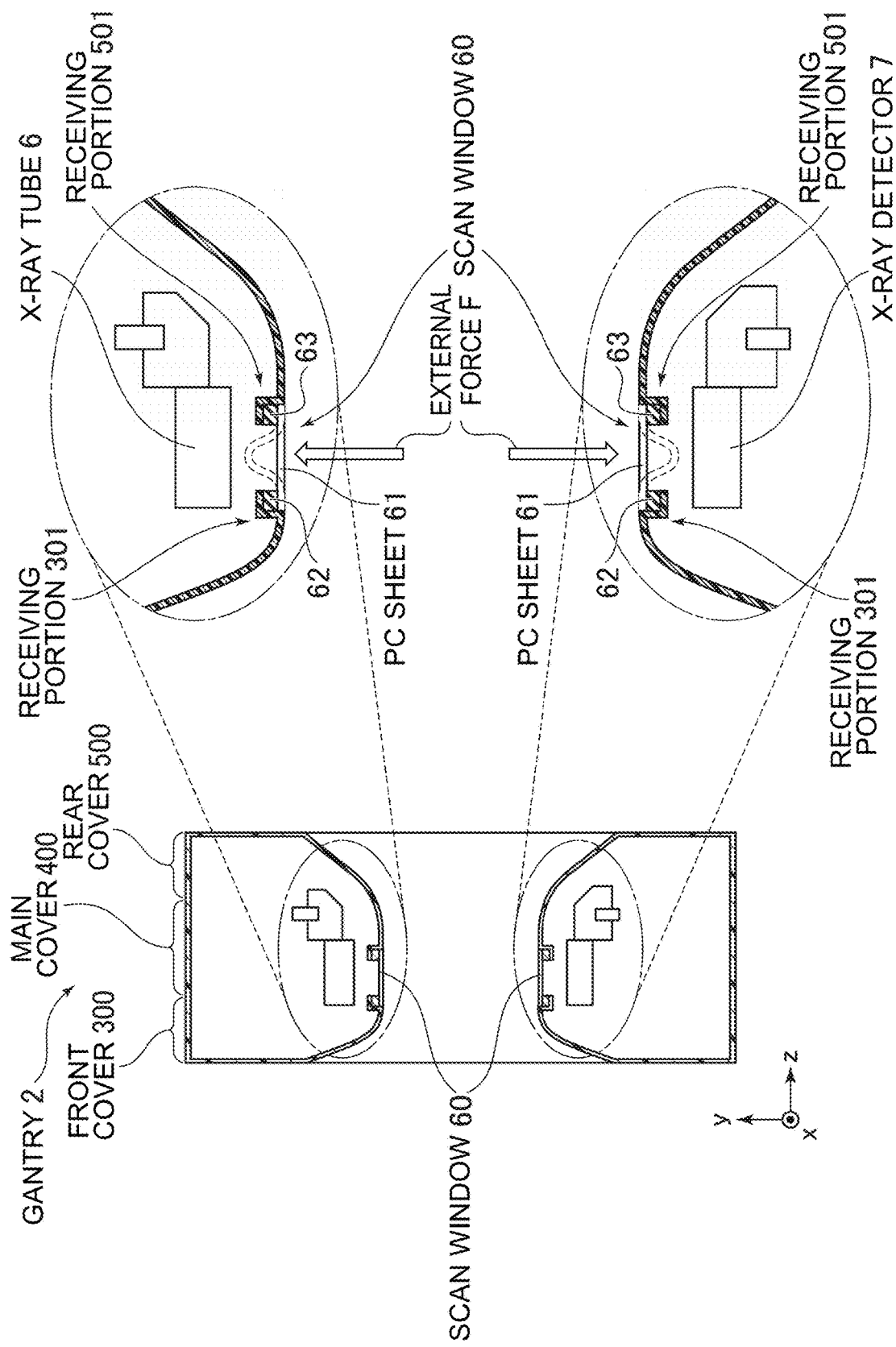
FIG. 17 A view showing deformation of a PC sheet 61.

However, it is necessary that the PC sheet 61 of the scan window be formed to have as thin a thickness of the sheet as possible so that X-ray attenuation is as small as possible. Accordingly, when an external force F is applied to the scan window 60 by the rotating X-ray tube 6 and X-ray detector 7, deformation of the PC sheet 61 increases, as shown in FIG. 17, resulting in the risk of contact between the scan window 60 and rotating elements (e.g., X-ray tube 6 or X-ray detector 7), which may lead to an accident. Moreover, when the external force F is applied to the scan window 60, the elastic members 62 and 63 are compressed by the external force F. With the elastic members 62 and 63 being compressed, the thickness of the elastic members 62 and 63 is reduced, so that the reduction of the thickness of the elastic members 62 and 63 directly causes the scan window 60 to be brought closer to the rotating elements. Therefore, compression of the elastic members 62 and 63 may also be a cause of the contact between the scan window 60 and the rotating elements. On the other hand, to prevent the PC sheet 61 of the scan window 60 from being brought closer to the rotating elements due to compression of the elastic members 62 and 63, it may be contemplated to omit the elastic members 62 and 63 and directly fit the PC sheet 61 in the front cover and rear cover. Such omission of the elastic members 62 and 63, however, poses a problem that prevention of liquid penetration to the inside of the gantry 2 is disabled.

Accordingly, in the present embodiment, the front cover 30 and rear cover 50 are constructed to deal with these problems. Now a reason why the problems can be dealt with will be described referring to FIG. 14.

The front cover 30 and rear cover 50 have the receiving portions 32 and 52, respectively, in which the elastic members 62 and 63 are to be disposed. As described earlier referring to FIG. 13, the thickness t=t1 of the elastic member 62 is set to a value larger than the height h2 of the interior wall surface 323c of the receiving portion 32 (see FIG. 6), and the thickness t=t2 of the elastic member 63 is set to a value larger than the height h4 of the interior wall surface 523c of the receiving portion 52 (see FIG. 8). Therefore, when a worker has fitted the elastic members 62 and 63 into the receiving portions 32 and 52, the elastic member 62 is pushed against the interior wall surface 321a of the base portion of the receiving portion 32, and moreover, the elastic member 63 is pushed against the interior wall surface 521a of the base portion of the receiving portion 52. Thus, the elastic member 62 is put against the interior wall surface 321a of the receiving portion 32 and then is deformed so as to be in intimate contact with the interior wall surface 321a, and the elastic member 63 is put against the interior wall surface 521a of the receiving portion 52 and then is deformed so as to be in intimate contact with the interior wall surface 521a. This can substantially reduce the risk of liquid penetrating to the inside of the gantry 2 from the outside of the gantry 2.

Moreover, when the worker has fitted the elastic members 62 and 63 into the receiving portions 32 and 52, respectively, the outer surface 61b of the PC sheet 61 is brought into contact with or proximity to the reinforcing portions 33 and 53. Therefore, when an external force F is applied to the PC sheet 61, the reinforcing portions 33 and 53 support the PC sheet 61 from the side of the outer surface 61b of the PC sheet 61, so that the PC sheet 61 is reinforced, which can substantially reduce deformation of the PC sheet.

In the first embodiment, once the scan window 60 has been fitted in the front cover 30 and rear cover 50, liquid is prevented from penetrating to the inside of the gantry by the elastic member 62 put against the interior wall surface 321a of the base portion 321 of the receiving portion 32, and moreover, by the elastic member 63 put against the interior wall surface 521a of the base portion 521 of the receiving portion 52. The elastic member 62 and receiving portion 32, however, may be formed so that the elastic member 62 is put against the interior wall surface 322c of the first side portion 322 (see FIG. 6) and the interior wall surface 323c of the second side portion 323 (see FIG. 6) of the receiving portion 32, as well as against the interior wall surface 321a of the base portion 321 of the receiving portion 32. By the elastic member 62 thus put against the three interior wall surfaces 321a, 322c, and 323c of the receiving portion 32, the effect of liquid penetration prevention of the elastic member 62 can be further enhanced. It should be noted that insofar as the effect of liquid penetration prevention is achieved, the elastic member 62 is not necessarily put against the three interior wall surfaces 321a, 322c, and 323c of the receiving portion 32, and the elastic member 62 and receiving portion 32 may be constructed so that the elastic member 62 is put against at least one of these three interior wall surfaces 321a, 322c, and 323c.

Similarly, insofar as the effect of liquid penetration prevention is achieved, the other elastic member 63 is not necessarily put against the three interior wall surface 521a, 522c, and 523c of the receiving portion 52 (see FIG. 8), and the elastic member 63 and receiving portion 52 may be constructed so that the elastic member 63 is put against at least one of these three interior wall surfaces 521a, 322c, and 323c.

In the first embodiment, the front cover 30 and rear cover 50 are molded using a die. Now an undercut that may cause complication of the structure of the die for the front cover 30 and rear cover 50 will be briefly described referring to FIG. 10.

As shown in FIG. 10, a border portion B1 between the front wall portion 31 and receiving portion 32 of the front cover 30 has a bent shape, and a border portion B2 between the rear wall portion 51 and receiving portion 52 of the rear cover 50 also has a bent shape. Such a bent shape may constitute an undercut A, which may cause complication of the structure of the die for the front cover 30. Accordingly, an example of the front cover and rear cover that has dealt with the undercut problem will be described (see FIG. 18).

Figure 18:
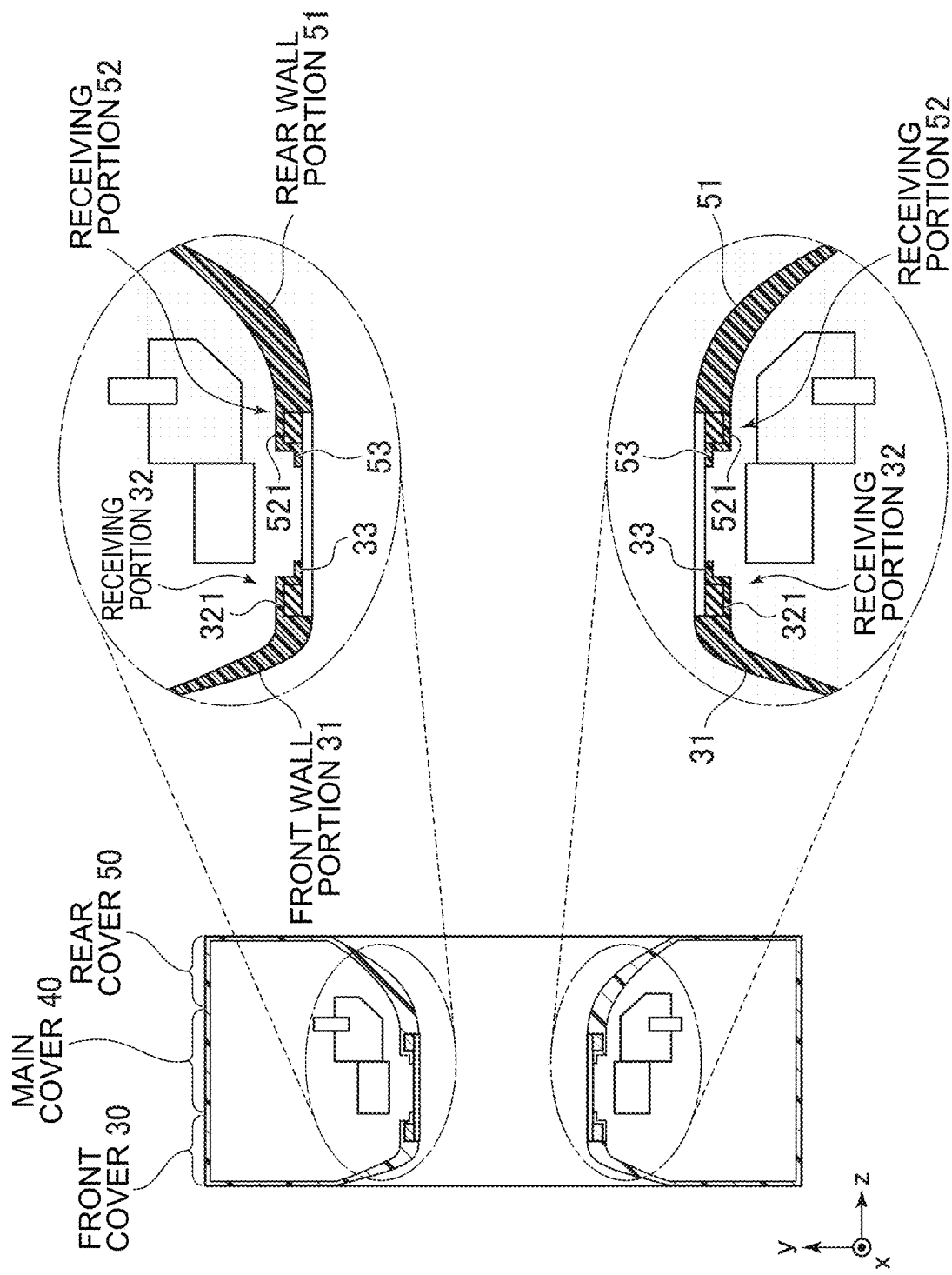
FIG. 18 A view showing an example of the front cover 30 and rear cover that have dealt with an undercut problem.

FIG. 18 is a view showing an example of the front cover 30 and rear cover that has dealt with the undercut problem.

In the example shown in FIG. 18, the thickness of a portion of the front wall portion 31 on the side of the receiving portion 32 is increased, and further, the base portion 321 of the receiving portion 32 is formed integrally with the front wall portion 31. Moreover, the thickness of a portion of the rear wall portion 51 on the side of the receiving portion 52 is increased, and the base portion 521 of the receiving portion 52 is formed integrally with the rear wall portion 51. The front cover 30 and rear cover in FIG. 18 can thus have a structure without the undercut A shown in FIG. 10. Accordingly, the front cover 30 and rear cover 50 in FIG. 18 can be more easily released from the die as compared with those in FIG. 10.

In the first embodiment, the receiving portion and reinforcing portion are formed integrally with each other. The receiving portion and reinforcing portion, however, may be formed as separate components so that the reinforcing portion may be joined to the receiving portion.

Second Embodiment

While the CT apparatus in a second embodiment has a front cover and a rear cover of different structure as compared with that in the first embodiment, other constructions are the same. Accordingly, in the description of the second embodiment, the front cover and rear cover will be mainly addressed.

Figure 19:
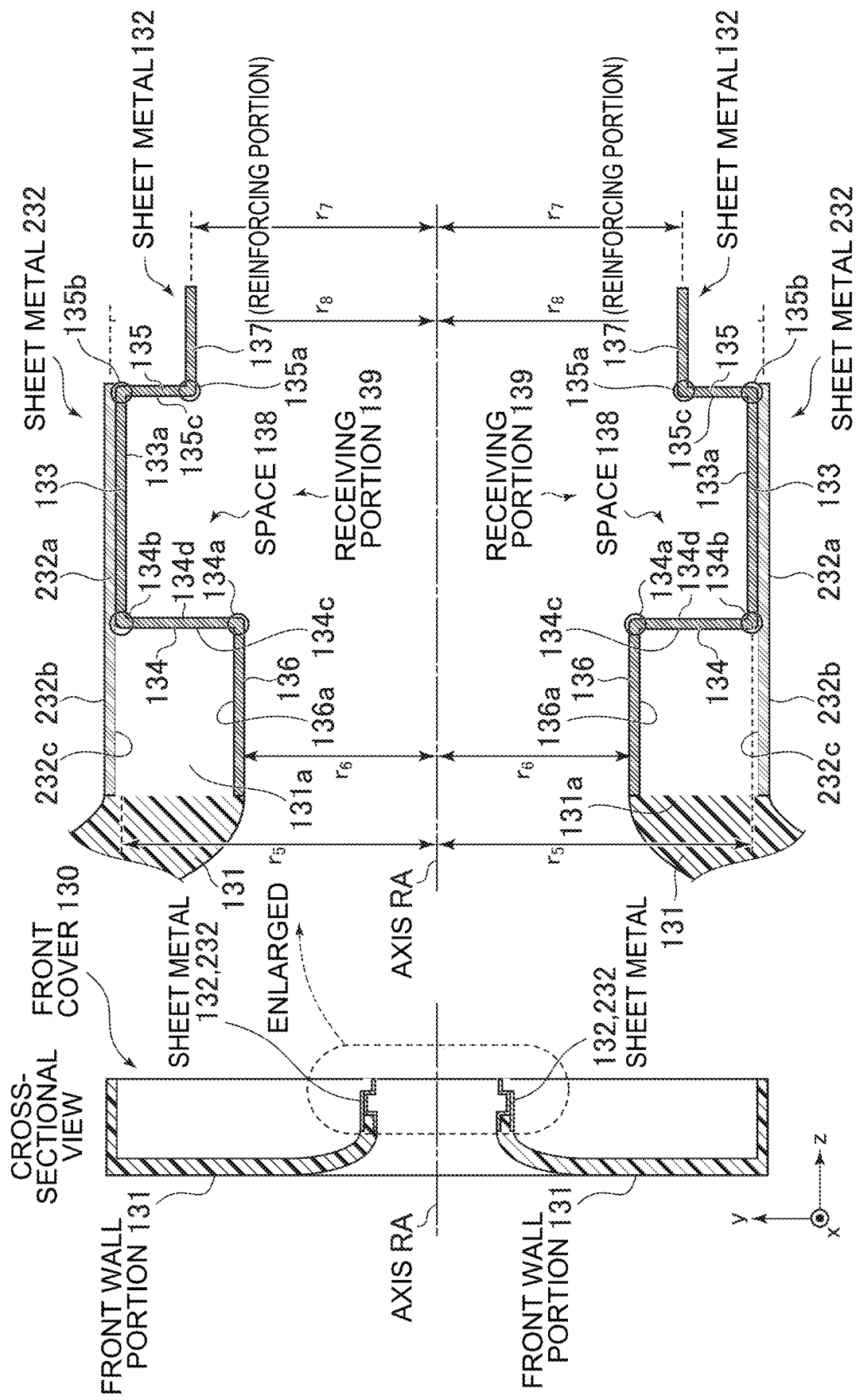
FIG. 19 An explanatory view of a front cover 130 in a second embodiment.

FIG. 19 is an explanatory view of a front cover 130 in the second embodiment.

The front cover 130 has a front wall portion 131, and sheet metals 132 and 232.

The sheet metal 132 has a base portion 133, a first side portion 134, a second side portion 135, a first protruding portion 136, and a second protruding portion 137.

The base portion 133 has a ring shape extending along the circumference of a circle of radius r5 around the axis RA.

The first side portion 134 has an inner edge portion 134a extending along the circumference of a circle of radius r6 around the axis RA, and an outer edge portion 134b extending along the circumference of a circle of radius r5 around the axis RA. The outer edge portion 134b is formed integrally with the base portion 133.

The second side portion 135 is formed to face the first side portion 134. The second side portion 135 has an inner edge portion 135a extending along the circumference of a circle of radius r7 around the axis RA, and an outer edge portion 135b extending along the circumference of a circle of radius r5 around the axis RA. The outer edge portion 135b is formed integrally with the base portion 133.

The first protruding portion 136 is formed to protrude in a direction away from the second side portion 135 with respect to the first side portion 134. The first protruding portion 136 extends along the circumference of a circle of radius r6 around the axis RA. The first protruding portion 136 is formed integrally with the inner edge portion 134a of the first side portion 134.

The second protruding portion 137 is formed to protrude in a direction away from the first side portion 134 with respect to the second side portion 135. The second protruding portion 137 extends along the circumference of a circle of radius r7 around the axis RA. The second protruding portion 137 is formed integrally with the inner edge portion 135a of the second side portion 135.

The base portion 133 has an interior wall surface 133a, the first side portion 134 has an interior wall surface 134d, and the second side portion 135 has an interior wall surface 135c. Space 138 surrounded by these interior wall surfaces 133a, 134d, and 135c is used as space in which the elastic member 62 of the scan window 60 (see FIG. 11) is to be disposed.

The sheet metal 132 is constructed of the integrally formed base portion 133, first side portion 134, second side portion 135, first protruding portion 136, and second protruding portion 137.

The other sheet metal 232 has a supporting portion 232a for supporting the base portion 133 of the sheet metal 132, and a protruding portion 232b protruding from the supporting portion 232a.

Space surrounded by the first protruding portion 136 and first side portion 134 of the sheet metal 132 and the protruding portion 232b of the sheet metal 232 makes up a groove into which a rim portion 131a of the front wall portion 131 is to be inserted. The rim portion 131a of the front wall portion 131 may be joined to a wall surface 136a of the first protruding portion 136 and a wall surface 134c of the first side portion 134 of the sheet metal 132, and to a wall surface 232c of the protruding portion 232b of the sheet metal 232 by an adhesive, for example.

The base portion 133, first side portion 134, and second side portion 135 of the sheet metal 132 make up a receiving portion 139 in which the elastic member 62 of the scan window 60 (see FIG. 11) is to be disposed. The second protruding portion 137 of the sheet metal 132 makes up a reinforcing portion 137 for reinforcing the PC sheet 61 (see FIG. 11) so that deformation of the PC sheet 61 is reduced. Thus, the sheet metal 132 performs functions of the receiving portion 139 and reinforcing portion 137. In the second embodiment, the receiving portion 139 is joined to the front wall portion 131. It should be noted that in FIG. 19, the size of the receiving portion 139 and reinforcing portion 137 is exaggerated relative to the lengths of the radii r5, r6, r7, and r8 in order that the structure of the receiving portion 139 and reinforcing portion 137 is visually comprehensible.

Next, the rear cover in the second embodiment will be described.

Figure 20:
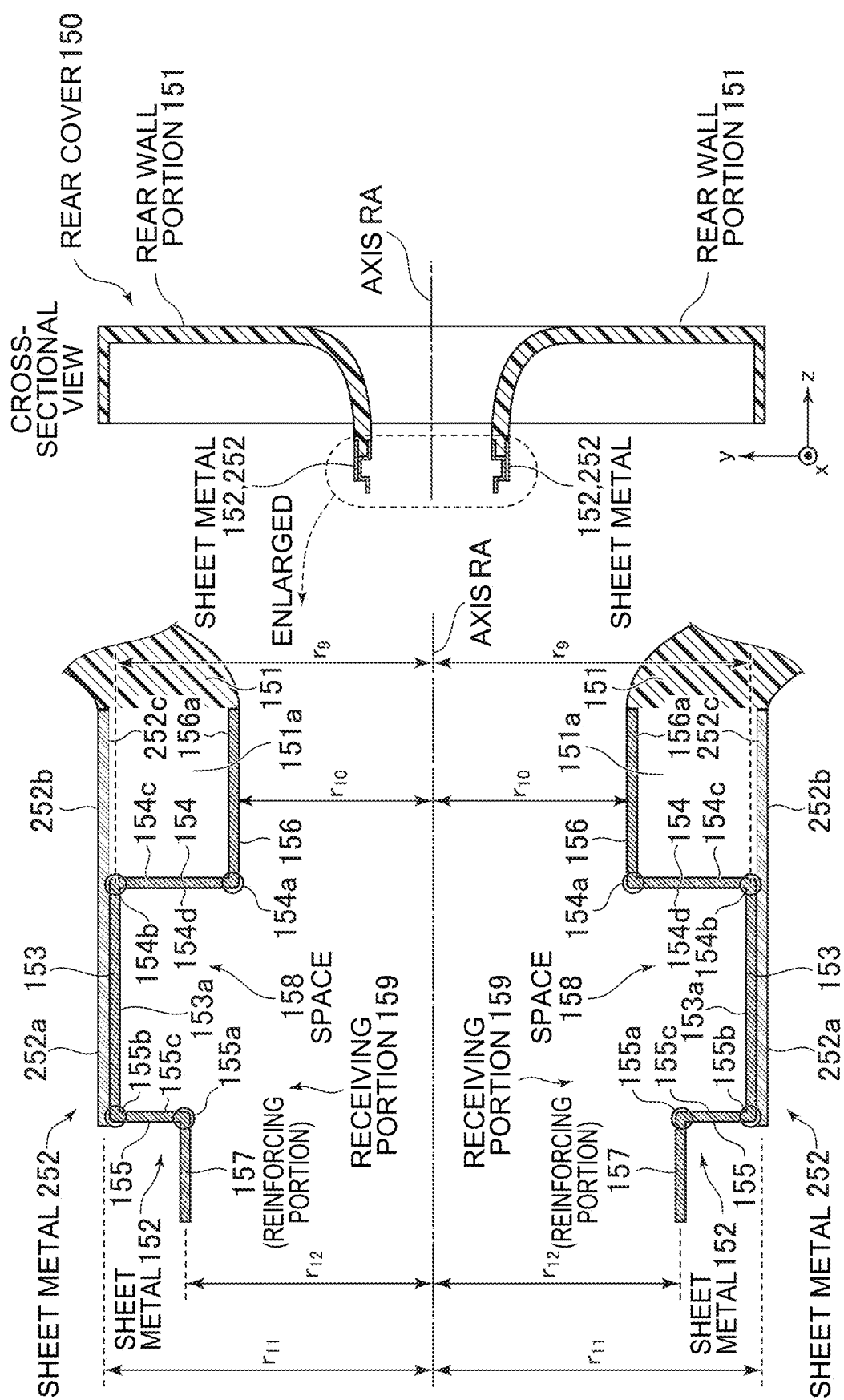
FIG. 20 An explanatory view of a rear cover 150 in the second embodiment.

FIG. 20 is an explanatory view of a rear cover 150 in the second embodiment.

The rear cover 150 has a rear wall portion 151, and sheet metals 152 and 252.

The sheet metal 152 has a base portion 153, a third side portion 154, a fourth side portion 155, a third protruding portion 156, and a fourth protruding portion 157.

The base portion 153 has a ring shape extending along the circumference of a circle of radius r9 around the axis RA.

The third side portion 154 has an inner edge portion 154a extending along the circumference of a circle of radius r10 around the axis RA, and an outer edge portion 154b extending along the circumference of a circle of radius r9 around the axis RA. The outer edge portion 154b is formed integrally with the base portion 153.

The fourth side portion 155 is formed to face the third side portion 154. The fourth side portion 155 has an inner edge portion 155a extending along the circumference of a circle of radius r12 around the axis RA, and an outer edge portion 155b extending along the circumference of a circle of radius r9 around the axis RA. The outer edge portion 155b is formed integrally with the base portion 153.

The third protruding portion 156 is formed to protrude in a direction away from the fourth side portion 155 with respect to the third side portion 154. The third protruding portion 156 extends along the circumference of a circle of radius r10 around the axis RA. The third protruding portion 156 is formed integrally with the inner edge portion 154a of the third side portion 154.

The fourth protruding portion 157 is formed to protrude in a direction away from the third side portion 154 with respect to the fourth side portion 155. The fourth protruding portion 157 extends along the circumference of a circle of radius r12 around the axis RA. The fourth protruding portion 157 is formed integrally with the inner edge portion 155a of the fourth side portion 155.

The base portion 153 has an interior wall surface 153a, the third side portion 154 has an interior wall surface 154d, and the fourth side portion 155 has an interior wall surface 155c. Space 158 surrounded by these interior wall surfaces 153a, 154d, and 155c is used as space in which the elastic member 63 of the scan window 60 (see FIG. 11) is to be disposed.

The sheet metal 152 is constructed of the integrally formed base portion 153, third side portion 154, fourth side portion 155, third protruding portion 156, and fourth protruding portion 157.

The other sheet metal 252 has a supporting portion 252a for supporting the base portion 153 of the sheet metal 152, and a protruding portion 252b protruding from the supporting portion 252a.

Space surrounded by the third protruding portion 156 and third side portion 154 of the sheet metal 152 and the protruding portion 252b of the sheet metal 252 makes up a groove into which a rim portion 151a of the rear wall portion 151 is to be inserted. The rim portion 151a of the rear wall portion 151 may be joined to a wall surface 156a of the third protruding portion 156 and a wall surface 154c of the third side portion 154 of the sheet metal 152, and to a wall surface 252c of the protruding portion 252b of the sheet metal 252 by an adhesive, for example.

The base portion 153, third side portion 154, and fourth side portion 155 of the sheet metal 152 make up a receiving portion 159 in which the elastic member 63 of the scan window 60 (see FIG. 11) is to be disposed. The fourth protruding portion 157 of the sheet metal 152 makes up a reinforcing portion 157 for reinforcing the PC sheet 61 (see FIG. 11) so that deformation of the PC sheet 61 is reduced. Thus, the sheet metal 152 performs functions of the receiving portion 159 and reinforcing portion 157. In the second embodiment, the receiving portion 159 is joined to the rear wall portion 151. It should be noted that in FIG. 20, the size of the receiving portion 159 and reinforcing portion 157 is exaggerated relative to the lengths of the radii r9, r10, r11, and r12 in order that the structure of the receiving portion 159 and reinforcing portion 157 is visually comprehensible.

Figure 21:
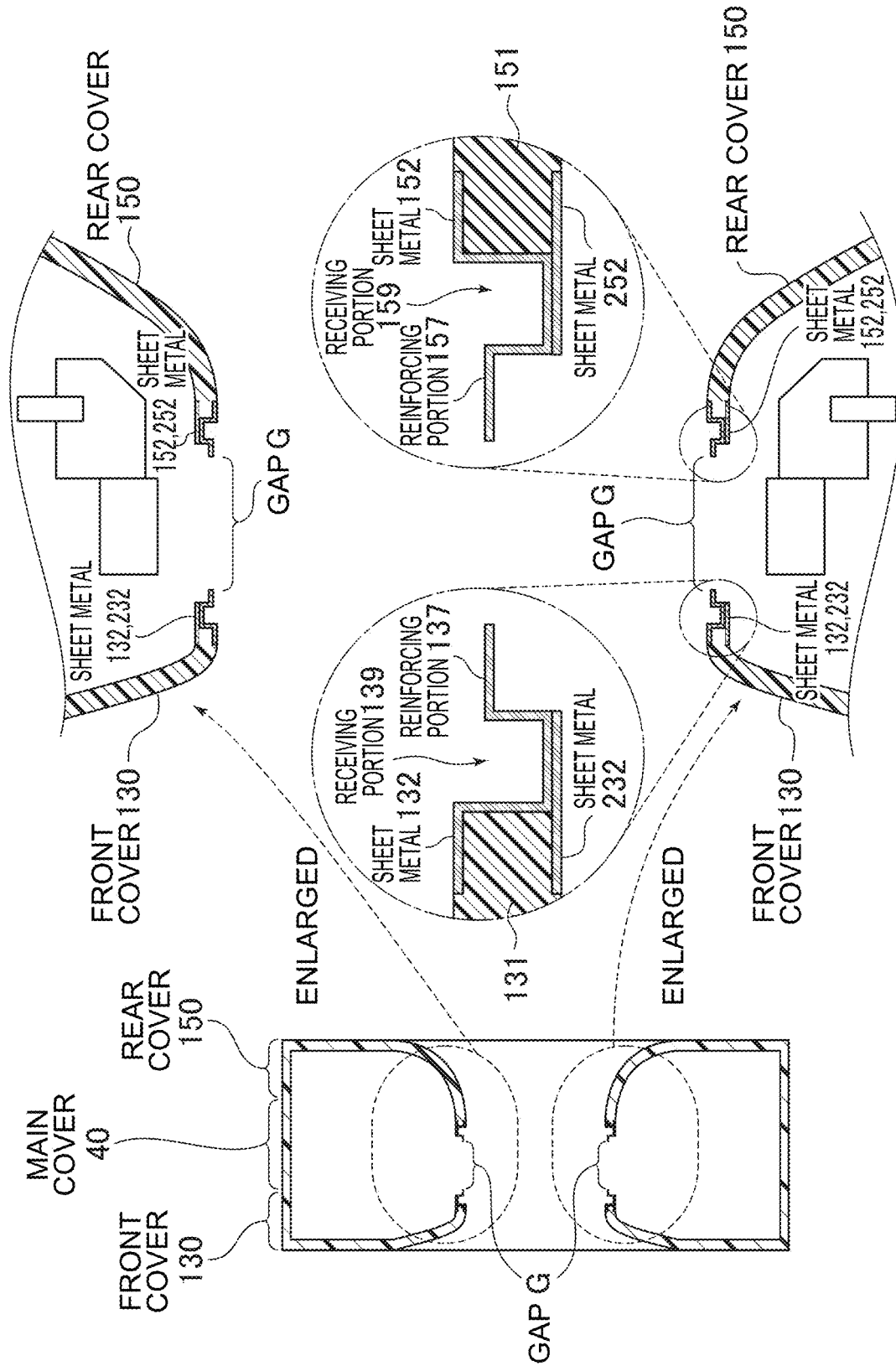
FIG. 21 A view showing a state in which the front cover 130 is fixed on the side of a front surface of the main cover 40 and the rear cover 150 is fixed on the side of a back surface of the main cover 40.

The thus-constructed front cover 130 and rear cover 150 are fixed to the main cover (see FIG. 21).

FIG. 21 is a view schematically showing a state in which the front cover 130 is fixed on the side of the front surface of the main cover 40 and the rear cover 150 is fixed on the side of the back surface of the main cover 40.

By the front cover 130 and rear cover 150 being fixed to the main cover 40, a gap G is formed between the front cover 130 and rear cover 150, as shown in FIG. 21.

Figure 22:
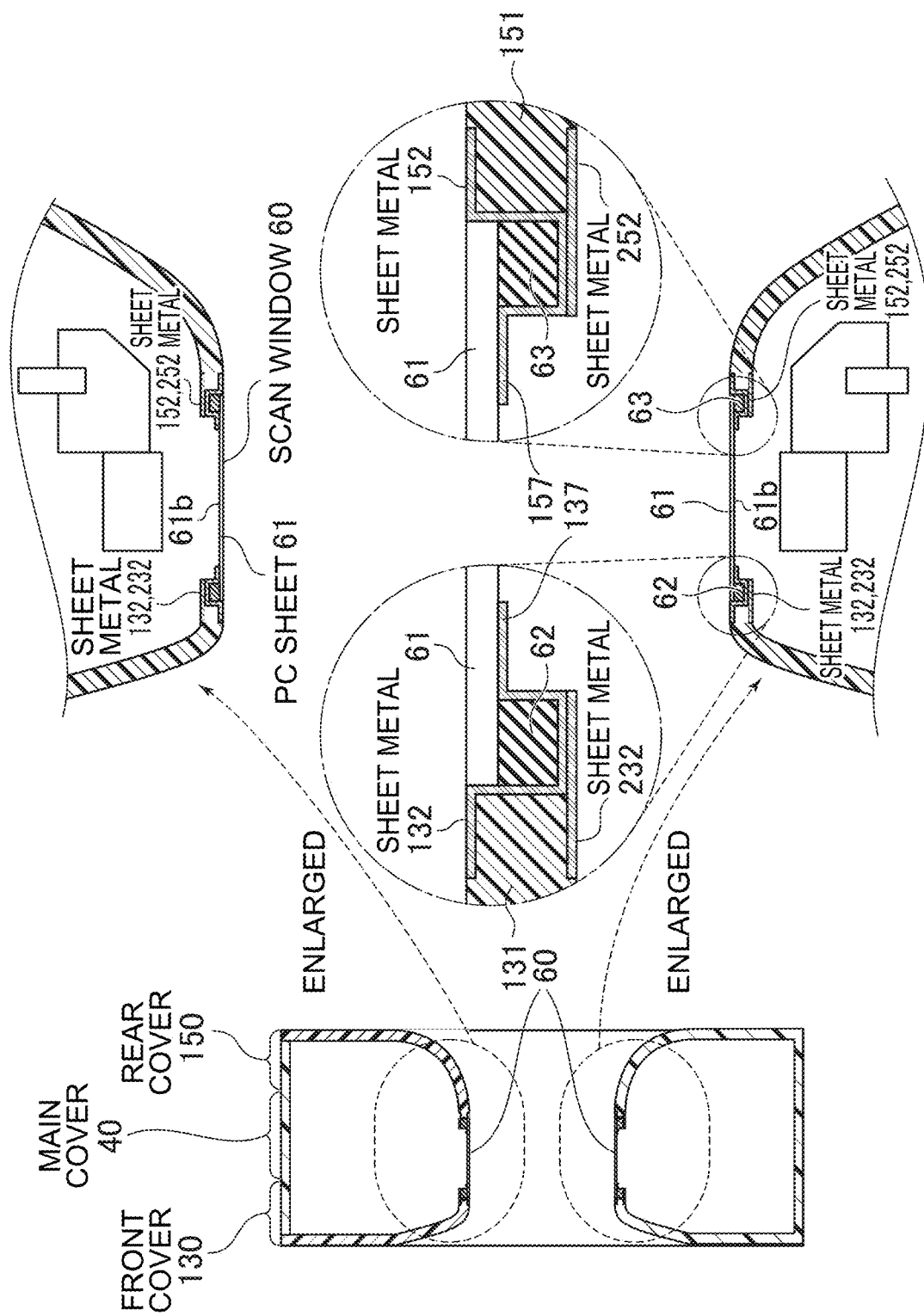
FIG. 22 A view showing a state in which the front cover 130 and rear cover 150 are fitted with the scan window 60.

The scan window 60 is fitted in the front cover 130 and rear cover 150 so as to fill the gap G (see FIG. 22).

FIG. 22 is a view schematically showing a state in which the front cover 130 and rear cover 150 are fitted with the scan window 60.

When a worker has fitted the elastic members 62 and 63 of the scan window 60 into the receiving portions 139 and 159 (see FIG. 21), the elastic member 62 is pushed against the interior wall surface of the receiving portion 139, and moreover, the elastic member 63 is pushed against the interior wall surface of the receiving portion 159. Thus, the elastic member 62 is deformed into intimate contact with the receiving portion 139, and the elastic member 63 is deformed into intimate contact with the receiving portion 159. This can substantially reduce the risk of liquid penetrating to the inside of the gantry 2 from the outside of the gantry 2.

Moreover, when the worker has fitted the elastic members 62 and 63 into the receiving portions 139 and 159, respectively, the outer surface 61b of the PC sheet 61 is brought into contact with or proximity to the reinforcing portions 137 and 157. Therefore, when an external force F is applied to the PC sheet 61, the reinforcing portions 137 and 157 support the PC sheet 61, so that the PC sheet 61 is reinforced, which can substantially reduce deformation of the PC sheet.

Accordingly, the second embodiment, as in the first embodiment, can substantially reduce the risk of liquid penetrating to the inside of the gantry 2 from the outside of the gantry 2, and further, can reduce deformation of the PC sheet 61.

Moreover, in the second embodiment, the front wall portion 131 is molded using a die, while the receiving portion 139 and reinforcing portion 137 are shaped by processing sheet metal. Therefore, in fabricating the front cover 130 in the second embodiment, it is not necessary to prepare a die taking account of an undercut corresponding to the shape of the receiving portion 139, and it is sufficient to provide a die for molding the front wall portion 131 excluding the receiving portion 139, so that the front wall portion 131 can be easily releasable from a die. Likewise, in fabricating the rear cover 150, the rear wall portion 151 can be easily released from a die.

Furthermore, in the second embodiment, the sheet metal is used to construct the receiving portion and reinforcing portion, so that strength of the receiving portion and reinforcing portion can be enhanced.

Third Embodiment

In a third embodiment, an example in which a scan window fitted in a front cover and a rear cover is fixed by a fixing member will be described.

The third embodiment will be described referring to FIGS. 23 and 24.

Figure 23:
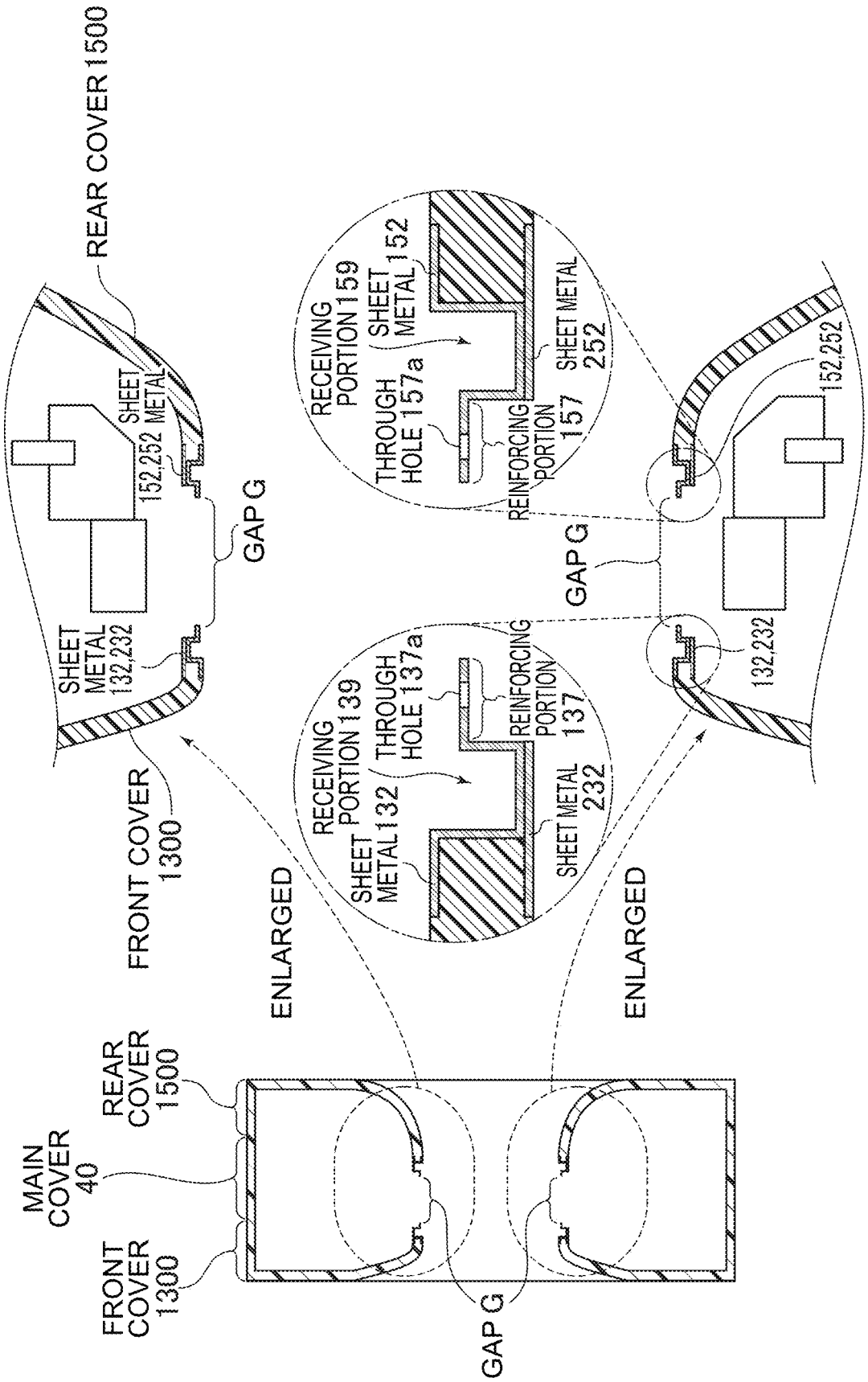
FIG. 23 A view showing a front cover 1300 and a rear cover 1500 before being fitted with the scan window 60.

FIG. 23 is a view showing a front cover 1300 and a rear cover 1500 before being fitted with the scan window 60.

The front cover 1300 and rear cover 1500 in the third embodiment have a basic structure similar to that of the front cover 130 and rear cover 150 in the second embodiment. However, the front cover 1300 in the third embodiment is different from the front cover 130 in the second embodiment in that the former is formed with a through hole 137a for passing a screw therethrough into the protruding portion (reinforcing portion) 137 of the sheet metal 132. The rear cover 1500 in the third embodiment is also different from the rear cover 150 in the second embodiment in that the former is formed with a through hole 157a for passing a screw therethrough into the protruding portion (reinforcing portion) 157 of the sheet metal 152.

Figure 24:
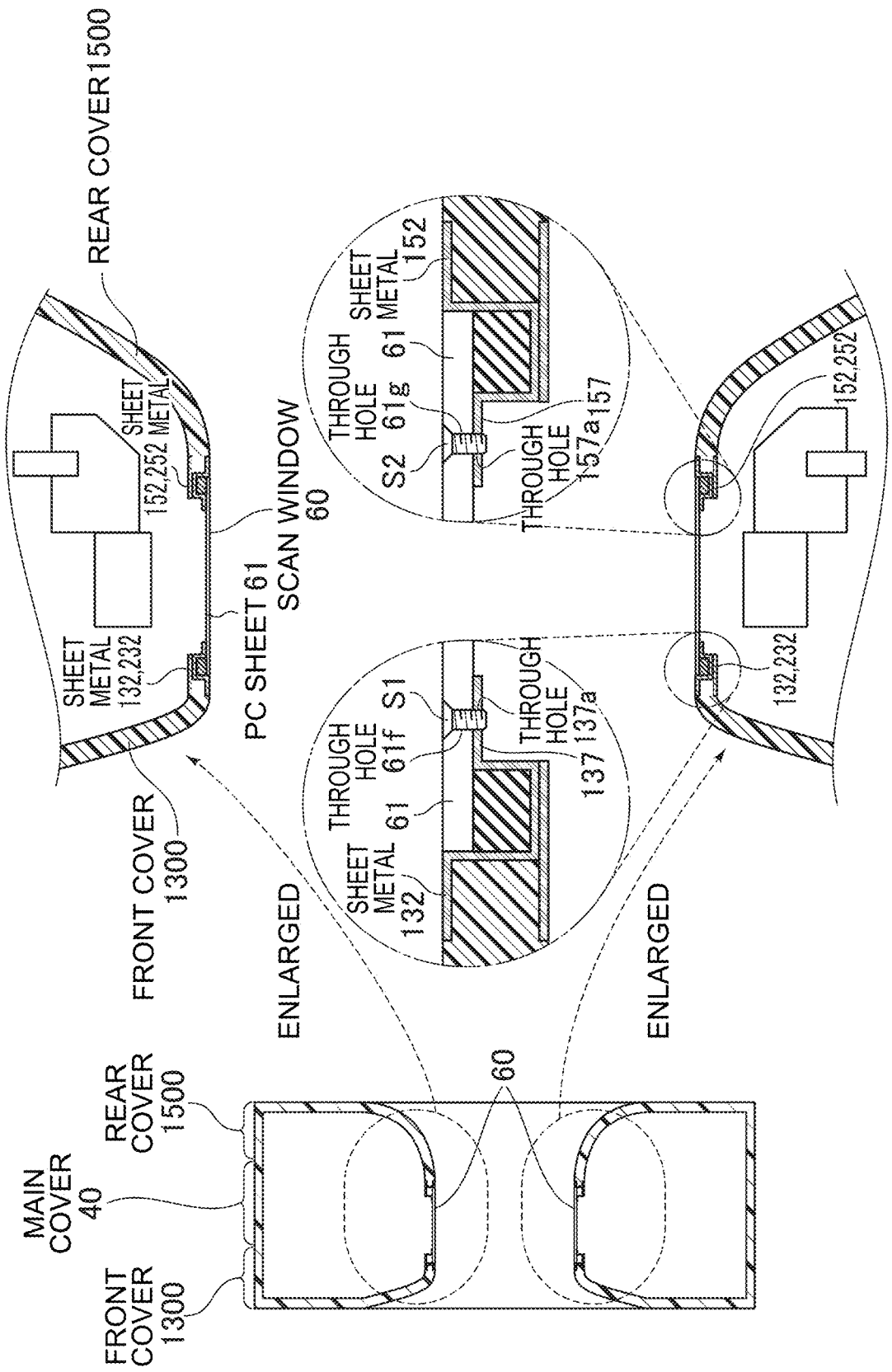
FIG. 24 A view showing a state after the front cover 1300 and rear cover 1500 are fitted with the scan window 60.

FIG. 24 is a view showing a state after the front cover 1300 and rear cover 1500 are fitted with the scan window 60.

In the third embodiment, the PC sheet 61 is formed with a through hole 61f for passing a screw therethrough at a position corresponding to the through hole 137a in the protruding portion (reinforcing portion) 137 of the sheet metal 132, and further, is formed with a through hole 61g for passing a screw therethrough at a position corresponding to the through hole 157a in the protruding portion (reinforcing portion) 157 of the sheet metal 152.

In fitting the scan window 60 in the front cover 1300 and rear cover 1500 in the third embodiment, a worker can register the through hole 61f in the scan window 60 in communication with the through hole 137a in the protruding portion (reinforcing portion) 137 of the sheet metal 132, and further, register the through hole 61g in the scan window 60 in communication with the through hole 157a in the protruding portion (reinforcing portion) 157 of the sheet metal 152.

After fitting the scan window 60 in the front cover 1300 and rear cover 1500, the worker screws a screw S1 into the through holes 61f and 137a, and a screw S2 into the through holes 61g and 157a. The screw S1 fixes the scan window 60 to the front cover 1300 in a portion where the PC sheet 61 and the reinforcing portion 137 lie over each other. The screw S2 fixes the scan window 60 to the rear cover 1500 in a portion where the PC sheet 61 and the reinforcing portion 157 lie over each other. Since the PC sheet 61 is thus firmly fixed to the reinforcing portions 137 and 157, deformation of the PC sheet 61 can be further reduced.

While in the third embodiment, the screws S61 and S2 are used to fix the scan window 60 to the front cover 1300 and rear cover 1500, any fixing member different from the screw may be used to fix the scan window 60.

Fourth Embodiment

In a fourth embodiment, an example in which the fixing member is fixed at a position different from that in the third embodiment will be described.

The fourth embodiment will be described referring to FIGS. 25 and 26.

Figure 25:
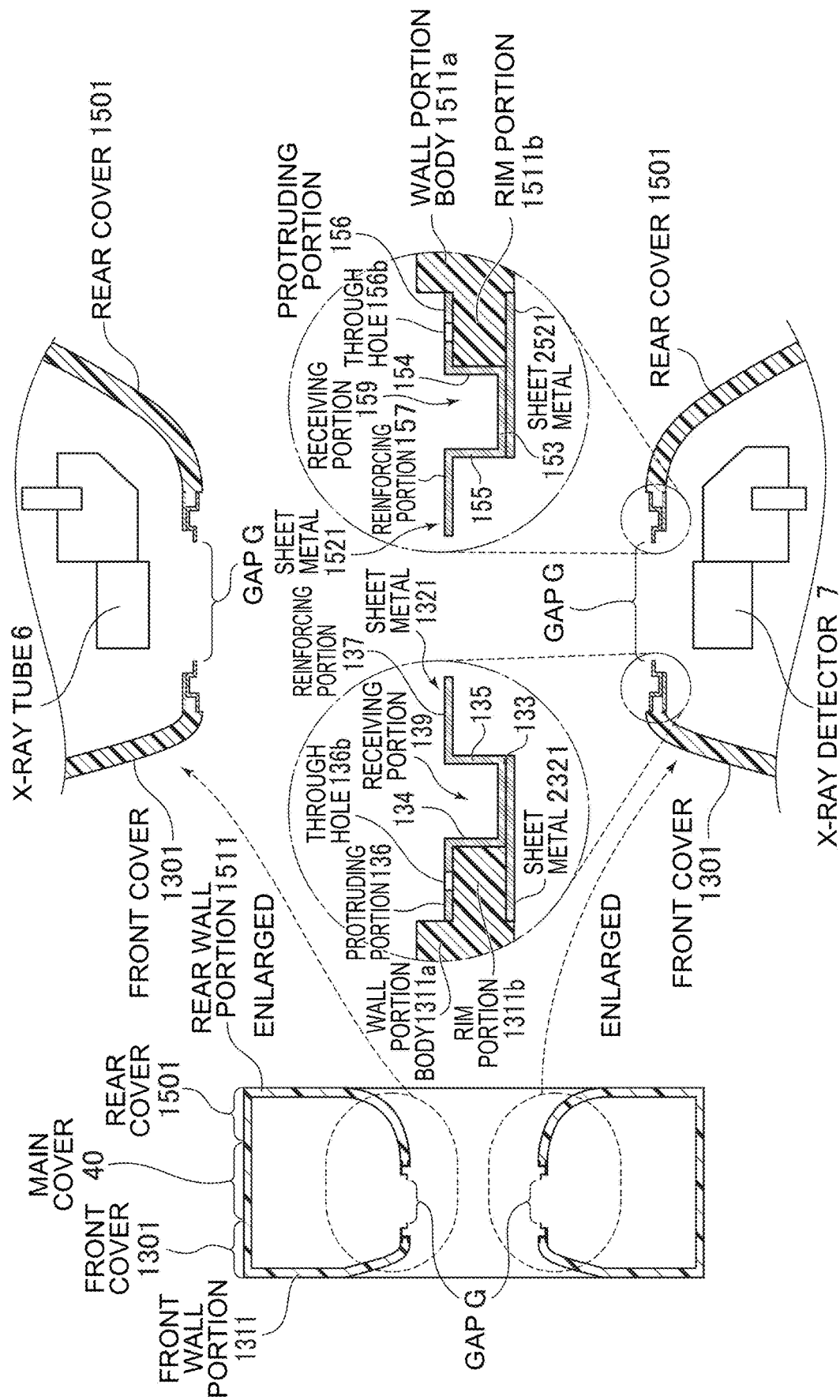
FIG. 25 A view showing a front cover 1301 and a rear cover 1501 before being fitted with the scan window 60.

FIG. 25 is a view showing a front cover 1301 and a rear cover 1501 before being fitted with the scan window 60.

In the fourth embodiment, a front wall portion 1311 of the front cover 1301 is constructed to have a wall portion body 1311a and a rim portion 1311b. The rim portion 1311b is thinly formed to have a thickness about half that of the wall portion body 1311a.

The front cover 1301 also has two sheet metals 1321 and 2321. The sheet metal 2321 has the same structure as that of the sheet metal 232 (see FIG. 19) in the second embodiment. On the other hand, compared with the sheet metal 132 (see FIG. 19) in the second embodiment, the sheet metal 1321 is different therefrom in the following points:

(1) The sheet metal 1321 is processed so that the two side portions 134 and 135 have the same height; and (2) The sheet metal 1321 is formed with a through hole 136b for passing a screw therethrough into the protruding portion 136.

Next, the rear cover 1501 will be described.

A rear wall portion 1511 of the rear cover 1501 is constructed to have a wall portion body 1511a and a rim portion 1511b. The rim portion 1511b is thinly formed to have a thickness about half that of the wall portion body 1511a.

The rear cover 1501 has two sheet metals 1521 and 2521. The sheet metal 2521 has the same structure as that of the sheet metal 252 (see FIG. 20) in the second embodiment. On the other hand, compared with the sheet metal 152 (see FIG. 20) in the second embodiment, the sheet metal 1521 is different therefrom in the following points:

(1) The sheet metal 1521 is processed so that the two side portions 154 and 155 have the same height; and (2) The sheet metal 1521 is formed with a through hole 156b for passing a screw therethrough into the protruding portion 156.

Figure 26:
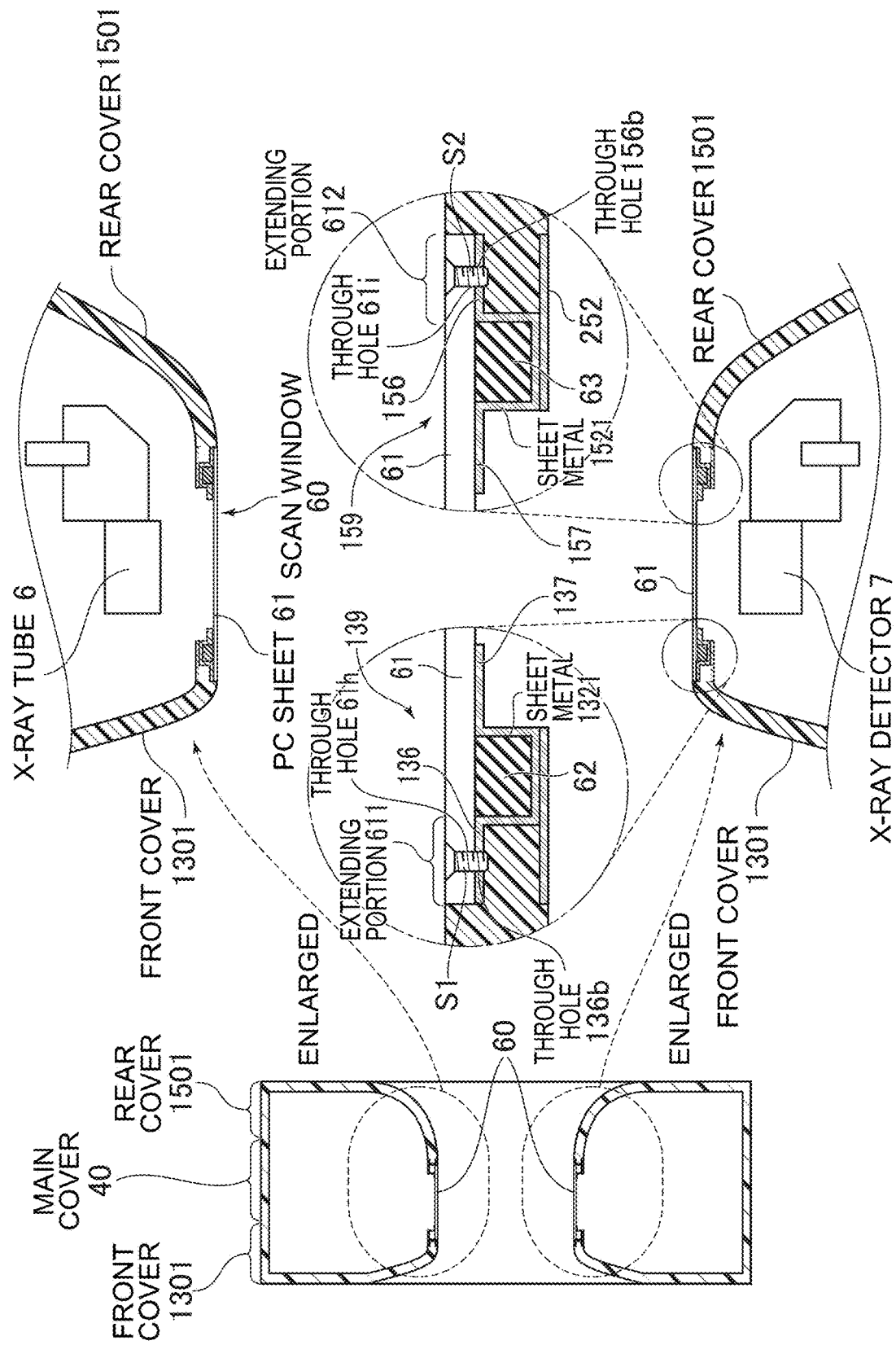
FIG. 26 A view showing a state after the front cover 1301 and rear cover 1501 are fitted with the scan window 60.

The scan window 60 is fitted in the thus-constructed front cover 1301 and rear cover 1511 (see FIG. 26).

FIG. 26 is a view showing a state after the front cover 1301 and rear cover 1501 are fitted with the scan window 60.

In the fourth embodiment, the PC sheet 61 has an extending portion 611 covering the protruding portion 136 of the sheet metal 1321, and an extending portion 612 covering the protruding portion 156 of the sheet metal 1521. The extending portion 611 of the PC sheet 61 is formed with a through hole 61h for passing a screw therethrough at a position corresponding to the through hole 136b in the protruding portion 136. The extending portion 612 of the PC sheet 61 is formed with a through hole 61i for passing a screw therethrough at a position corresponding to the through hole 156b in the protruding portion 156.

In fitting the scan window 60 in the front cover 1301 and rear cover 1501 in the fourth embodiment, a worker can register the through hole 61h in the scan window 60 in communication with the through hole 136b in the protruding portion 136 of the sheet metal 1321, and further, register the through hole 61i in the scan window 60 in communication with the through hole 156b in the protruding portion (reinforcing portion) 156 of the sheet metal 1521.

After fitting the scan window 60 in the front cover 1301 and rear cover 1501, the worker screws a screw S1 into the through holes 61h and 136b, and a screw S2 into the through holes 61i and 156b. The screw S1 fixes the scan window 60 to the front cover 1301 in a portion on a side opposite to the reinforcing portion 137 with respect to the receiving portion 139. The screw S2 fixes the scan window 60 to the rear cover 1501 in a portion on a side opposite to the reinforcing portion 157 with respect to the receiving portion 159. Since the PC sheet 61 is thus firmly fixed to the protruding portion 136 of the sheet metal 1321 and the protruding portion 156 of the sheet metal 1521, deformation of the PC sheet 61 can be further reduced.

Compared with the third embodiment, the fourth embodiment can bring the positions of the screws S1 an S2 farther away from the rotating elements, such as the X-ray tube 6 and X-ray detector 7. Therefore, in the case that it is difficult to reserve sufficient space for protruding the tips of the screws S1 and S2 near the rotating elements, the fourth embodiment may be adopted to thereby firmly fix the PC sheet 61 to the front cover 130 and rear cover 150.

(5) Fifth Embodiment

Compared with the CT apparatus in the first to fourth embodiments, the CT apparatus in a fifth embodiment has a front cover and a rear cover of different construction and a scan window of different construction; however, other constructions are the same. Accordingly, in the description of the fifth embodiment, the front cover and rear cover, and scan window will be mainly addressed.

Figure 27:
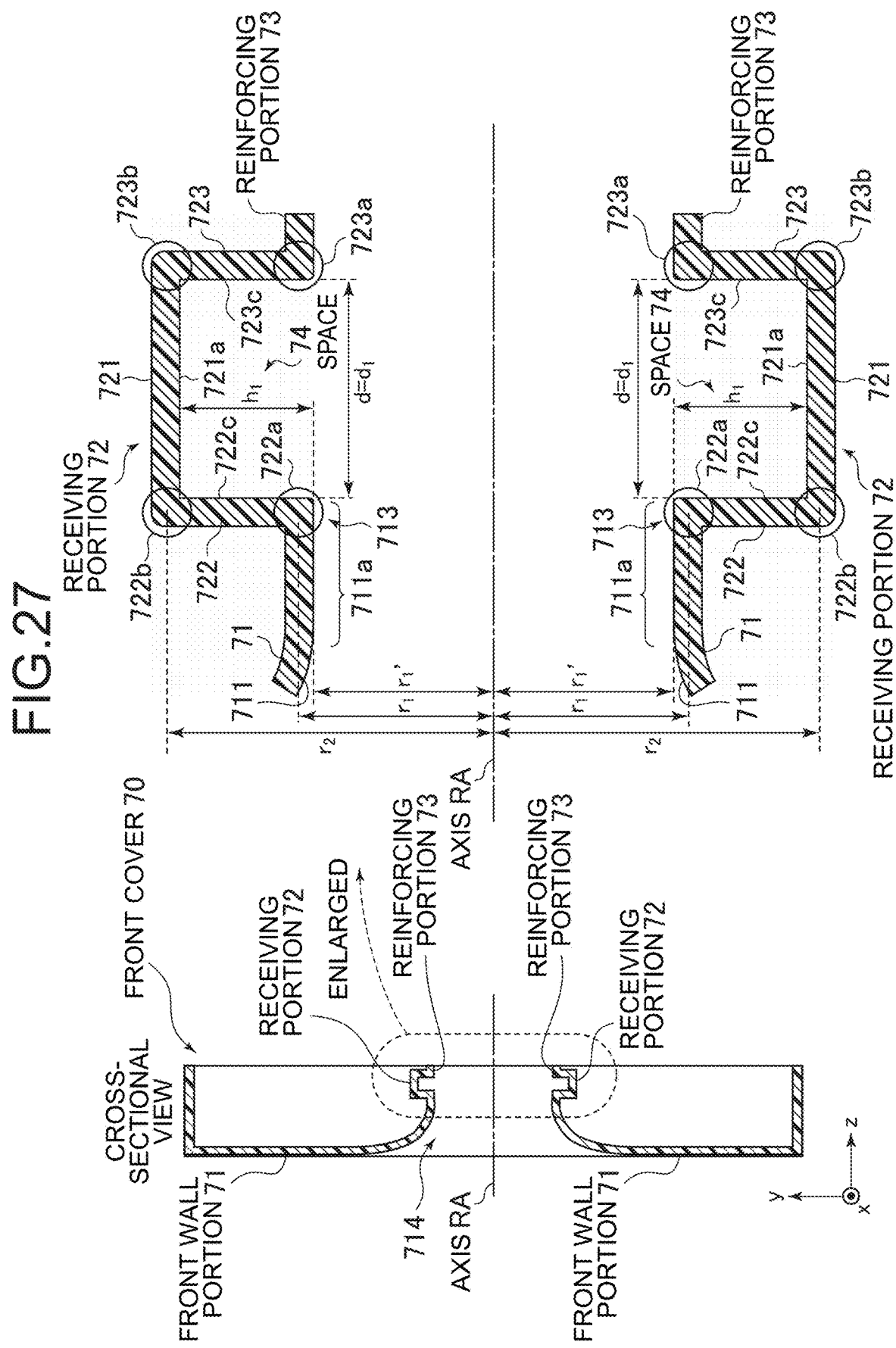
FIG. 27 An explanatory view of a front cover 70 in a fifth embodiment.

FIG. 27 is an explanatory view of a front cover 70 in the fifth embodiment.

In FIG. 27 are shown a cross-sectional view of the front cover 70, and an enlarged view of a receiving portion 72 and a reinforcing portion 73. It should be noted that in FIG. 27, the size of the receiving portion 72 and reinforcing portion 73 is exaggerated relative to the lengths of radii r1, r1' and r2 in order that the structure of the receiving portion 72 and reinforcing portion 73 is visually comprehensible.

The front cover 70 has a front wall portion 71, a receiving portion 72, and a reinforcing portion 73. The front wall portion 71, receiving portion 72, and reinforcing portion 73 are formed integrally with one another.

The front wall portion 71 has a wall surface 711. The wall surface 711 has a peripheral portion 713 lying along the circumference of a circle of radius r1' around the axis RA. The wall surface 711 defines an opening 714 for forming space in which the subject can be moved. The opening 714 is formed to allow the subject to be moved thereinto.

Moreover, a surface 711a of the wall surface 711 on the side of the receiving portion 72 is formed so that a distance between the surface 711a and axis RA has a constant value (r1') all the way in the direction along the axis RA.

Next, the receiving portion 72 and reinforcing portion 73 will be described.

The receiving portion 72 is formed integrally with the peripheral portion 713 of the front wall portion 71. The receiving portion 72 has a base portion 721, a first side portion 722, and a second side portion 723.

The base portion 721 has a ring shape extending along the circumference of a circle of radius r2 around the axis RA.

The first side portion 722 has a ring shape extending along the peripheral portion 713 of the front wall portion 71. The first side portion 722 has an inner edge portion 722a extending along the circumference of a circle of radius r1 around the axis RA, and an outer edge portion 722b extending along the circumference of a circle of radius r2 around the axis RA. The inner edge portion 722a is formed integrally with the peripheral portion 713 of the front wall portion 71, while the outer edge portion 722b is formed integrally with the base portion 721.

The second side portion 723 is formed to face the first side portion 722 in the z-direction. The second side portion 723 has an inner edge portion 723a extending along the circumference of a circle of radius r1 around the axis RA, and an outer edge portion 723b extending along the circumference of a circle of radius r2 around the axis RA. The outer edge portion 723b is formed integrally with the base portion 721.

The base portion 721 has an interior wall surface 721a, the first side portion 722 has an interior wall surface 722c, and the second side portion 723 has an interior wall surface 723c. The interior wall surfaces 722c and 723c are set to the same height h (=h1), and a distance d between the interior wall surfaces 722c and 723c is set as d=d1.

Space 74 surrounded by these interior wall surfaces 721a, 722c, and 723c is used as space in which an elastic member 92 of the scan window 90 described later (see FIG. 30) is to be disposed.

Next, the reinforcing portion 73 will be described.

The reinforcing portion 73 is formed to extend along the circumference of a circle of radius r1 around the axis RA. The reinforcing portion 73 is formed to protrude in a direction away from the first side portion 722 with respect to the second side portion 723. The reinforcing portion 73 is formed integrally with the inner edge portion 723a of the second side portion 723. The reinforcing portion 73 is for reinforcing a PC sheet 91 (see FIG. 30) of the scan window 90 so that deformation of the PC sheet 91 is reduced.

The front cover 70 is constructed as above. Next, the rear cover will be described.

Figure 28:
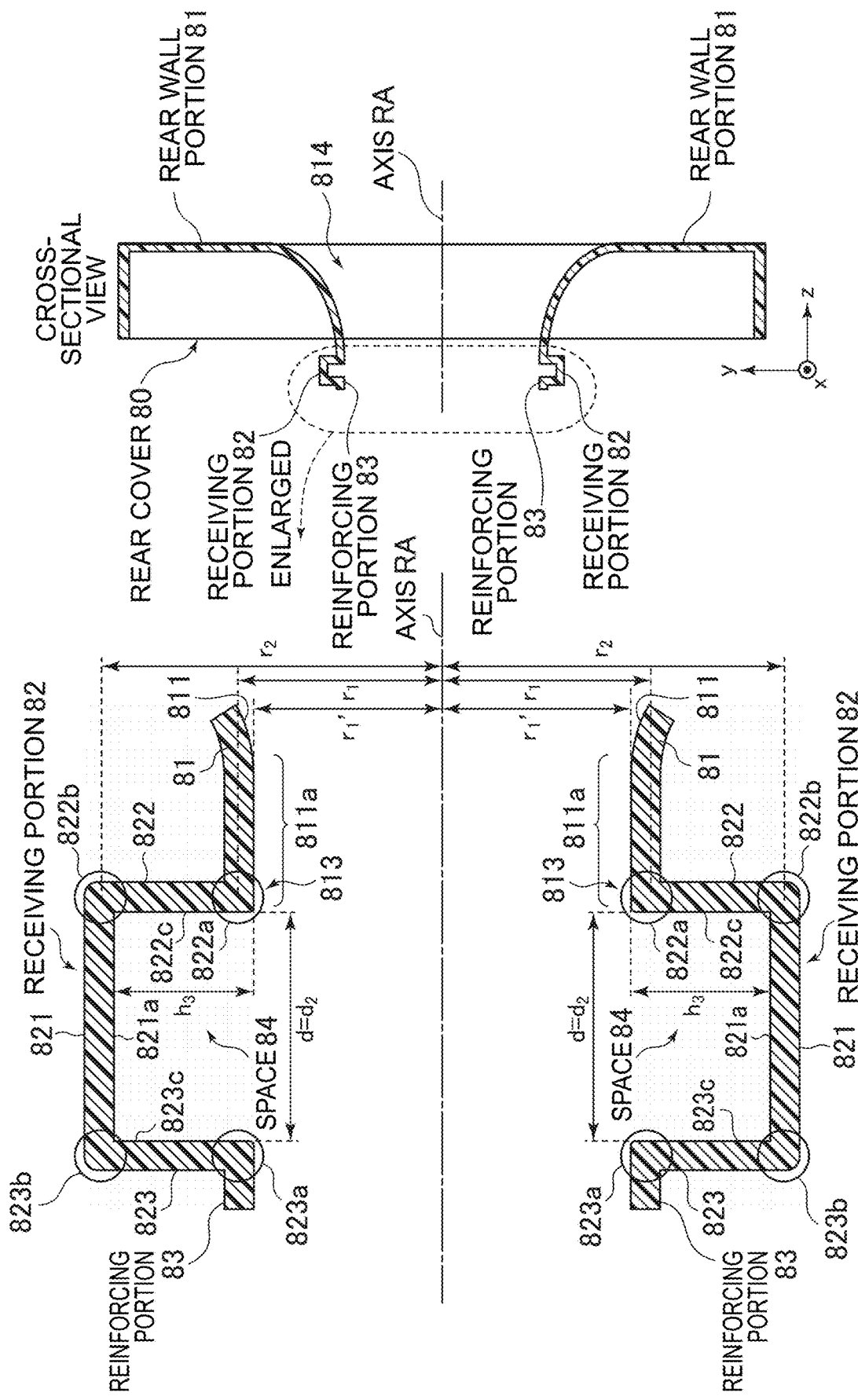
FIG. 28 An explanatory view of a rear cover 80 in the fifth embodiment.

FIG. 28 is an explanatory view of a rear cover 80 in the fifth embodiment.

In FIG. 28 are shown a cross-sectional view of the rear cover 80, and an enlarged view of a receiving portion 82 and a reinforcing portion 83. It should be noted that in FIG. 28, the size of the receiving portion 82 and reinforcing portion 83 is exaggerated relative to the lengths of the radii r1, r1' and r2 in order that the structure of the receiving portion 82 and reinforcing portion 83 is visually comprehensible.

The rear cover 80 has a rear wall portion 81, a receiving portion 82, and a reinforcing portion 83. The rear wall portion 81, receiving portion 82, and reinforcing portion 83 are formed integrally with one another.

The rear wall portion 81 has a wall surface 811. The wall surface 811 has a peripheral portion 813 lying along the circumference of a circle of radius r1' around the axis RA. The wall surface 811 defines an opening 814 forming space in which the subject can be moved. The opening 814 is formed to allow the subject to be moved thereinto.

Moreover, a surface 811a of the wall surface 811 on the side of the receiving portion 82 is formed so that a distance between the surface 811a and axis RA has a constant value (r1') all the way in the direction along the axis RA.

Next, the receiving portion 82 and reinforcing portion 83 will be described.

The receiving portion 82 is formed integrally with the peripheral portion 813 of the rear wall portion 81. The receiving portion 82 has a base portion 821, a third side portion 822, and a fourth side portion 823.

The third side portion 822 has a ring shape extending along the peripheral portion 813 of the rear wall portion 81. The third side portion 822 has an inner edge portion 822a extending along the circumference of a circle of radius r1 around the axis RA, and an outer edge portion 822b extending along the circumference of a circle of radius r2 around the axis RA. The inner edge portion 822a is formed integrally with the peripheral portion 813 of the rear wall portion 81, while the outer edge portion 822b is formed integrally with the base portion 821.

The fourth side portion 823 is formed to face the third side portion 822 in the z-direction. The fourth side portion 823 has an inner edge portion 823a extending along the circumference of a circle of radius r1 around the axis RA, and an outer edge portion 823b extending along the circumference of a circle of radius r2 around the axis RA. The outer edge portion 823b is formed integrally with the base portion 821.

The base portion 821 has an interior wall surface 821a, the third side portion 822 has an interior wall surface 822c, and the fourth side portion 823 has an interior wall surface 823c. The interior wall surface 822c and 823c are set to the same height h (=h3), and a distance d the interior wall surfaces 822c and 823c is set as d=d2.

Space 84 surrounded by these interior wall surfaces 821a, 822c, and 823c is used as space in which an elastic member 93 of the scan window 90 described later (see FIG. 30) is to be disposed.

Next, the reinforcing portion 83 will be described.

The reinforcing portion 83 is formed to extend along the circumference of a circle of radius r1 around the axis RA. The reinforcing portion 83 is formed to protrude in a direction away from the third side portion 822 with respect to the fourth side portion 823. The reinforcing portion 83 is formed integrally with the inner edge portion 823a of the fourth side portion 823. The reinforcing portion 83 reinforces the PC sheet 91 (see FIG. 30) of the scan window 90 described later, so that deformation of the PC sheet 91 is reduced.

The rear cover 80 is constructed as above.

Figure 29:
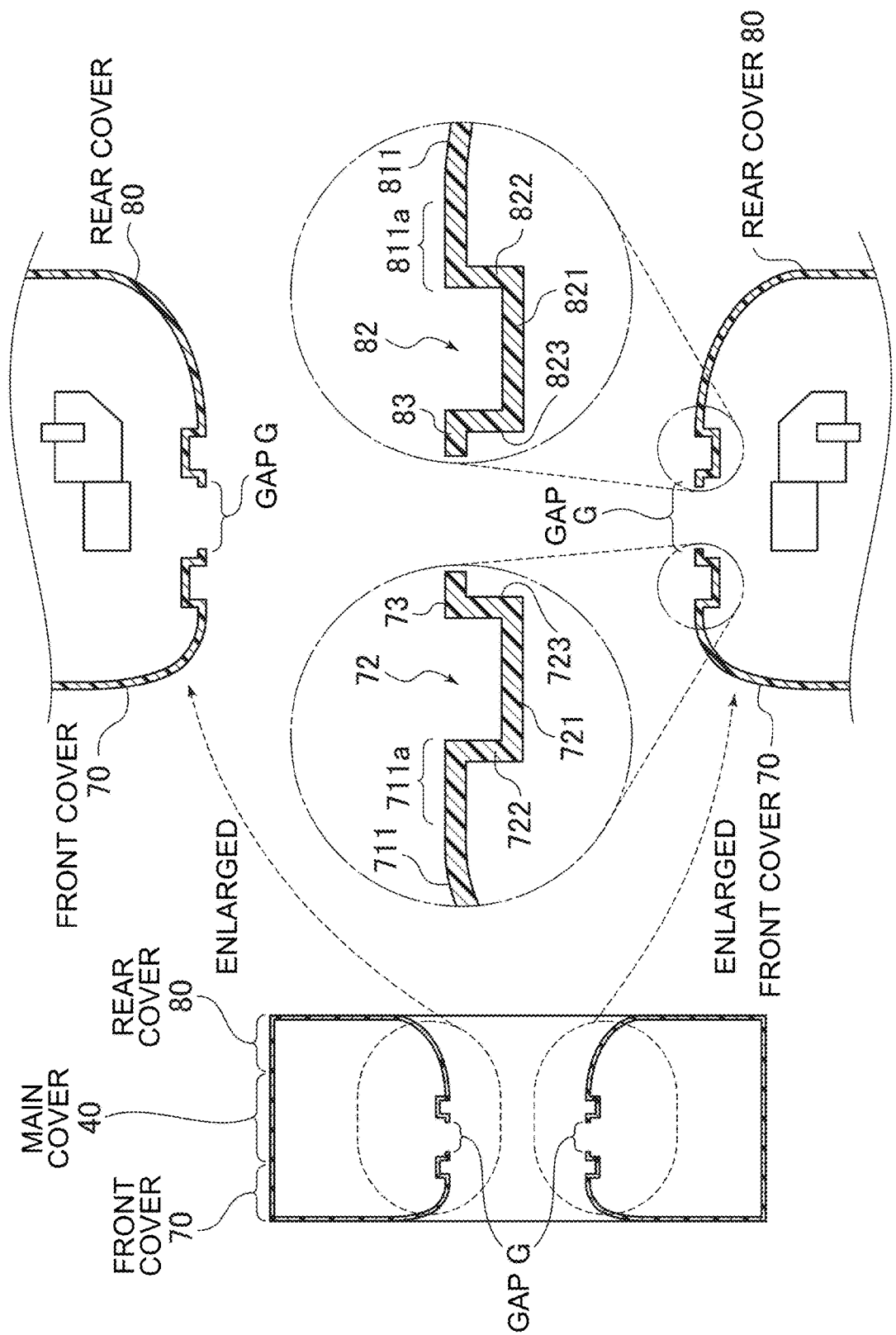
FIG. 29 A view showing the front cover 70 fixed on the side of the front surface of the main cover 40, and the rear cover 80 fixed on the side of the back surface of the main cover 40.

The thus-constructed front cover 70 and rear cover 80 are fixed to the main cover 40 (see FIG. 29).

FIG. 29 shows a view showing a state in which the front cover 70 is fixed on the side of the front surface of the main cover 40, and the rear cover 80 is fixed on the side of the back surface of the main cover 40.

In FIG. 29 is shown a cross-sectional view of the front cover 70, main cover 40, and rear cover 80.

By the front cover 70 and rear cover 80 being fixed to the main cover 40, a gap G is formed between the opening of the front cover 70 and the opening of the rear cover 80, as shown in FIG. 29.

Next, a structure of the scan window will be described.

FIGS. 30 to 33 are explanatory views of the scan window 90.

Figure 30:
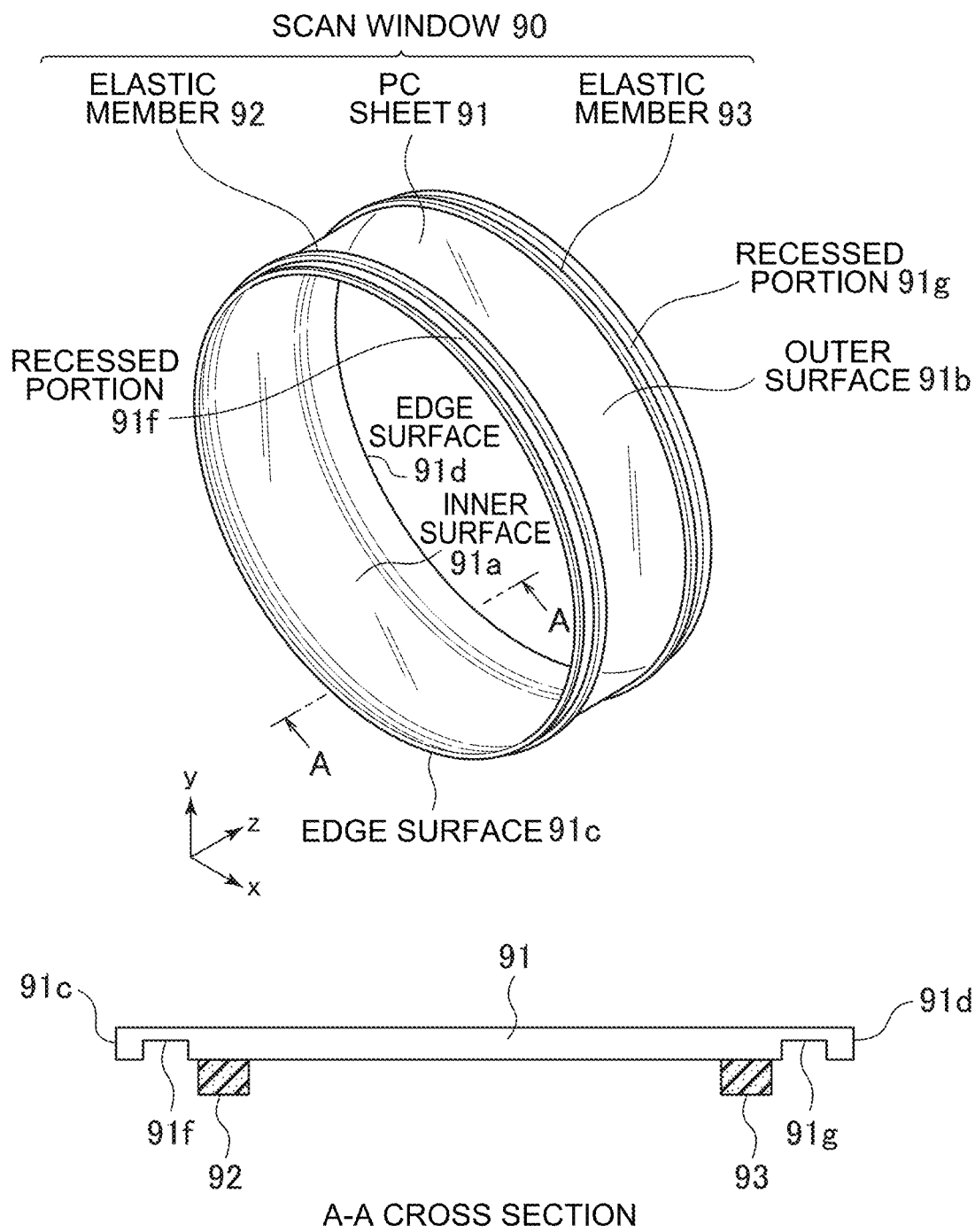
FIG. 30 A perspective view and an A-A cross-sectional view of a scan window 90.
Figure 31:
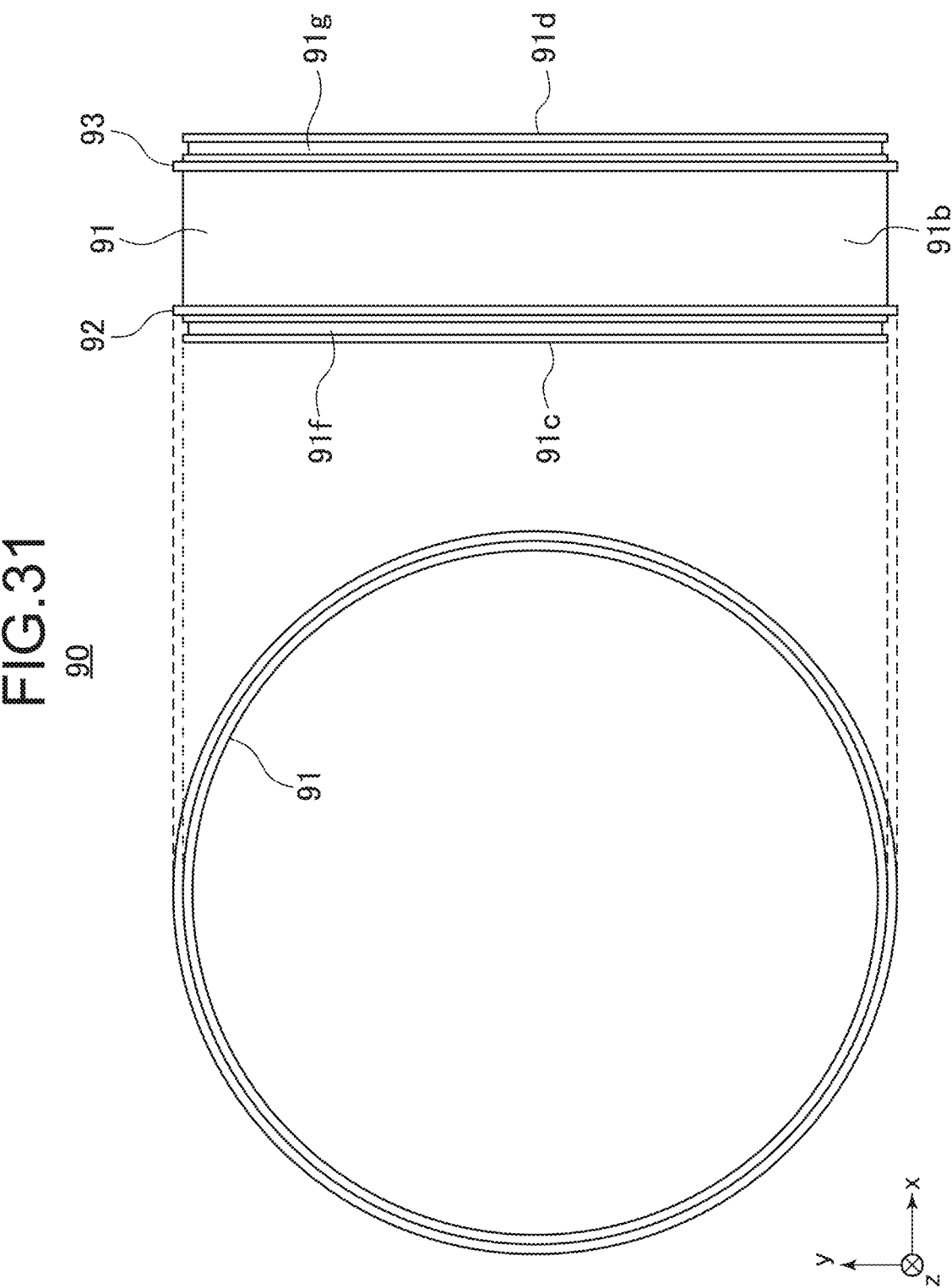
FIG. 31 A front elevational view and a side view of the scan window 90.

FIG. 30 is a perspective view of the scan window 90, and FIG. 31 illustrates a front elevational view and a side view of the scan window 90.

The scan window 90 has a generally cylindrical shape. Now several components constituting the scan window 90 will be described.

Figure 32:
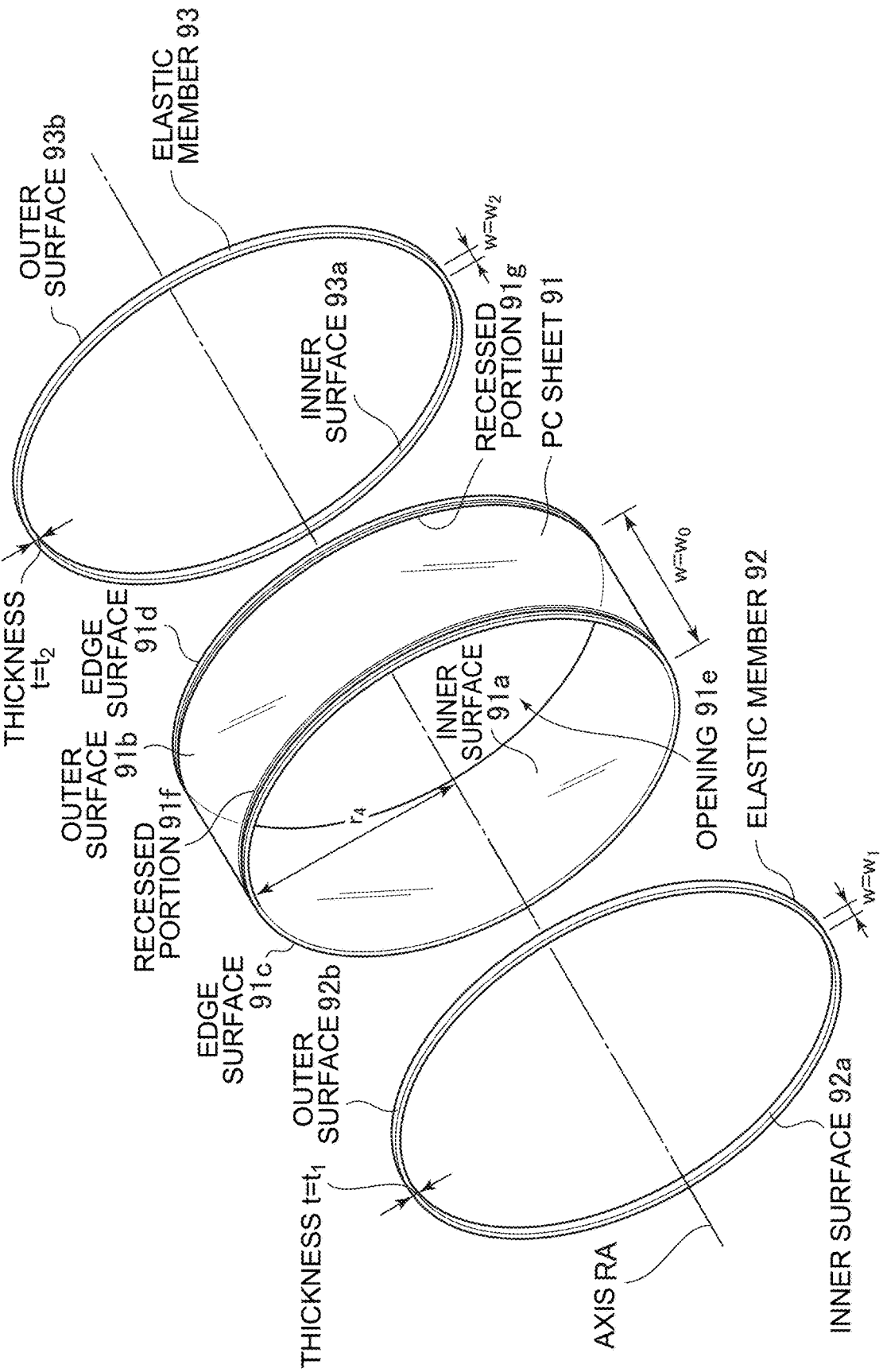
FIG. 32 An exploded perspective view of the scan window 90.

FIG. 32 is an exploded perspective view of the scan window 90.

The scan window 90 has a PC sheet 91, and elastic members 92 and 93.

FIG. 33 illustrates a perspective view and an A-A cross-sectional view of the PC sheet 91.

The PC sheet 91 is a sheet formed of polycarbonate, which is X-ray transparent and is deformable. The PC sheet 91 is for use as a window member having an X-ray transparent window. The PC sheet 91 has a ring shape along the circumference of a circle of radius r4 around the axis RA. The radius r4 may be set to a value within a range of 30 to 40 cm, for example.

The PC sheet 91 is formed to have a thickness of the order of 0.1 to several millimeters. Moreover, the PC sheet 91 is formed to have a width w in the direction of the axis RA set as w=w0. The width w=w0 may be set to a value within a range of 10 to 30 cm, for example.

The PC sheet 91 has an inner surface 91a and an outer surface 91b. The inner surface 91a of the PC sheet 91 defines an opening 91e for forming space in which the subject can be moved. The opening 91e is formed to allow the subject to be moved thereinto. On the other hand, the outer surface 91b of the PC sheet 91 is a surface for defining the space 9 for movement of the rotating section 5 (see FIG. 3). It should be noted that it is also possible to coat part of the PC sheet 61 with a material that prevents X-ray transmission in order to limit the z-extent of the X-rays emitted from the X-ray tube 6.

Moreover, the PC sheet 91 has two edge surfaces 91c and 91d facing mutually opposite sides.

The PC sheet 91 is formed in its outer surface 91b with two recessed portions 91f and 91g. The recessed portion 91f is formed alongside of the edge surface 91c, while the recessed portion 91g is formed alongside of the edge surface 91d. A portion of the PC sheet 91 formed with the recessed portion 91f has a thickness smaller than an end portion 91h of the PC sheet 91, and a portion of the PC sheet 91 formed with the recessed portion 91g has a thickness smaller than an end portion 91i of the PC sheet 91.

Next, the elastic members 92 and 93 will be described referring to FIG. 32.

The elastic member 92 has a ring shape. The elastic member 92 also has an inner surface 92a and an outer surface 92b. The inner surface 92a of the elastic member 92 is used as a joint surface joined to the outer surface 91b of the PC sheet 91. The elastic member 92 is formed to have a thickness t set as t=t1, and a width w set as w=w1. The thickness t1 may be set to a value of several millimeters, for example, and w1 may be set to a value of several to several tens of millimeters, for example. The elastic member 92 is constructed so that it can be disposed into the receiving portion 72 of the front cover 70 (see FIG. 27). The thickness t1 of the elastic member 92 is set to a value slightly larger than the height h1 of the receiving portion 72 (see FIG. 27). The width w1 of the elastic member 92 is set to a value smaller than the distance d1 of the receiving portion 72 (see FIG. 27) (e.g., w1=0.7d1).

Next, the elastic member 93 will be described.

The elastic member 93 has a ring shape. The elastic member 93 also has an inner surface 93a and an outer surface 93b. The inner surface 93a of the elastic member 93 is used as a joint surface joined to the outer surface 91b of the PC sheet 91. The elastic member 93 is formed to have a thickness t set as t=t2, and a width w set as w=w2. The thickness t2 may be set to a value of several millimeters, for example, and w2 may be set to a value of several to several tens of millimeters, for example. The elastic member 93 is constructed to be disposed into the receiving portion 82 of the front cover 80 (see FIG. 28). The thickness t2 of the elastic member 93 is set to a value slightly larger than the height h3 of the receiving portion 82 (see FIG. 28). The width w2 of the elastic member 93 is set to a value smaller than the distance d2 of the receiving portion 82 (see FIG. 28) (e.g., w2=0.7d2).

The elastic members 92 and 93 are provided to the PC sheet 91 on the side of the outer surface 91b of the PC sheet 91. In the fifth embodiment, the elastic members 92 and 93 are provided to the PC sheet 91 on the side of the outer surface 91b of the PC sheet 91 by joining the elastic members 92 and 93 to the outer surface 91b of the PC sheet 91. By joining the elastic members 92 and 93 to the outer surface 91b of the PC sheet 91, the scan window 90 is constructed as shown in FIGS. 30 and 31. The elastic member 92 is joined to the outer surface 91b of the PC sheet 91 alongside of the recessed portion 91f of the PC sheet 91 on a side opposite to the edge surface 91c with respect to the recessed portion 91f. On the other hand, the elastic member 93 is joined to the outer surface 91b of the PC sheet 91 alongside of the recessed portion 91g of the PC sheet 91 on a side opposite to the edge surface 91d with respect to the recessed portion 91g. The elastic members 92 and 93 may be joined to the PC sheet 91 by a double-sided tape or an adhesive, for example.

The elastic members 92 and 93 are members for preventing liquid from penetrating to the inside of the gantry 2 from the outside of the gantry 2. The elastic members 92 and 93 may be formed using a foam material, for example.

Figure 34:
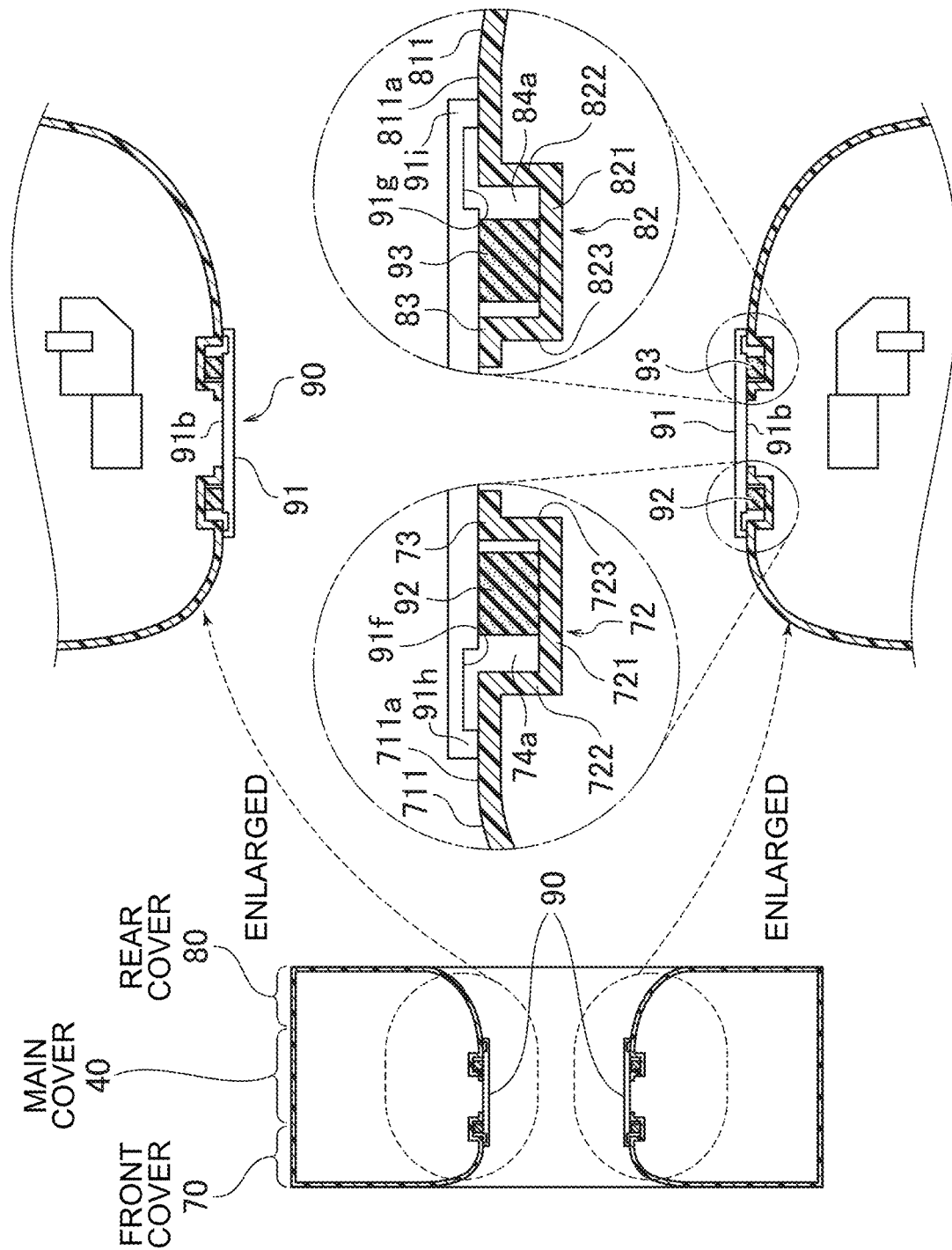
FIG. 34 A view schematically showing a state in which the front cover 70 and rear cover 80 are fitted with the scan window 90.

The thus-constructed scan window 90 is fitted in the front cover 70 and rear cover 80 so as to fill the gap G (see FIG. 29). FIG. 34 is a view schematically showing a state in which the front cover 70 and rear cover 80 are fitted with the scan window 90.

A worker pushes the elastic members 92 and 93 of the scan window 90 into the receiving portions 72 and 82, respectively, so that the elastic members 92 and 93 are disposed in the receiving portions 72 and 73, respectively. The scan window 90 can thus be fitted in the front cover 70 and rear cover 80.

The fifth embodiment, as in the first embodiment, can reduce the risk of liquid penetrating to the inside of the gantry 2 from the outside of the gantry 2, and further, can substantially reduce deformation of the PC sheet.

Moreover, in the fifth embodiment, the scan window 90 fitted in the cover causes the end portion 91h of the PC sheet 91 to come into contact with the surface 711a of the front cover 70, and the end portion 91i of the PC sheet 91 to come into contact with the surface 811a of the rear cover 80 (see FIG. 34). Since the scan window 90 thus covers the receiving portions 72 and 82, and in addition, covers part of the surface 711a of the front cover 70 and part of the surface 811a of the rear cover 80, small pieces of waste such as dust and dirt are less prone to deposit in the receiving portions 72 and 82.

Furthermore, in the fifth embodiment, the end portion 91h of the PC sheet 91 is formed in its proximity with the recessed portion 91f, and the end portion 91i of the PC sheet 91 is formed in its proximity with the recessed portion 91g. Now a reason why the recessed portions 91f and 91g are formed will be described.

In the case that liquid is laid on the end portion 91h of the PC sheet 91 for some reason, the liquid may sometimes penetrate between the end portion 91h of the PC sheet 91 and the surface 711a of the cover by a capillary phenomenon. In the fifth embodiment, however, the end portion 91h of the PC sheet 91 is formed in its proximity with the recessed portion 91f, so that the liquid penetrating between the end portion 91h of the PC sheet 91 and the surface 711a of the cover reaches the inside of the recessed portion 91f. The liquid reaching the inside of the recessed portion 91f is prone to be attached to an interior wall surface of the recessed portion 91f by a surface tension acting on the liquid, so that the liquid is less prone to flow toward a gap 74a between the elastic member 92 and the side portion 722 of the receiving portion 72 from the recessed portion 91f. Since the recessed portion 91f thus performs the function of trapping liquid, the liquid is less prone to accumulate in the gap 74a, thus further reducing the risk of liquid penetrating to the inside of the gantry 2.

Likewise, when liquid penetrates between the end portion 91i of the PC sheet 91 and the surface 811a of the cover, the recessed portion 91g formed in proximity of the end portion 91i of the PC sheet 91 performs the function of trapping the liquid. Since liquid is thus less prone to accumulate in a gap 84a between the elastic member 93 and the side portion 822 of the receiving portion 82, the risk of liquid penetrating to the inside of the gantry 2 can be further reduced.

In addition, when the scan window 90 is fitted in the covers in the fifth embodiment, the width w1 of the elastic member 92 (see FIG. 32) is set to a value smaller than the distance d1 of the receiving portion 72 (see FIG. 27) (e.g., w1=0.7d1) so that the gap 74a is formed between the elastic member 92 and the side portion 722 of the receiving portion 72. Likewise, the width w2 of the elastic member 93 (see FIG. 32) is set to a value smaller than the distance d2 of the receiving portion 82 (see FIG. 28) (e.g., w2=0.7d2) so that the gap 84a is formed between the elastic member 93 and the side portion 822 of the receiving portion 82. Since the elastic members 92 and 93 can be more easily inserted in the receiving portions 72 and 82, respectively, by making the widths of the elastic members 92 and 93 smaller (narrower) as described above, a worker can easily achieve the work of fitting the scan window 90 in the covers. It should be noted that wider elastic members 92 and 93 may be used to prevent creation of the gaps 74a and 84a.

Now an exemplary method of fabricating the scan window 90 will be briefly described.

Figure 35:
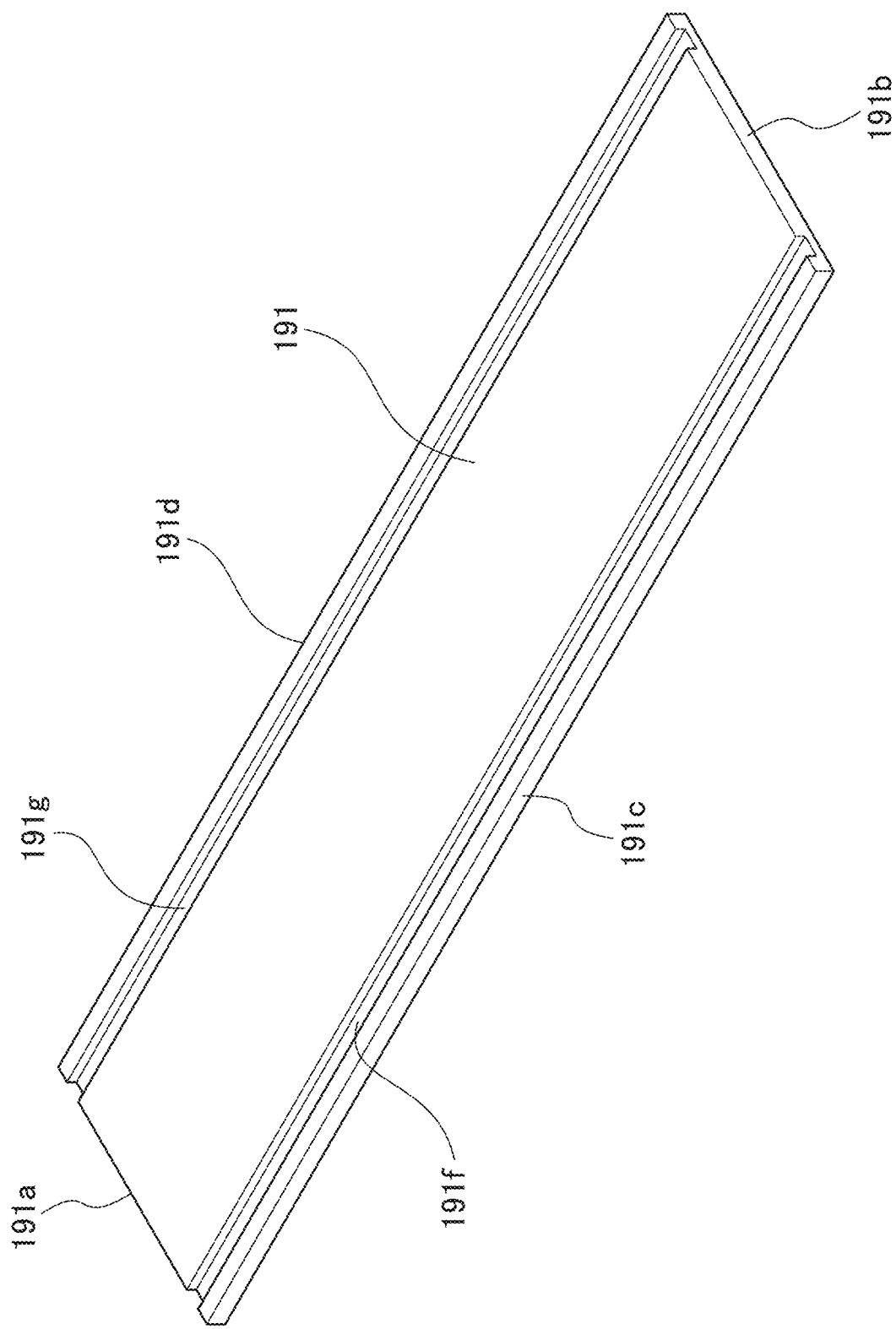
FIG. 35 A perspective view of a sheet strip 191.

FIGS. 35 to 37 are explanatory views of the exemplary method of fabricating the scan window 90.

First, from a mother sheet manufactured using polycarbonate, a band-like sheet strip 191 for use as the PC sheet is prepared. The sheet strip 191 is formed with recessed portions 191f and 191g. The recessed portion 191f is formed alongside of an edge surface 191c of the sheet strip 191, while the recessed portion 191g is formed alongside of an edge surface 191d of the sheet strip 191.

Next, to make the sheet strip 191 ring-shaped, a front edge surface 191a and a rear edge surface 191b of the sheet strip 191 are joined together. By joining the front edge surface 191a and rear edge surface 191b of the sheet strip 191 together, the ring-shaped PC sheet 91 can be fabricated, as shown in FIG. 36.

Next, the PC sheet 91 is joined with the elastic members 92 and 93 (see FIG. 37).

FIG. 37 is a view showing a state in which the PC sheet 91 is joined with the elastic members 92 and 93.

The elastic member 92 is joined to the PC sheet 91 alongside of the recessed portion 91f (191f) of the PC sheet 91, while the elastic member 93 is joined to the PC sheet 91 alongside of the recessed portion 91g (191g) of the PC sheet 91.

Thus, the scan window 90 can be fabricated. It should be noted that the elastic members 92 and 93 may be joined to the sheet strip 191 before joining both the edges 191a and 191b of the sheet strip 191 together. In this case, the scan window 90 can be fabricated by joining both the edges 191a and 191b of the sheet strip 191 together to make the sheet strip 191 having the elastic members 92 and 93 ring-shaped.

It should be noted that because the PC sheet 91 is fabricated by joining both the edges 191a and 191b of the sheet strip 191 together, a joint portion of the PC sheet 91 may sometimes obtain insufficient strength. A possible method for enhancing strength of the joint portion may involve, for example, joining a lining member 101 to the joint portion alongside of the recessed portion 91f to traverse the joint portion, as shown in FIG. 38, and moreover, joining a lining member 102 thereto alongside of the recessed portion 91g to traverse the joint portion. For the lining members 101 and 102, a member made of stainless steel may be used, for example. In FIG. 38, the PC sheet 91 joined with the lining members 101 and 102 makes up the window member. Use of the lining members 101 and 102 can enhance strength of the joint portion.

In FIG. 38, a thickness J1 of a portion in which the PC sheet 91 and the lining member 101 (102) lie over each other is greater than a thickness J2 of the PC sheet 91 per se by the thickness of the lining member. Accordingly, in joining the elastic members 92 and 93 to the outer surface 91b of the PC sheet 91, the lining members 101 and 102 may hamper the work. Then, an example in which the PC sheet is fabricated while preventing the lining members 101 and 102 from hampering joining of the elastic members 92 and 93 will be described below referring to FIGS. 39 to 41.

Figure 39:
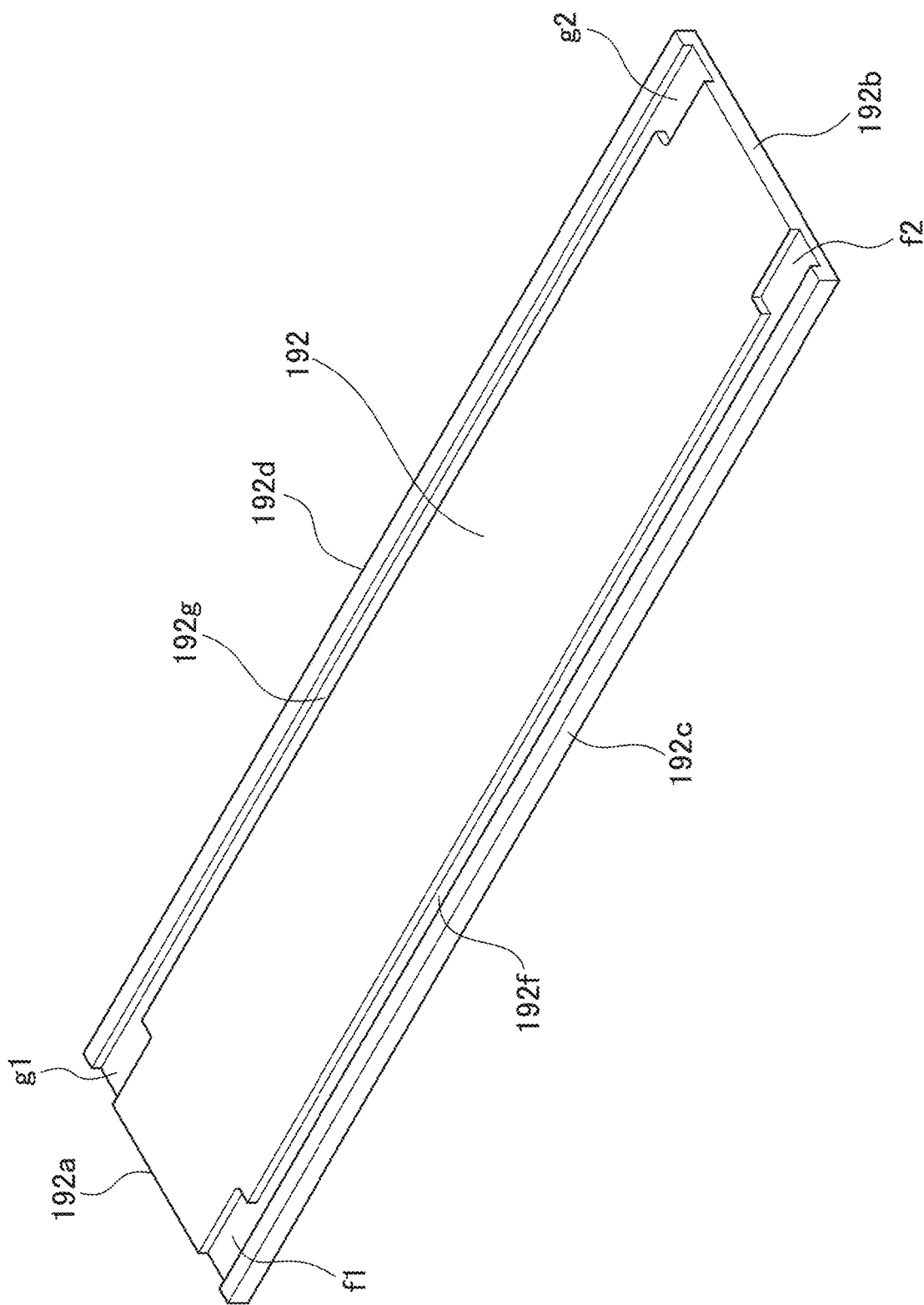
FIG. 39 A perspective view of a sheet strip 192.

First, from a mother sheet manufactured using polycarbonate, a band-like sheet strip 192 for use as the PC sheet is prepared, as shown in FIG. 39. The sheet strip 192 is formed with recessed portions 192f and 192g. The recessed portion 192f is formed alongside of an edge surface 192c of the sheet strip 192, while the recessed portion 192g is formed alongside of an edge surface 192d of the sheet strip 192.

The recessed portion 192f has a portion f1 formed to be wider over a predetermined distance from a front edge surface 192a of the sheet strip 192, and a portion f2 formed to be wider over a predetermined distance from a rear edge surface 192b of the sheet strip 192. Moreover, the recessed portion 192g has a portion g1 formed to be wider over a predetermined distance from the front edge surface 192a of the sheet strip 192, and a portion g2 formed to be wider over a predetermined distance from the rear edge surface 192b of the sheet strip 192.

Next, to make the sheet strip 192 ring-shaped, the front edge surface 192a and rear edge surface 192b of the sheet strip 192 are joined together. By joining the front edge surface 192a and rear edge surface 192b of the sheet strip 192 together, a ring-shaped PC sheet 912 can be fabricated, as shown in FIG. 40.

In FIG. 40, a width w11 of the recessed portions 192f and 192g at the joint portion is wider than a width w12 of the recessed portions 192f and 192g at a portion away from the joint portion.

Next, lining members are joined to the wider portions f1 and f2 of the recessed portion 192f and to the wider portions g1 and g2 of the recessed portion 192g.

FIG. 41 is a view showing a state in which the lining members 101 and 102 are joined.

The PC sheet 912 joined with the lining members 101 and 102 makes up the window member.

The lining members 101 and 102 are formed to have a thickness approximately equivalent to a depth of the recessed portion. Therefore, surfaces of the lining members 101 and 102 may be approximately flush with an outer surface 912a of the PC sheet 912, and thus, in joining the elastic members to the PC sheet 912, the lining members 101 and 102 can be prevented from hampering joining of the elastic members.

(6) Sixth Embodiment

Compared with the CT apparatus in the fifth embodiment, the CT apparatus in a sixth embodiment has a front cover and a rear cover of different structure; however, other structures are the same. Accordingly, in the description of the sixth embodiment, the front cover and rear cover will be mainly addressed.

Compared with the front cover and rear cover in the fifth embodiment, those in the sixth embodiment have basic structures common to the former, and therefore, differences thereof will be mainly addressed.

Figure 42:
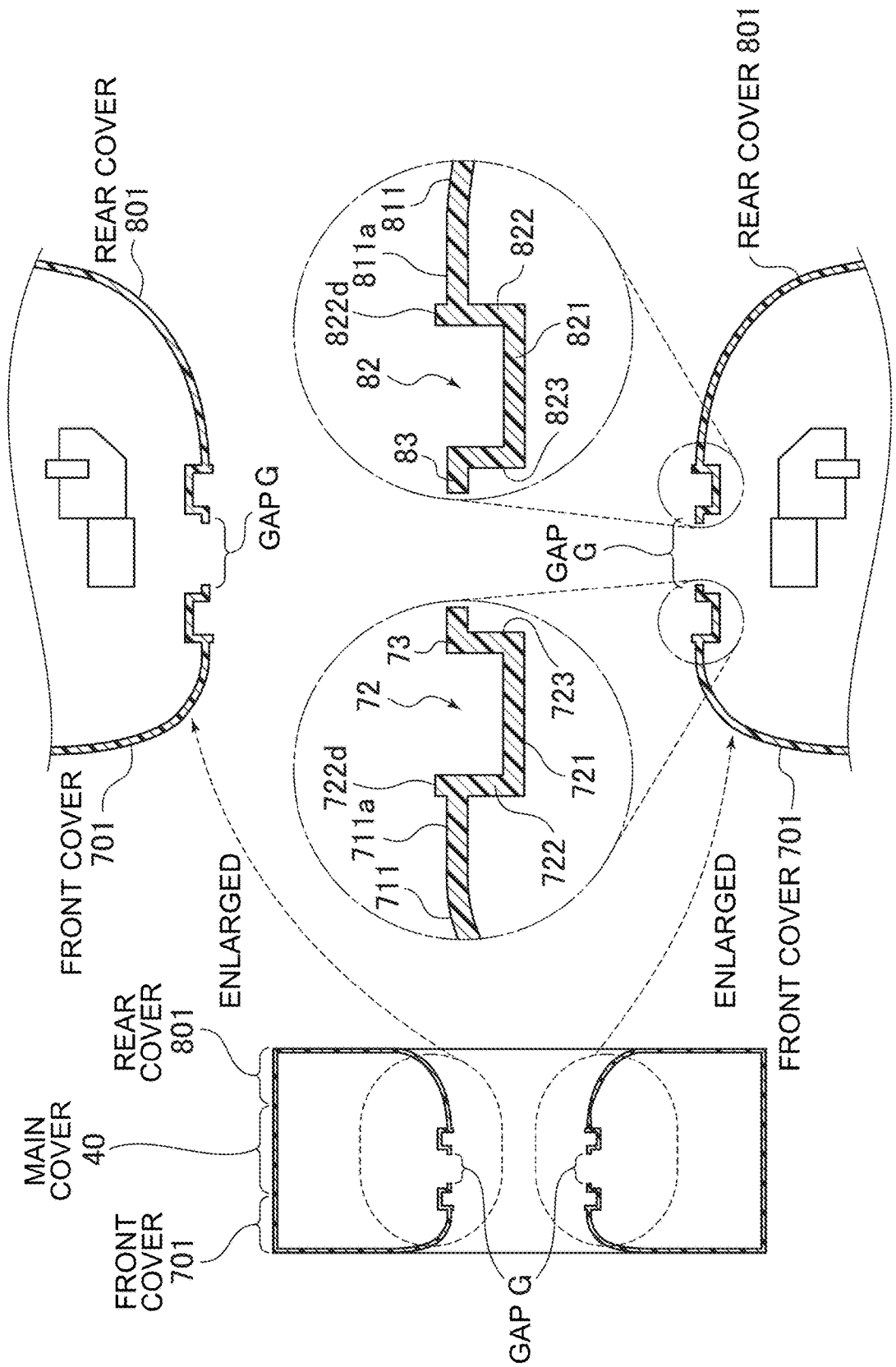
FIG. 42 A view showing a state in which a front cover 701 is fixed on the side of the front surface of the main cover 40, and a rear cover 801 is fixed on the side of the back surface of the main cover 40.

FIG. 42 is an explanatory view of a front cover 701 and a rear cover 801 in the sixth embodiment.

FIG. 42 is a view showing a state in which the front cover 701 is fixed on the side of the front surface of the main cover 40, and the rear cover 801 is fixed on the side of the back surface of the main cover 40.

Compared with the front cover 70 and rear cover 80 in the fifth embodiment, the front cover 701 and rear cover 801 in the sixth embodiment are different therefrom in the following points (a) and (b):

(a) The first side portion 722 is formed to have a ridge portion 722d protruding by a predetermined length relative to the surface 711a of the wall surface 711 on the side of the receiving portion 72; and (b) The third side portion 822 is formed to have a ridge portion 822d protruding by a predetermined length relative to the surface 811a of the wall surface 811 on the side of the receiving portion 82.

Figure 43:
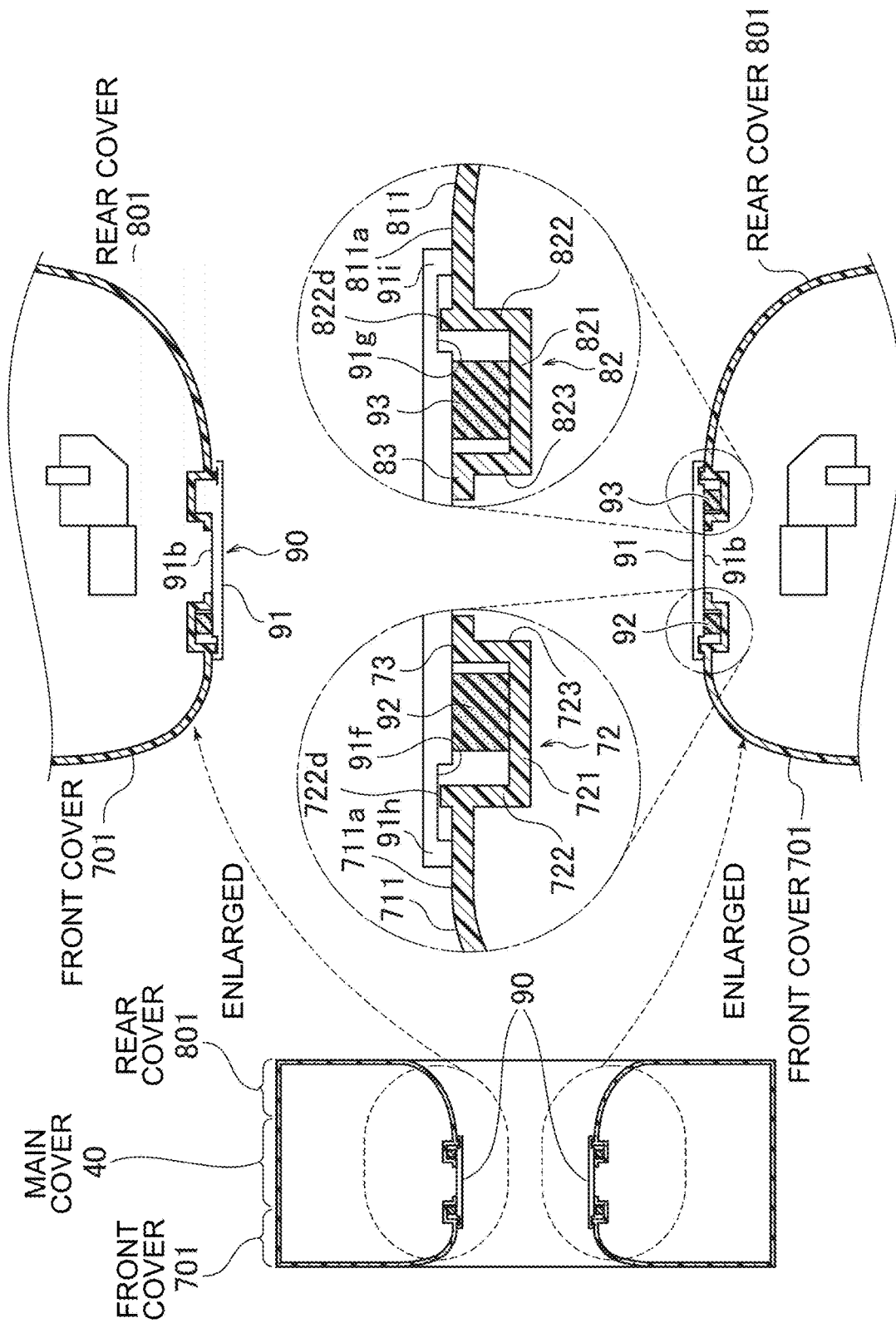
FIG. 43 A view showing a state in which the front cover 701 and rear cover 801 are fitted with the scan window 90.

FIG. 43 is a view showing a state in which the front cover 701 and rear cover 801 are fitted with the scan window 90.

Once the scan window 90 has been fitted, the recessed portions 91f and 91g are positioned to face the ridge portions 722d and 822d, respectively.

Now an effect of the ridge portions 722d and 822d will be described.

The ridge portions 722d and 822d achieve their effect especially in the case that liquid is spilled over the scan window 90 with high liquid pressure, such as a case in which a large amount of liquid is spilled over the scan window 90 by mistake, for example. When liquid is spilled over the scan window 90 with high liquid pressure, a large amount of liquid may flow into the recessed portions 91f and 91g of the PC sheet 91. Even in such a case, since the ridge portions 722d and 822d are provided in the sixth embodiment, the liquid flowing into the recessed portions 91f and 91g are held back by the ridge portions 722d and 822d, respectively. Therefore, even when the amount of liquid flowing into the recessed portions 91f and 91g is large, the risk of the liquid penetrating to the inside of the gantry 2 may be substantially reduced.

(7) Seventh Embodiment

In a seventh embodiment, an example in which receiving portions of shape different from those of the receiving portions in the fifth and sixth embodiments are used will be described.

Figure 44:
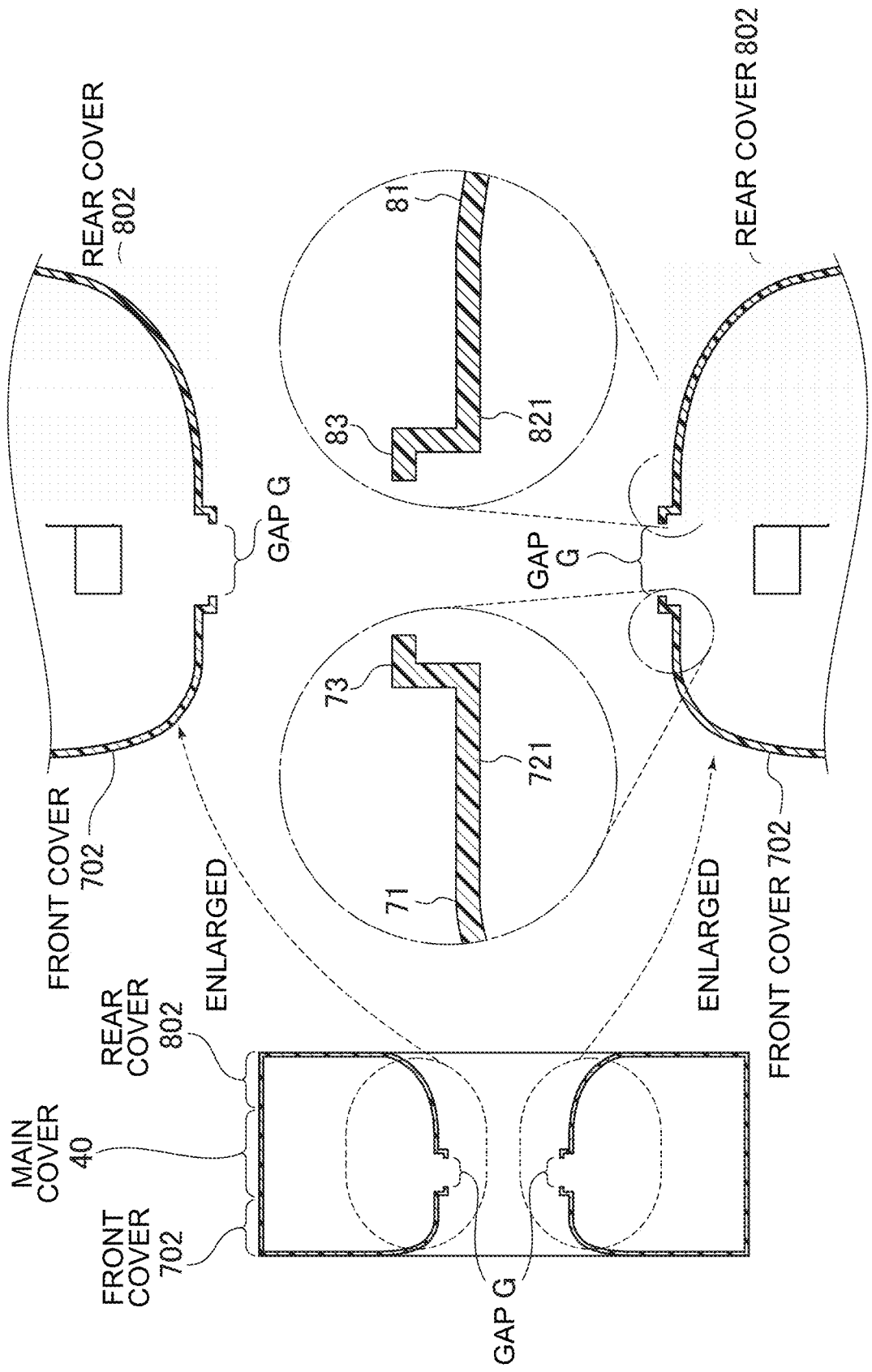
FIG. 44 An explanatory view of a front cover 702 and a rear cover 802 in a seventh embodiment.

FIG. 44 is an explanatory view of a front cover 702 and a rear cover 802 in the seventh embodiment. It should be noted that the front cover 702 and rear cover 802 in the seventh embodiment will be described as compared with the front cover 70 and rear cover 80 in the fifth embodiment.

Compared with the front cover 70 (see FIG. 27) in the fifth embodiment, the front cover 702 in the seventh embodiment is different therefrom in that it does not have the first side portion 722, and the base portion 721 is formed integrally with the front wall portion 71. Similarly, compared with the rear cover 80 (see FIG. 28) in the fifth embodiment, the rear cover 802 in the seventh embodiment is different therefrom in that it does not have the third side portion 822, and the base portion 821 is formed integrally with the front wall portion 81.

Next, the scan window will be described.

Figure 45:
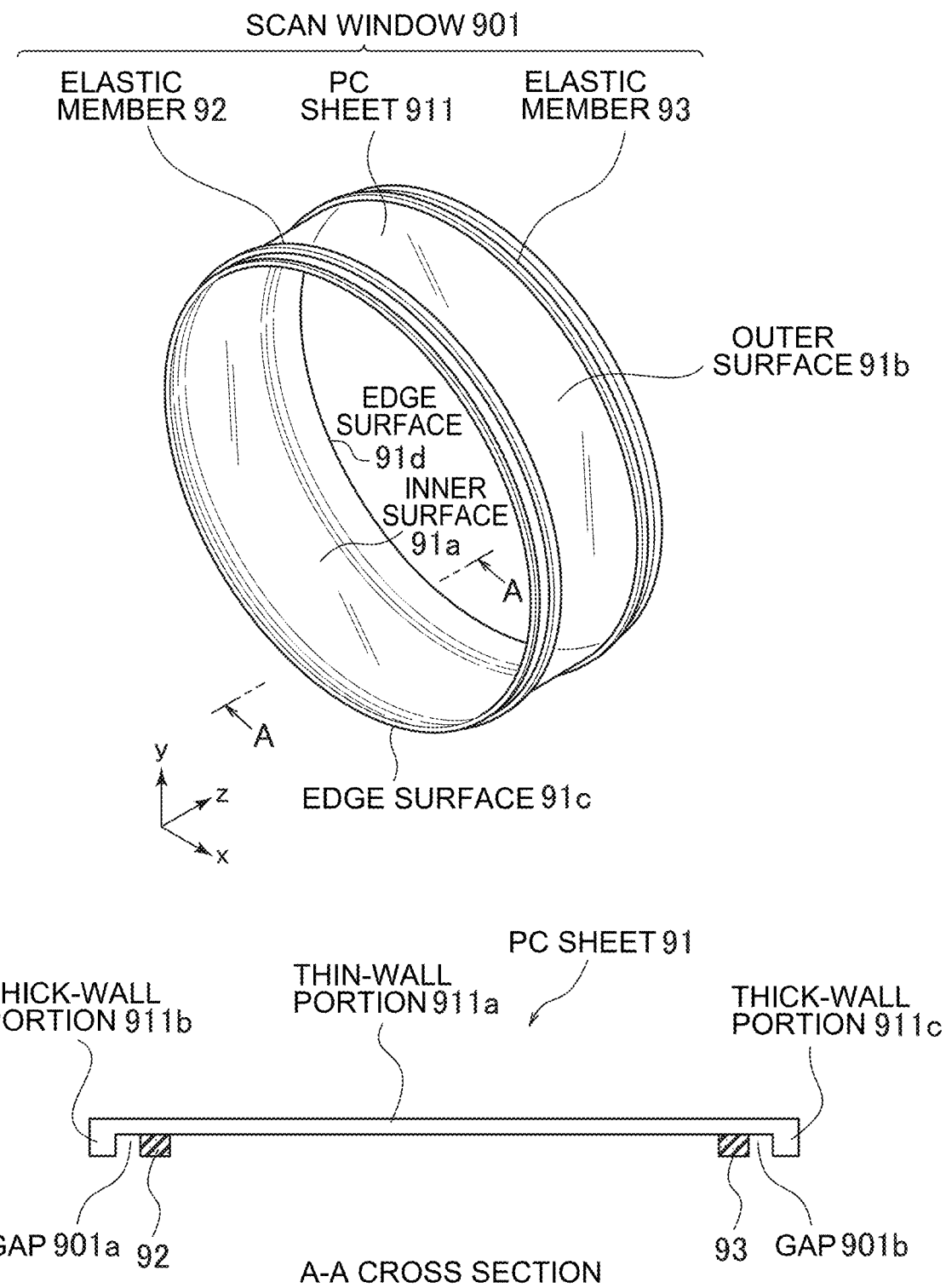
FIG. 45 A perspective view and an A-A cross-sectional view of a scan window 901 in the seventh embodiment.

FIG. 45 shows a perspective view and an A-A cross-sectional view of a scan window 901 in the seventh embodiment.

The scan window 901 has a PC sheet 911 and elastic members 92 and 93.

The PC sheet 911 has a thin-wall portion 911a and thick-wall portions 911b and 911c. The thick-wall portion 911b is formed integrally with one end portion of the thin-wall portion 911b, and the thick-wall portion 911c is formed integrally with the other end portion of the thin-wall portion 911b. The elastic member 92 is provided alongside of the thick-wall portion 911b, and a gap 901a is provided between the elastic member 92 and thick-wall portion 911b. The elastic member 93 is provided alongside of the thick-wall portion 911c, and a gap 901b is provided between the elastic member 93 and thick-wall portion 911c.

Figure 46:
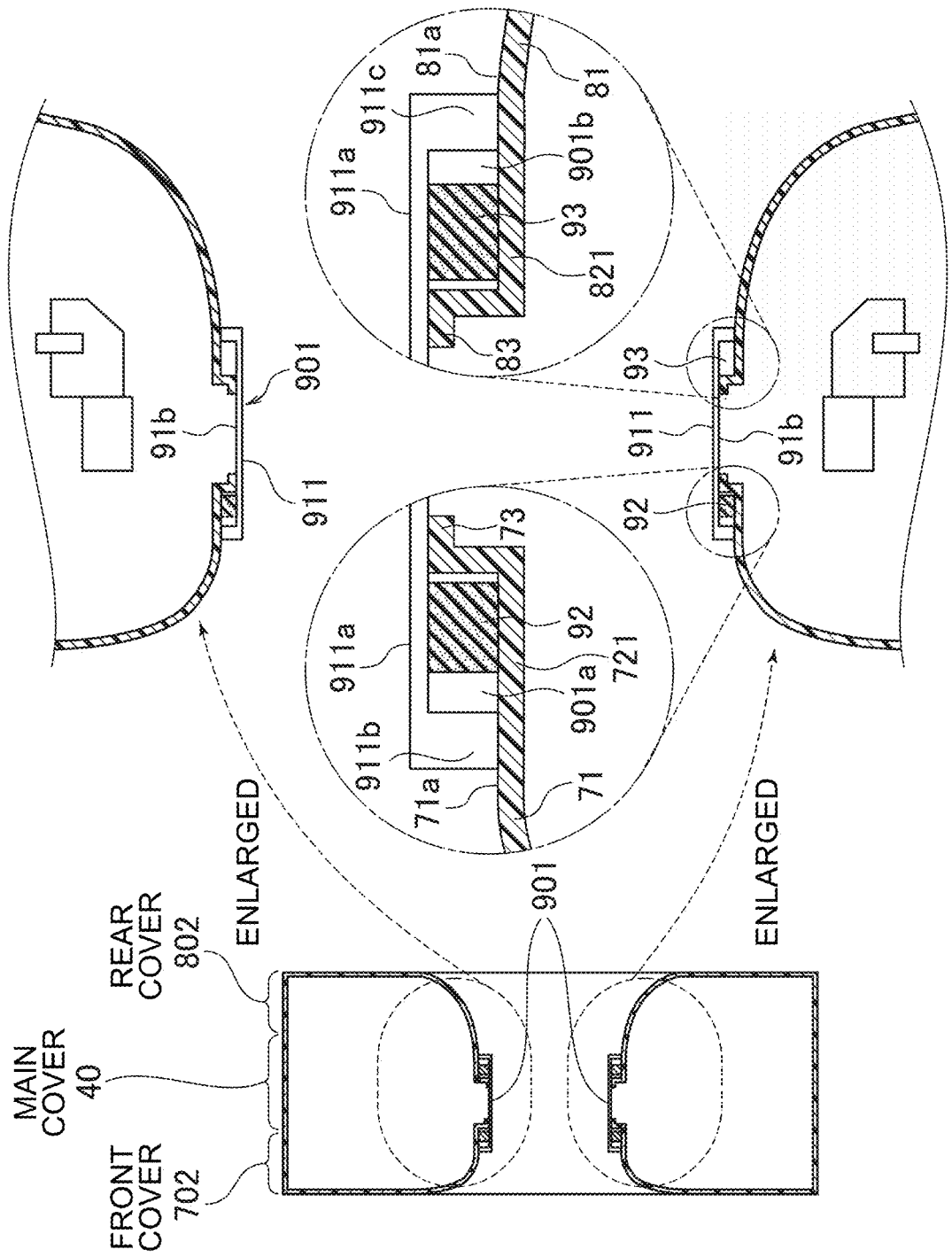
FIG. 46 A view showing a state in which the front cover 702 and rear cover 802 are fitted with the scan window 90.

FIG. 46 is a view showing a state in which the front cover 702 and rear cover 802 are fitted with the scan window 901.

The seventh embodiment, as in the fifth embodiment, can reduce the risk of liquid penetrating to the inside of the gantry 2 from the outside of the gantry 2, and further, can substantially reduce deformation of the PC sheet.

Moreover, in the seventh embodiment, the gap 901a is provided between the elastic member 92 and thick-wall portion 911b. Therefore, liquid penetrating between the thick-wall portion 911b of the PC sheet 911 and a surface 71a of the cover reaches the gap 901a. The liquid reaching the inside of the gap 901a is prone to be attached to a wall surface of the thick-wall portion 911b by a surface tension acting on the liquid, so that the gap 901a performs the function of trapping the liquid, and as a result, the liquid is less prone to flow toward the elastic member 92 from the gap 901a. Likewise, when liquid penetrates between the thick-wall portion 911c of the PC sheet 911 and a surface 81a of the cover, the gap 901b between the elastic member 93 and thick-wall portion 911c performs the function of trapping the liquid, so that the liquid is less prone to flow toward the elastic member 93 from the gap 901b. This can further reduce the risk of liquid penetrating to the inside of the gantry 2.

(8) Eighth Embodiment

Once the scan window has been fitted in the cover, the PC sheet undergoes a force pushing back from the elastic member, which may result in deformation of the PC sheet. In an eighth embodiment, an example in which the PC sheet can be made less prone to deform when it experiences the force pushing back from the elastic member will be described.

Compared with the fifth embodiment, the eighth embodiment is different in the scan window; however, other constructions are the same. Accordingly, in the description of the eighth embodiment, the scan window will be mainly addressed.

FIG. 47 is an explanatory view of a scan window 902 in the eighth embodiment.

Compared with the scan window 90 (see FIG. 34) in the fifth embodiment, the scan window 902 in the eighth embodiment is different therefrom in that there is provided an alloy plate 94 less deformable than the PC sheet 91 between the PC sheet 91 and elastic member 92, and that there is further provided an alloy plate 95 less deformable than the PC sheet 91 between the PC sheet 91 and elastic member 93. These alloy plates 94 and 95 may be formed using stainless steel, for example.

In the eighth embodiment, there are provided the alloy plates 94 and 95 less deformable than the PC sheet 91 between the PC sheet 91 and elastic members 92 and 93. Therefore, when a force pushing the PC sheet 91 back from the elastic members 92 and 93 arises, deformation of the PC sheet 91 may be suppressed because the alloy plates 94 and 95 are less deformable per se.

While the alloy plates 94 and 95 are used to suppress deformation of the PC sheet 91 in the eighth embodiment, any member different from the alloy plates 94 and 95 may be used insofar as it is less deformable than the PC sheet 91.

(9) Ninth Embodiment

FIG. 48 is a view showing elastic members used in a ninth embodiment.

Elastic members 92 and 93 used in the ninth embodiment are formed to have a cross-sectional shape different from that of the elastic members 92 and 93 used in the first to eighth embodiments.

It is possible to form the elastic members 92 and 93 to have any cross-sectional shape insofar as they can reduce the risk of liquid penetrating to the inside of the gantry 2.

DESCRIPTION OF REFERENCE SYMBOLS

2 Gantry
3 Bore
4 Frame
5 Rotating section
6 X-ray tube
7 X-ray detector
8 Rotation support member
20 Housing
30 Front cover
31 Front wall portion
32, 52, 72, 82 Receiving portion
33, 53, 73, 83 Reinforcing portion
34, 54, 74, 84 Space
40 Main cover
50 Rear cover
51 Rear wall portion
60 Scan window
91f, 91g Recessed portion
311, 511 Wall surface
312, 313, 512, 513 Peripheral portion
314, 514 Opening
722d, 822d Ridge portion

The invention claimed is:

1. A gantry housing, comprising:
a first cover constituting a front surface portion of the gantry housing, the first cover having a first wall surface including a first opening;
a second cover constituting a rear surface portion of the gantry housing, the second cover having a second wall surface including a second opening; and
a scan window constructed to be X-ray transparent, the scan window being attached between the first cover and the second cover to run along a path of rotation of a gantry, wherein the scan window comprises:
an X-ray transparent member having an inner surface defining a third opening positioned between the first opening and the second opening, and an outer surface;
a first elastic member joined to the outer surface of the X-ray transparent member; and
a second elastic member joined to the outer surface of the X-ray transparent member, the first cover comprises:

a first receiving portion in which the first elastic member is disposed, the first receiving portion having a first surface in contact with the first elastic member; and a first reinforcing portion supporting the X-ray transparent member from the outer surface of the X-ray transparent member, and the second cover comprises:

a second receiving portion in which the second elastic member is disposed, the second receiving portion having a second surface in contact with the second elastic member; and a second reinforcing portion supporting the X-ray transparent member from the outer surface of the X-ray transparent member;

wherein the first cover has a first wall portion having the first wall surface; and wherein the first receiving portion has a first side portion formed in the first wall portion and a second side portion facing the first side portion.

2. The gantry housing as recited in claim 1, wherein the scan window is fitted in the first cover and the second cover by the first elastic member of the scan window is fitted into the first receiving portion of the first cover and the second elastic member of the scan window is fitted into the second receiving portion of the second cover.

3. The gantry housing as recited in claim 1, wherein the second cover has a second wall portion having the second wall surface, and wherein the second receiving portion has a third side portion formed in the second wall portion and a fourth side portion facing the third side portion.

4. The gantry housing as recited in claim 1, wherein the first receiving portion and the first reinforcing portion are integrally formed; and the second receiving portion and the second reinforcing portion are integrally formed.

5. The gantry housing as recited in claim 1, wherein the scan window is fitted in the first cover and the second cover is fixed to the first cover and the second cover by a fixing member.

6. The gantry housing as recited in claim 2, wherein the first receiving portion has a first base portion; and the second receiving portion has a second base portion.

7. The gantry housing as recited in claim 6, wherein the first elastic member is positioned adjacent to the first base portion; and the second elastic member is positioned adjacent to the second base portion.

8. The gantry housing as recited in claim 7, wherein an inner wall surface of the first base portion is the first surface; and an inner wall surface of the second base portion is the second surface.

9. The gantry housing as recited in claim 5, wherein the fixing member fixes the scan window to the first cover in a portion in which the X-ray transparent member and the first reinforcing portion lie adjacent to each other.

10. The gantry housing as recited in claim 5, wherein the fixing member fixes the scan window to the second cover in a portion in which the X-ray transparent member and the second reinforcing portion lie adjacent to each other.

11. The gantry housing as recited in claim 5, wherein the fixing member fixes the scan window to the first cover in a portion opposite to the first reinforcing portion with respect to the first receiving portion.

12. The gantry housing as recited in claim 5, wherein the fixing member fixes the scan window to the second cover in a portion opposite to the second reinforcing portion with respect to the second receiving portion.

* * * * *